(12) United States Patent
Hunziker et al.

(10) Patent No.: US 9,963,704 B2
(45) Date of Patent: May 8, 2018

(54) MODULATING THE INTERACTION BETWEEN ZO-2/TJP2 AND A SNAIL ZINC FINGER TRANSCRIPTION FACTOR FAMILY MEMBER

(71) Applicant: Agency for Science, Technology and Research, Singapore (SG)

(72) Inventors: Walter Hunziker, Proteos (SG); Choon Peng Goh, Proteos (SG)

(73) Assignee: Agency for Science, Technology and Research, Singapore (SG)

( * ) Notice: Subject to any disclaimer, the term of this patent is extended or adjusted under 35 U.S.C. 154(b) by 0 days. days.

(21) Appl. No.: 14/380,583

(22) PCT Filed: Feb. 28, 2013

(86) PCT No.: PCT/SG2013/000080
§ 371 (c)(1),
(2) Date: Aug. 22, 2014

(87) PCT Pub. No.: WO2013/130017
PCT Pub. Date: Sep. 6, 2013

(65) Prior Publication Data
US 2015/0031748 A1    Jan. 29, 2015

(30) Foreign Application Priority Data

Feb. 29, 2012    (SG) .............................. 201201458-5

(51) Int. Cl.
| | | |
|---|---|---|
| *G01N 33/574* | (2006.01) | |
| *C12N 15/113* | (2010.01) | |
| *C07K 16/40* | (2006.01) | |
| *C12N 9/12* | (2006.01) | |
| *C12N 9/96* | (2006.01) | |
| *C07K 14/435* | (2006.01) | |
| *G01N 33/573* | (2006.01) | |

(52) U.S. Cl.
CPC .... *C12N 15/1137* (2013.01); *C07K 14/43504* (2013.01); *C07K 16/40* (2013.01); *C12N 9/1229* (2013.01); *C12N 9/96* (2013.01); *G01N 33/573* (2013.01); *G01N 33/574* (2013.01); *G01N 33/57484* (2013.01); *C12N 2310/14* (2013.01); *C12Y 207/04008* (2013.01); *G01N 2333/91235* (2013.01); *G01N 2500/02* (2013.01); *G01N 2800/52* (2013.01)

(58) Field of Classification Search
CPC ......... G01N 33/57484; G01N 33/5008; C12N 15/1055
See application file for complete search history.

(56) References Cited

U.S. PATENT DOCUMENTS

| H001892 | H * | 10/2000 | Klein ....................... | C12Q 1/18 435/69.1 |
|---|---|---|---|---|
| 2008/0241918 | A1* | 10/2008 | Sasisekharan ..... | G01N 33/5308 435/325 |
| 2010/0298360 | A1* | 11/2010 | Belmares et al. ............ | 514/267 |

FOREIGN PATENT DOCUMENTS

| WO | WO 2006/121219 | 11/2006 |
|---|---|---|
| WO | WO-2007/025231 | 3/2007 |
| WO | WO-2013/130017 | 9/2013 |

OTHER PUBLICATIONS

Ikenouchi et al. Regulation of tight junctions during the epithelium-mesenchyme transition: direct repression of the gene expression of claudins/occludin by Snail. Journal of Cell Science, vol. 116, No. 10, pp. 1959-1967, May 2003.*
GenBank Accession No. NM_004817.3, GI: 282165795, publicly available Dec. 2011.*
GenBank Accession No. NM_003068.4, GI: 324072669, publicly available Dec. 2011.*
GenBank Accession No. NM_003068.4, GI: 324072669, publicly available Feb. 25, 2011.*
Bauer et al. The dual role of zonula occludens (ZO) proteins. Journal of Biomedicine and Biotechnology, vol. 2010, Article ID 402593, printed as pp. 1/11-11/11.*
GenBank Accession No. I46236, GI: 2136456, publicly available Apr. 2004.*
GenBank Accession No. BAF95000.1, GI: 161728293, publicly available Dec. 2007.*
GenBank Accession No. NP_001003202.1, GI: 50978964, publicly available Aug. 2004.*
GenBank Accession No. NP_003059.1 (GI: 11276067, publicly available Nov. 2000.*
Gillespie, ME. Biomarker discovery and compound evaluation using two-hybrid proteomic systems. Expert Opinion on Drug Discovery, vol. 1, No. 5, pp. 389-394, Oct. 2006.*
Rhea et al. Cancer biomarkers: Surviving the journey from bench to bedside. MLO: Medical Laboratory Observer, vol. 43, No. 3, pp. 10-18, Mar. 1, 2011.*
Pavlou et al. The long journey of cancer biomarkers from the bench to the clinic. Clinical Chemistry, vol. 59, No. 1, pp. 147-157, 2013.*
Wilhelm et al. Discovery and development of sorafenib: a multikinase inhibitor for treating cancer. Nature Reviews Drug Discovery, vol. 5, pp. 835-844, Oct. 2006.*
Huttin et al. The BioPlex Network: A systematic exploration of the human proteome. Cell. vol. 162, No. 2, pp. 425-440, Jul. 2015, including pp. 1/403-403/403 of Table S2.*
Bastid et al. The Snail family member Scratch1 is not expressed in human tumors. Oncology Reports, vol. 23, pp. 523-529, 2010.*
Fischer. Peptide, peptidomimetic, and small-molecule antagonists of the p53-HDM2 protein-protein interaction. International Journal of Peptide Research and Therapeutics, vol. 12, No. 1, pp. 3-19, Mar. 2006.*
Hashimoto et al. Turning peptide ligands into small-molecule inhibitors of protein-protein interactions. ChemBioChem, vol. 16, pp. 1855-1856, 2015.*

(Continued)

*Primary Examiner* — Jennifer Dunston
(74) *Attorney, Agent, or Firm* — Schwegman Lundberg & Woessner, P.A.

(57) ABSTRACT

There is provided a method of identifying candidate agents capable of modulating interaction between a first polypeptide and a second polypeptide, wherein the first polypeptide is ZO-2/TJP2 or a functional variant thereof and the second polypeptide is a Snail zinc finger transcription factor family member or a functional variant thereof.

8 Claims, 8 Drawing Sheets

(56) References Cited

OTHER PUBLICATIONS

Juliano et al. Cellular delivery of therapeutic macromolecules. Biochemical Society Transactions, vol. 35, No. 1, pp. 41-43, 2007.*
Aberle, H., et al., "Assembly of the Cadherin-Catenin Complex in Vitro with Recombinant Proteins", J Cell Sci, 107 (Pt 12), (1994), 3655-3663.
Adachi, M., et al., "Normal Establishment of Epithelial Tight Junctions in Mice and Cultured Cells Lacking Expression of ZO-3, a Tight-Junction MAGUK Protein", Mol Cell Biol, 26(23), (2006), 9003-9015.
Ashraf, S. L., et al., "The Mesoderm Determinant Snail Collaborates with Related Zinc-Finger Proteins to Control *Drosophila* Neurogenesis", EMBO J, 18(22), (1999), 6426-6438.
Balda, M. S., et al., "Assembly of the Tight Junction: The Role of Diacylglycerol", J Cell Biol, 123, (1993), 293-302.
Balda, M. S., et al., "The Tight Junction Protein ZO-1 and an Interacting Transcription Factor Regulate Erb-B2 Expression", EMBO J, 19(9), (2000), 2024-2033.
Barrallo-Gimeno, A., et al., "The Snail Genes as Inducers of Cell Movement and Survival: Implications in Development and Cancer", Development, 132(14), (2005), 3151-3161.
Barrios-Rodiles, M., et al., "High-Throughput Mapping of a Dynamic Signaling Network in Mammalian Cells", Science, 307, (2005), 1621-1625.
Batile, E., et al., "The Transription Factor Snail is a Repressor of E-cadherin Gene Expression in Epithelial Tumour Cells", Nat Cell Biol, 2(2), (2000), 84-89.
Beatch, M., et al., "The Tight Junction Protein ZO-2 Contains Three PDZ (PSD-95/Discs-Large/ZO-1) Domains and an Alternatively Spliced Region", J Biol Chem, 271(42), (1996), 25723-25726.
Berrou, L., et al., "A Specific Tryptophan I-II Linker is a Key Determinant of β-Subunit Binding and Modulation in $Ca_v2.3$ Calcium Channels", Biophys J, 83, (2002), 1429-1442.
Betanzos, A., et al., "The Tight Junction Protein ZO-2 Associates with Jun, Fos and C/EBP Transcription Factors in Epithelial Cells", Exp Cell Res, 292, (2004), 51-66.
Bilder, D., et al., "Cooperative Regulation of Cell Polarity and Growth by *Drosophila* Tumor Suppressors", Science, 289, (2000), 113-116.
Bolos, V., et al., "The Transcription Factor Slug Represses E-Cadherin Expression and Induces Epitheial to Mesenchymal Transitions: A Comparison with Snail and E47 Repressors", J Cell Sci, 116(Pt 3), (2003), 499-511.
Boulikas, T., "Putative Nuclear Localization Signals (NLS) in Protein Transcription Factors", J Cell Biochem, 55, (1994), 32-58.
Boussioutas, A., et al., "Distinctive Patterns of Gene Expression in Premalignant Gastric Mucosa and Gastric Cancer", Cancer Res, 63, (2003), 2569-2577.
Brayer, K. J., et al., "Keep Your Fingers Off My DNA: Protein-Protein Interactions Mediated by C2H2 Zinc Finger Domains", Cell Biochem Biophys, 50, (2008), 111-131.
Cano, A., et al., "The Transcription Factor Snail Controls Epithelial-Mesenchymal Transitions by Repressing E-cadherin Expression", Nat Cell Biol, 2, (2000), 76-783.
Carl, T. F., et al., "Inhibtion of Neural Crest Migration in *Xenopus* Using Antisense Slug RNA", Dev Biol, 213, (1999), 101-115.
Carver, E. A., et al., "The Mouse Snail Gene Encodes a Key Regulator of the Epithelial Mesenchymal Transition", Mol Cell Biol, 21(23), (2001), 8184-8188.
Chlenski, A., et al., "Organization and Expression of the Human zo-2 Gene (tjp-2) in Normal and Neoplastic Tissues", Biochim Biophys Acta, 1493, (2000), 319-324.
Choo, Y., "Recognition of DNA Methylation by Zinc Fingers", Nat Struct Biol, 5, (1998), 264-265.
Christophe, D., et al., "Nuclear Targeting of Porteins: How Many Different Signals?", Cell Signal, 12, (2000), 337-341.
Clark, R. A., "Wound Repair", Curr Opin Cell Biol, 1, (1989), 1000-1008.
Cordenonsi, M., et al., "Cingulin Contains Globular and Coiled-Coil Domains and Interacts with Zo-1, Zo-2, Zo-3, and Myosin", J Cell Biol, 147(7), (1999), 1569-1582.
Dalgarno, D. C., et al., "SH3 Domains and Drug Design: Ligands, Structure and Biological Function", Biopolymers, 43, (1997), 383-400.
D'Amati, G., et al., "Myocyte Trandifferentiation: A Possible Pathogenetic Mechanism for Arrhythmogenic Right Ventricular Cardiomyopathy", Arch Pathol Lab Med. 124, (2000), 287-290.
Deguchi, M., et al., "Regain (brain-enriched guanylate kinase-associated protein), a Novel Neuronal PSD-95 / SAP90-Binding Protein", J Biol Chem, 273(41), (1998), 26269-26272.
Dominguez, D., et al., "Phosphorylation Regulates the Subcellular Location and Activity of the Snail Transcriptional Repressor", Mol Cell Biol, 23(14), (2003), 5078-5089.
Drees, F., et al., "Alpha-Catenin is a Molecular Switch That Binds E-Cadherin-Beta-Catenin and Regulates Actin-Filament Assembly", Cell, 123, (2005), 903-915.
Fanning, A. S., et al., "PDZ Domains:Fundamental Building Blocksin the Organization of Protein Complexes at the Plasma Membrane", J Clin Invest, 103, (1999), 767-772.
Fanning, A. S., et al., "The Tight Junction Protein ZO-1 Establishes a Link Between the Transmembrane Protein Occludin and the Actin Cytoskeleton", J Biol Chem, 273(45), (1998), 29745-29753.
Fehon, R. G., et al., "A *Drosophila* Homologue of Membrane-Skeleton Protein 4.1 is Associated with Septate Junctions and is Encoded by the Coracle Gene", Development, 120, (1994), 545-557.
Fluge, O., et al., "Difference in Patterns of Met Expression in Papillary ThyroidCarcinornas and Nonneoplastic Thyroid Tissue", World J Surg, 25, (2001), 623-631.
Fu, M., "Minireview: Cyclin D1: Normal and Abnormal Functions", Endocrinology, 145(12), (2004), 5439-5447.
Furuse, M., et al., "Direct Association of Occludin with ZO-1 and its Possible Involvement in the Localization of Occludin at Tight Junctions", J Cell Biol, 127, (1994), 1617-1626.
Fuse, N., et al., "Diploidy of *Drosophila* Imaginal Cells is Maintained by a Transcriptional Repressor Encoded by Escargot", Genes Dev, 8, (1994), 2270-2281.
Gardiol, D., et al., "Mutational Analysis of the Discs Large Tumour Suppressor Identifies Domains Responsible for Human Papillomavirus Type 18 E6-Mediated Degradation", J Gen Virol, 83, (2002), 283-289.
Giepmans, B. N.G., et al., "The Gap Junction Protein Connexin-43 Interacts with the Second PDZ Domain of the Zona Occludens -1 Protein", Curr Biol, 8(16), (1998), 931-934.
Gmeiner, W. H., et al., "Implications of SH3 Domain Structure and Dynamics for Protein Regulation and Drug Design", Cell Biochem Biophys, 35, (2001), 127-140.
Gonzalez-Mariscal, L., et al., "Molecular Characterization of the Tight Junction Protein ZO-1 in MDCK Cells", Exp Cell Res, 248, (1999), 97-109.
Gonzalez-Mariscal, L., et al., "Role of Tight Junctions in Cell Peoliferation and Cancer", Prog Histochem Cytochem, 42, (2007), 1-57.
Gonzalez-Mariscal, L., et al. "The Tight Junction Protein ZO-2 Has Several Functional Nuclear Export Signals", Exp Cell Res, 312, (2006), 3323-3335.
Gonzalez-Mariscal, L., et al., "Tight Junction Proteins Z)-1, ZO-2 and Occludin along Isolated Renal Tubles", Kidney Int, 57, (2000), 2386-2402.
Gonzalez-Mariscal, L., et al., "MAGUK proteins: Structure and role in the tight junction", Cell Dev Biol, 11(4), (2000), 315-324.
Gottardi, C. J., et al., "Adhesion Signaling: How Beta-Catenin Interacts with Its Partners", Curr Biol, 11(19), (2001), R792-R794.
Gottardi, C. J., et al., "The Junction-Associated Protein, Zonula-Occludens-1, Localizes to the Nucleus Before Maturation and During the Remodeling of Cell-Cell Contacts", Proc Natl Acad Sci USA, 93, (1996), 10779-10784.
Gotzmann, J., et al., "Hepatocytes Convert to a Fibroblastoid Phenotype Through the Cooperation of TGF-beta1 and Ha-Ras: Steps Toward Invasiveness", J Cell Sci, 15, (2002), 189-202.

(56) References Cited

OTHER PUBLICATIONS

Graham, T. A., et al., "Crystal Structure of a Beta-Catenin/Tcf Complex", Cell, 103, (2000), 885-896.
Grimes, H. L., et al., "The GFi-1 Proto-Oncoprotein Contains a Novel Transcriptional Suppressor Domain, SNAG, and Inhibits $G_1$ Arrest Induced by Interlukin-2 Withdrawal", Mol Cell Biol, 16(11), (1996), 6263-6272.
Gumbiner, B., et al., "Identification of a 160kDa Polypetide that Binds to the Tight Junction Protein ZO-1", Proc Natl Acad Sci USA, 88, (1991), 3460-3464.
Hanada, N., et al., "NE-dig, a Mammalian Homolog of *Drosaphila* dig Tumor Suppressor, Induces Growth Suppression and Impairment of Cell Adhesion: Possible Involvement of Down-Regulation of Beta-Catenin by NE-dig Expression", Int J Cancer, 86, (2000), 480-488.
Hashemolhosseini, S., et al., "Strutural Requirements for Nuclear Localization of GCMa/Gcm-1", FEBS Lett, 553, (2003), 315-320.
Haskins, J., et al., "ZO-3, A Novel Member of the MAGUK Protein Family Found at the Tight Junction, Interacts with ZO-1 and Occludin", J Cell Biol, 141, (1998), 199-208.
Hemavathy, K., et al., "Snail/Slug Family of Repressors Slowly Going into the Fast Lane of Development and Cancer", Gene, 257, (2000), 1-12.
Howarth, A. G., et al., "Detection of the Tight-Junction-Associated Protein ZO-1 in Astrocytes and Other Nonepithelial Cell Types", Am J Physiol 262(2 Pt 1), (1992), C461-C469.
Huelsken, J., et al., "New Aspects of Wnt Signaling Pathways in Higher Vertebrates", Curr Opin Genet Dev, 11, (2001), 547-553.
Huerta, M., et al., "Cyclin D1 is Transcriptionally Down-/Regulated by ZO-2 via anE box and the Transcription Factor c-Myc", Mol Biol Cell, 18, (2007), 4826-4836.
Humbert, P., et al., "Dig, Scribble and Lgl in Polarity, Cell Proliferation and Cancer", BioEssays, 25, (2003), 542-553.
Inoue, A., et al., "Slug, a Highly Conserved Zinc Finger Transcriptional Repressor, Protects Hematopoietic Progenitor Cells from Radiation-Induced Apoptosis in Vivo", Cancer Cell, 2, (2002), 279-288.
Inukal, T., et al., "Slug, a ces-1-Related Zinc Finger Transcription Factor Gene with Antiapoptotic Activity, Is a Downstream Target of the E2A-HLF Oncoprotein", Mol Cell, 4, (1999), 343-352.
Ishidate, T., et al., "The APC-hDLG Complex Negatively Regulates Cell Cycle Progression from the G0/G1 to S Phase", Oncogene, 19, (2000), 365-372.
Islas, S., et al., "Nuclear Localization of the Tight Junction Protein ZO-2 in Epithelial Cells", Exp Cell Res, 274, (2002), 138-148.
Itoh, M., et al., "A 220-kD Undercoat Constitutive Protein: Its Specific Localization at Cadherin-based Cell-Cell Adhesion Sites", J Cell Biol, 115(5), (1991), 1449-1462.
Itoh, M., et al., "Characterization of ZO-2 as a MAGUK Family Member Associated With Tight as Well as Adherens Junctions with a Binding Affinity to Occludin and Alpha Catenin", J Biol Chem, 274(9), (1999), 5981-5986.
Itoh, M., et al., "Direct Binding of Three TightJunction-Associated MAGUKs, ZO-1, ZO-2 and ZO-3 with the COOH Termini of Claudins", J Cell Biol, 147(6), (1999), 1351-1363.
Itoh, M., et al. "Involvement of ZO-1 in Cadherin-based Cell Adhesion Through Its Direct Binding to α Catenin and Actin Filaments", J Cell Biol, 138(1), (1997), 181-192.
Jamora, C., et al., "Intercellular Adhesion, Signaling and the Cyctoskeleton", Nat Cell Biol, 4, (2002), E101-E108.
Jaramillo, B. E., et al., "Characterization of the Tight Junction Protein ZO-2 Localized at the Nucleus of Epithelial Cells", Exp Cell Res, 297, (2004), 247-258.
Jesqaitus, L. A., et al., "Molecular Characterization and and Tissue Distribution of ZO-2, a Tight Junction Protein Homologous to ZO-1 and the *Drosophila* Discs-Large Tumor Suppresor Protein", J Cell Biol, 124(6), (1994), 949-961.
Jouanneau, J., et al., "Epithelial Cell Plasticity in Neoplasia", Cancer Cells, 3(12), (1991), 525-529.

Kagan, H. M., et al., "Lysyl Oxidase: Properties, Specificity and Biological Roles Inside and Outside of the Cell", J Cell Biochem, 88, (2003), 660-672.
Kajita, M., et al., "Aberrant Expression of the Transcription Factors Snail and Slug Alters the Response to Genotoxic Stress", Mol Cell Biol, 24(17), (2004), 7559-7566.
Kale, G., et al., "Tyrosine Phosphorylation of Occludin Attenuates its Interactions with ZO-1, ZO-2 and ZO-3", Biochem Biophys Res Commun, 302, (2003), 324-329.
Kataoka, H., et al., "A Novel Snail-Related Transcription Factor Smuc Regulates Basic Helix-Loop-Helix Transcription Factor Activities via Specific E-box Motis", Nucleic Acids Res, 28(2), (2000), 626-633.
Katsube, T., et al., "Cortactin Associates with the cell-cell Junction Protein ZO-1 in Both *Drosophila* and Mouse", J Biol Chem, 273(45), (1998), 29672-29677.
Katsuno, T., et al., "Deficiency of Zonula Occludens-1 Causes Embryonic Lethal Phenotype Affected with Defected Yolk Sac Angiogenesis and Apoptosis of Embryonic Cells", Mol Biol Cell, 19, (2008), 2465-2475.
Kausalya, P. J., et al., "Association of ARVCF with Zonula Occludens (ZO-1) and ZO-2: Binding to PDZ-Domain Proteins and Cell-Cell Adhesion Regulate Plasma Membrane and Nuclear Localization of ARVCF", Mol Biol Cell, 15, (2004), 5503-5515.
Kausalya, P. J., et al., "Connexin45 Directly Binds to ZO-1 and Localizes to the Tight Junction in Epithelial MDCK Cells", FEBS Lett, 505, (2001), 92-96.
Kelly, K. F., et al., "Nuclear Import of the BTB/POZ Transcriptional Regulator Kaiso", J Cell Sci, 117(25), (2004), 6143-6152.
Keon, B. H., et al., "Symplekin, a Novel Kind of Tight Junction Plaque Protein", J Cell Biol, 134, (1996), 1003-1018.
Kim, E., et al., "GKAP, A Novel Synaptic Protein That Interacts with the Guanylate Kinase-LikeDomain of the PSD-95 / SAP90 Family of Channel Clustering Molecules", J Cell Biol, 136, (1997), 669-678.
Kistner, U., et al., "Nucleotide Binding by the Synapse Associated Protein SAP90", FEBS Lett, 359, (1995), 159-163.
Kiyono, T., et al., "Binding of High-Risk Human Papillomavirus E6 Oncoproteins to the Human Homologue of the *Drosophila* Discs Large Tumor Supressor Protein", Proc Natl Acad Sci USA, 94, (1997), 11612-11616.
Klevit, R. E., et al., "Recognition of DNA by $Cys_2$, Hist Zinc Fingers", Science, 253, (1991), 1367,1393.
Ko, H., et al., "Nuclear Localization Signals of the E-cadherin Transcriptional Repressor Snail", Cells Tissues Organs 185(1-3), (2007), 66-72.
Kuwahara, H., et al., "A Novel NE-dig/SAP102-associated Protein, p51-nedasin, Related to the amidohydrolase Superfamily, Interferes with the Association between NE-dig/SAP102 and N-Methyl-D-Aspartate Receptor", J Biol Chem, 274(45), (1999), 32204-32214.
Labonne, C., et al., "Snail-Related Transcriptional Repressors Are Required in Xenopus for Both the Induction of the Neural Crest and its Subsuquent Migration", Dev Biol, 221, (2000), 195-205.
Lallena, M. J., et al., "Transcription-dependent redistribution of nuclear protein 4.1 to SC35-enriched nuclear domains", J Cell Sci 110 (Pt 2), (1997), 239-247.
Lee, S. S., et al., "Binding of Human Virus Oncoproteins to hDig/SAP97, a Mammalian Homolog of the *Drosophila* Discs Large Tumor Suppressor Protein", Proc Natl Acad Sci USA, 94, (1997), 6670-6675.
Leon, O., et al., "Zinc Fingers: DNA-Binding and Protein-Protein Interactions", Biol Res, 33(1), (2000), 21-30.
Leroy, P., et al., "Slug is Required for Cell Survival During Partial Epithelial-Mesenchymal Trnsition of HOF-Induced Tubulogenesis", Mol Biol Cell, 18, (2007), 1943-1952.
Makino, K., et al., "Cloning and Characterization of NE-dig: a Novel Human Hornolog of the *Drosophila* Discs Large (dig) Tumor Suppressor Protein Interacts with the APC Protein", Oncogene, 14, (1997), 2425-2433.
Manzanares, M., et al., "The Increasing Complexity of the Snail Gene Superfamily in Metazoan Evolution", Trends Genet, 17(4), (2001), 178-181.

(56) References Cited

OTHER PUBLICATIONS

Mareel, M. M., et al., "The Invasive Phenotypes", Cancer Metastasis Rev, 9, (1990), 45-62.
Marfatia, S. M., et al., "Modular Organization of the PDZ Domains in the Human-Discs Large Protein Suggests a Mechanism for Coupling PDZ Domain-Binding Proteins to ATP and the Membrane Cytoskeleton", J Cell Biol, 135(3), (1996), 753-766.
Martinez-Alvarez, C., et al., "Snail Family Members and Cell Survival in Physiological and Pathological Cleft Palates", Dev Biol, 265, (2004), 207-218.
Masuko, N., et al., "Interaction of NE-dig/SAP102, a Neuronal and Endocrine Tissue-Specific Membrane-Associated Guanylate Kinase Protein, with almodulin and PSD-95/SAP90. A Possible Regulatory Role in Molecular Clstering at Synaptic Sites", J Biol Chem 274, (1999), 5782-5790.
Matsumine, A., et al., "Binding of APC to the Human Homolog of the *Drosophila* Discs Large Tumor Suppressor Protein", Science, 272, (1996), 1020-1023.
Mattagajasingh, S. N., et al., "Characterization of the Interaction between Protein 4.1R and ZO-2. A Possible Link between the Tight Junction and the Actin Cytoskeleton", J Biol Chem, 275(39), (2000), 30573-30585.
Mauhin, V., et al., "Definition of the DNA-binding Site Repertoire for the *Drosophila* Transcription Factor Snail", Nucleic Acids Res, 21(17), (1993), 3951-3957.
Mayor, R., et al., "A Novel Function for the Xslug Gene:Control of Dorsal Mesendoderm Development by Repressing BMP-4", Mech Dev, 97, (2000), 47-56.
McGee, A. W., et al., "Identification of an Intramolecular Interaction Between the SH3 and Guanylate Kinase Domains of PSD-95", J Biol Chem, 274(25), (1999), 17431-17436.
McGee, A. W., et al., "Structure of the SH3-Guanylate Kinase Module from PSD-95 Suggests a Mechanism for Regulated Assembly of MAGUK Scaffolding Proteins", Mol Cell, 8(6), (2001), 1291-1301.
Mclaughlin, M., et al., "The Distribution and Function of Alternatively Spliced Insertions in hDig". J Biol Chem, 277(8), (2002), 6406-6412.
Metais, J. Y., et al., "hScrib Interacts with ZO-2 at the Cell-Cell Junctions of Epithelial Cells", FEBS Lett, 579, (2005), 3725-3730.
Metzstein, M. M., et al., "The C. elegans Cell Death Specification Gene ces-1 Encodes a Snail Family Zinc Finger Protein", Mol Cell, 4, (1999), 309-319.
Mitic, L. L., et al., "Connexin-Occludin Chimeras Containing the ZO-Binding Domain of Occludin Localize at MDCK Tight Junctions and NRK Cell Contacts", J Cell Biol, 146(3), (1999), 683-693.
Moreno-Bueno, G., et al., "Genetic Profiling of Epitheial Cells Expressing E-Cadherin Repressors Reveals a Distinct Role for Snail, Slug and E47 Factors in Epithelial-Mesenchymal Transition", Cancer Res, 66(19), (2006), 9543-9556.
Muller, S. L., et al., "The Tight Junction Protein Occludin and the Adherens Junction Protein Alpha-Catenin Share a Common Interaction Mechanism with ZO-1", J Biol Chem, 280(5), (2005), 3747-3756.
Nakamura, T., "huASH1 Protein, a Putative Transcription Factor Encoded by a Human Homologue of the *Drosaphila* ASH1 Gene, Localizes to Both Nuclei and Cell-Cell Junctions", Proc Natl Acd Sci USA, 97(13), (2000), 7284-7289.
Nakayama, H., et al., "The Transition to Endoreduplication in Trophoblast Giant Cells is Regulated by the mSNA Zinc Finger Transcription Factor", Devel Biol, 199, (1998), 150-163.
Nibu, Y., et al., "dCtBP Mediates Transcriptional Expression by Knirps, Kruppel and Snail in the *Drosophila* Embryo", EMBO J, 17(23), (1998), 7009-7020.
Nieto, M. A., et al., "Control of Cell Behavior During Vertebrate Development by Slug, a Zinc Finger Gene", Science, 264, (1994), 835-839.
Nix, S. L., et al., "hCASK and hDig Associate in Epithelia, and Their SRC Homology 3 and Guanylate Kinase Domains Participate in Both Intramolecular and Intermolecular Interactions", J Biol Chem, 275(52), (2000), 41192-41200.
Nusslein-Volhard, C., et al., "Mutations Affecting Segment Number and Polarity in *Drosophila*", Nature, 287, (1980), 795-901.
O'Brien, L. E., et al., "Building Epithelial Architecture Insights From Three-Dimensional Culture Models", Nat Rev Mol Cell Biol, 3, (2002), 531-537.
Olmeda, D., et al., "Snai1 and Snai2 Collaborate on Tumor Growth and Mestastasis Properties of Mouse Skin Carcinoma Cell Lines", Oncogene, 27, (2008), 4690-4701.
Ozdamar, B., et al., "Regulation of the Polarity Protein Par6 by TGFbeta Receptors Controls Epithelial Cell Plasticity", Science, 307, (2005), 1603-1609.
Pavletich, N. P., et al., "Zinc Finger-DNA Recognition: Crystal Structure of a Zif268-DNA Complex at 2.1 A", Science, 252, (1991), 809-817.
Peinado, H., et al., "A Molecular Role for Lysyl Oxidase-like 2 Enzyme in Snail Regulation and Tumor Progression", EMBO J, 24, (2005), 3446-3458.
Pemberton, L. F., et al., "Mechanisms of Receptor-Mediated Nuclear Import and Nuclear Export", Traffic, 6, (2005), 187-198.
Perez-Losada, J., et al., "The Radioresistance Biological Function of the SCF/kit Signaling Pathway is Mediated by the Zinc-Finger Transcription Factor Slug", Oncogene, 22, (2003), 4205-4211.
Perez-Losada, J., et al., "Zinc-Finger Transcription Factor Slug Contributes to the Function of the Stem Cell Factorc-kit Signaling Pathway", Blood, 100(4), (2002), 1274-1286.
Perez-Mancera, P. A., et al., "Adipose Tissue Mass is Modulated by Slug (SNAI2)", Hum Mol Genet, 16(23), (2007), 2972-2986.
Perez-Moreno, M. A., et al., "A New Role for E12/E47 in the Repression of E-cadherin Expression adn Epithelial-Mesenchymal Transitions", J Biol Chem. 276(29), (2001), 27424-27431.
Qian, X., et al., "E-Caherin-Mediated Adhesion Inhibits Ligand-Dependent of Diverse Receptor Tyrosine Kinases", EMBO J, 23, (2004), 1739-1748.
Rajasekaran, A. K., et al., "Catenins and Zonula Occludens-1 Form a Complex During Early Stages in the Assembly of Tight Junctions", J Cell Biol, 132(3), (1996), 451-463.
Reichert, M., et al., "The PDZ Domains of Zonula Occludens-1 Induce an Epithelial to Mesenchymal Transition of Madin-Darby Canine Kidney Cells. Evidence for a Role of Beta-Catenin/Tcf/Lef Signaling", J Biol Chern 275(13), (2000), 9492-9500.
Roark, M., et al., "Scratch, a Pan-neural Gene Encoding a Zinc Finger Prtein Related to Snail, Promotes Neuronal Development", Genes Dev, 9, (1995), 2384-2398.
Ros, M. A., et al., "Slug, a Zinc Finger Gene Previously Implicated in the Early Patterning of the Mesoderm and the Neural Crest, is Also Involved in Chick Limb Development", Development, 124, (1997), 1821-1829.
Satoh, K., et al., "DAP-1, a Novel Protein That Interacts with the Guanylate Kinase-like Domains of hDLG and PSD-95", Genes Cells, 2, (1997), 415-424.
Savagner, P., et al., "Developmental Transcription Factor Slug is Required for Effective Re-epithelialization by Adult Keratinocytes", J Cell Physiol, 202, (2005), 858-866.
Schmidt, A., et al., "Occludin Binds to the SH3-hinge-GuK Unit of Zonula Occludins Protein 1: Potential Mechanism of Tight Junction Regulation", Cell Mol Life Sci, 61, (2004), 1354-1365.
Sefton, M., et al., "Conserved and Divergent Roles for Members of the Snail Family of Transcription Factors in the Chick and mouse Embryo", Development, 125, (1998), 3111-3121.
Shih, J. Y., et al., "Transcription Repressor Slug Promotes E-Cadherin Carcinoma Invasion and Predicts Outcome of Patients with Lung Edenocarcinoma", Clin Cancer Res, 11, (2005), 8070-8079.
Stade, K., et al., "Exportin 1 (Crm1p) is an Essential Nuclear Export Factor", Cell, 90, (1997), 1041-1050.
Stevenson, B. R., et al., "Identification of ZO-1; a High Molecular Weight Polypeptide Associated with the Tight Junction (Zonula Occludens) in a Variety of Epithelia", J Cell Biol 103, (1986), 755-766.
Takai, E., et al., "Correlation of Translocation of Tight Junction Protein Zonula-Occludens-1 and Activation of Epidermal Growth

(56) References Cited

OTHER PUBLICATIONS

Factor Receptor in the Regulation of the Invasion of Pancreatic Cancer Cells", Int J Oncol, 27, (2005), 645-651.
Takeuchi, M., et al., "A Family of PSD-95/SAP90-associated Proteins Localized at Postsynaptic Density", J Biol Chem, 272(18), (1997), 11943-11951.
Tang, V W., "Proteomic and bioinformatics analysis of epithelial tight junction reveals an unexpected cluster of synaptic moldecules", Biol Direct, 1, (2006), 30 pgs.
Tapia, R., et al., "Zona Occldens-2 Inhibits Cyclin D1 Expression and Cell Proliferation and Exhibits Changes in Localization Along the Cell Cycle", Mol Biol Cell, 20, (2009), 1102-1117.
Thiery, J. P., "Cell Adhesion in Development: A Complex Signaling Network", Curr Opin Genet Dev, 13, (2003), 365-371.
Thiery, J. P., et al., "Complex Networks Orchestrate Epithelial-Mesenchymal Transitions", Nat Rev Mol Cell Biol, 7, (2006), 131-142.
Thualt, S., et al., "Transforming Growth Factor-beta Employs HMGA2 to Elicit Epithelial-Mesenchymal Transition", J Cell Biol, 174(2), (2006), 175-183.
Toyofuku, T., et al., "Direct Association of the Gap Junction Protein Connexin-43 with ZO-1 in Cardiac Myocytes", J Biol Chem, 273(21), (1998), 12725-12731.
Traweger, A., et al., "The Tight Junction Protein ZO-2 Localizes to the Nucleus and Interacts with the Heterogeneous Nuclear Ribonucleoprotein Scaffold Attachment Factor-B", J Biol Chem, 278(4), (2003), 2692-2700.
Tsukita, S., et al., "Occludin and Claudins in Tight-Junction Strands: Leading or Supporting Players?", Trends Cell Biol, 9, (1999), 268-273.
Umeda, K., et al., "ZO-1 and ZO-2 Independently Determine Where Claudins are Polymerized in Tight-Junction Strand Formation", Cell, 126, (2006), 741-754.
Valdes, F., et al., "The Epithelial Mesenchymal Transition Confers Resistance to the Apoptotic Effects of Transforming Growth Factor Beta in Fetal Rat Hepatocytes", Mol Cancer Res, 1, (2002), 68-78.
Van Itallie, C. M., et al., "Occludin Confers Adhesiveness When Expressed in Fibroblasts", J Cell Sci, 110 (Pt 9), (1997), 1113-1121.
Vega, S., et al., "Snail Blocks the Cell Cycle and Confers Resistance to Cell Death", Genes Dev, 18, (2004), 1131-1143.
Vietor, I., et al., "Perturbation of the Tight Junction Permeability Barrier by Occluden Loop Peptides Activates Beta-Catenin/TCF/LEF-Mediated Transcription", EMBO Rep, 2(4), (2001), 306-312.
Whiteley, M., et al., "The *Drosophila* Gene Escargot Encodes a Zinc-Finger Motif Found in Snail-Related Genes", Mech Dev, 36, (1992), 117-127.
Wittchen, E. S., et al., "Exogenous Expression of the Amino-Terminal Half of the Tight Junction Protein ZO-3 Peturbs Junctional Complex Assembly", J Cell Biol, 151(4), (2000), 825-836.

Wittchen, E. S., et al., "Protein Interactions at the Tight Junction. Actin has Multiple Binding Partners, and ZO-1Forms Independent Complexes with ZO-2 and ZO-3", J Biol Chem, 274(49), (1999), 35179-35185.
Woods, D. F., et al., "Dlg Protein is Required for Junction Structure, Cell Polarity and Proliferation Control in *Drosphila* Epithelia", J Cell Biol, 134(6), (1996), 1469-1482.
Woods, D. F., et al., "Localization of Proteins to the Apico-Lateral Junctions of *Drosophila* Epithelia", Dev Genet, 20, (1997), 111-118.
Woods, D. F., et al., "Molecular Cloning of the Lethal (1) Discs Large-1 Oncogene of *Drosophila*", Dev Biol, 134(1), (1989), 222-35.
Woods, D. F., et al., "The Discs-Large Tumor Suppressor Gene of *Drosophila* Encodes a Guanylate Kinase Homolog Localized at Septate Functions", Cell, 66, (1991), 451-464.
Xu, J., et al., "Early Embryonic Lethality of Mice Lacking ZO-2, but Not ZO-3, Reveals Critical arid Nonredundant Roles for the Individual Zonula Occldens Proteins in Mammalian Development", Mol Cell Biol, 28(5), (2008), 1669-1678.
Yamada, Y., et al., "Activation of Channel Activity of the NMDA receptor-PSD-95 Complex by Guanylate Kinase-Associated Protein (GKAP)", FEBS Lett, 458, (1999), 295-298.
Yamasaki, H., et al., "Zinc Finger Domain of Snail Functions as a Nuclear Localization Signal for Importin beta-mediated Nuclear Import Pathway", Genes Cells, 10, (2005), 455-464.
Yang, Z., et al., "Phosphotylation of Snail, a Master Regulator of Epithelial-to-Mesenchyme Transition, Modulates Snail's Subcelluar Localization and Functions", Cancer Res, 65(8), (2005), 3179-3184.
Yook, J. L., et al., "Wnt-dependent Regulation of the E-cadherin Repressor Snail", J Biol Chem, 280(12), (2005), 11740-11748.
Zhang, Y., et al., "Convergent and Divergent Ligand Specifity Among PDZ Domains of the LAP and Zonula Occludens (ZO) Families", J Biol Chem, 281(31), (2006), 22299-22311.
Zhou, B. P., et al., "Dual Regulation by Snail byGSK-3beta-mediated Phosphorylation in Control of Epithelial-Mesenchymal Transition", Nat Cell Biol, 6(10), (2004), 931-940.
Zweidler-McKay, P. A., et al., "Gfi-1 Encodes a Nuclear Zinc Finger Protein That Binds DNA and Functions as a Transcriptional Repressor", Mol Cell Biol, 16(8), (1996), 4024-4034.
"International Application No. PCT/SG2013/000080, International Search Report and Written Opinion dated Aug. 16, 2013", (dated Aug. 16, 2013), 12 pgs.
Glaunsinger, Britt A., et al., "Link of the unique oncogenic properties of adenovirus type 9 E4-ORF1 to a select interaction with the candidate tumor suppressor protein ZO-2", The EMBO Journal, vol. 20, No. 20, pp. 5578-5586 (2001), (Aug. 23, 2001), 5578-5586.
Oka, Tsutomu, et al., "Functional complexes between YAP2 and ZO-2 are PDZ domain-dependent, and regulate YAP2 nuclear localization and signalling", Biochem. J. (2010) 432, 461-472, (Sep. 24, 2010), 461-472.

\* cited by examiner

ZNF3 ALIGNMENT
Slug    186    CVCKICGKAFSRPWLLQGHIRTHTGEKP    213
Zif268  107    CPVESCDRRFSQSGSLTR HIRIHTGQKP134
               -1 23 6
ZNF4 ALIGNMENT
Slug    214    FSCPHCNRAFADRSNLRAHLQTHSDVKK    241
Zif268  135    FQCRICMRNFSRSDHLTTH IRTHTGEKP    162
               -1 23 6
ZNF5 ALIGNMENT
Slug    242    YQCKNCSKTFSRMSLLHKHEESGC        265
Zif268  163    FACD ICGRKFARSDERKRHTKIHL       186
               -1 23 6

| NU FLAG ZO2 3PSGAP | ENHANCED NU STAINING OF GFP-SLUG | NORMAL NU STAINING OF GFP-SLUG | TOTAL |
|---|---|---|---|
| TRANSFECTED (OBSERVED) | a = 38 | b = 16 | a+b = 54 |
| NON-TRANSFECTED (OBSERVED) | c = 10 | d = 202 | c+d = 212 |
| TOTAL | a+c = 48 | b+d = 218 | a+b+c+d = 266 |

SEQUENCE LISTING

```
<160> NUMBER OF SEQ ID NOS: 31

<210> SEQ ID NO 1
<211> LENGTH: 4730
<212> TYPE: DNA
<213> ORGANISM: Artificial Sequence
<220> FEATURE:
<223> OTHER INFORMATION: A synthetic tight Junction Protein 2 (ZO-2) of
      Canis lupus familiaris

<400> SEQUENCE: 1
caccaccctc accccacact gtaggggtac acagtgaggg gtacacggaa catctaaaag      60 cacagggct  ttgggtagcg caaagattac ttcgattgct tcagctgatc agtgcccaaa     120
atgtacatga ccttttactg agagagacaa gatgaggtac aagaagtaca tggccatcct     180
ggaagccgca gtgggtatca ccccacttaa caaaagagag cttcttcctg agagcagaag     240
acatgtgaat ctctggcagc accccggggt gcggagtacc acgttattat cgtctccctg     300
cgagtgggat tggcccttcg gctgtacctc ctggcacgag cattccacag agcacagacg     360
tgcgctggca ggcagcctgc tttccaggc cccaggcatg gaagaactga tatgggagca     420
gtacactgtg accctacaaa aggattccaa aagaggattt ggaattgcag tgtccggagg     480
cagagacaac ccccactttg aaaatggaga acgtcaatc gtcatttctg acgtgctacc     540
gggtgggcct gctgatgggc tgcttcaaga aaatgacagg tgtggtcatgg ttaacggcac     600 ccccatggag gatgtgctcc attcatttgc tgtccagcag ctgagaaaaa gtgggaagat     660
cgctgccatt gtggtcaaga ggccccgaa ggtccagctg gccccgcccc agggcagcct     720
acccgtcgat gaggatgacc gtgcttttga ggtgatggat gagttcgatg gcagaagtgc     780
ccgcagcggg tacagcgaga ggagccggcg cagcagccac ggtgggcgca gccgcagctg     840
ggaggacagc ccggagaggg ggcgtcccca tgagcgggcg tggagccagg agcgcgagcg     900
cagccgtggc cggagcctgg agcggggcct ggaccatgac gatgactacc ggcggcctcg     960
agagcgcagc cggggccgga gcctggagcg gggcctggac catgacgatg actacgggcg    1020
gcccggagag cgcagccacg gcatgagcac tgacagggc tacgaccgtg gctacgaccg    1080
tggctacgac cgtggctacg accgcaccta tagcccagag gccgagtatg ccgcaggac     1140 ccagcctgat gccggcacg cagggtcccg gagccgcagc cgcagcact tgcgctcccg     1200 cagcccagc cctgagctga ggggcggcc ggaccatgca ggccagcctg actcggacag     1260
gcccatcggg gtccttctga tgaaaagcaa agcaaatgaa gagtacggtc tccggcttgg    1320
```

```
gagtcagatc ttcataaagc aaatgaccag aaccgctctg gcaactaaag atggcaacct    1380
gcacgaagga gacataattc tcaagataaa tggaactgta actgagaaca tgtctttaac    1440
tgatgcccga aaactgatag aaaagtcaag aggaaaactc caactagtgg tgttgagaga    1500
cagcaagcaa acgctcatca acattccatc attaaatgac agcgactctg aaatagaaga    1560
tatctcagaa atagagtcaa accgatcatt ttctccagag gagagacggc agcagtattc    1620
cgactatgat tatcattcct caaatgaaaa actgaaggaa aggccaaatt caagagagga    1680
catgcagaac agatggtcca ggatgggcgc cacacccact cccttttaagt ccatggggga    1740 tattgcatct gtggttggca cagagaacag caaggaaccc agataccaag gaaccacc     1800 agctcctcaa cctaaagcag ccccaagaac ttttcttcgc ccgagtcctg aagatgaagc    1860
aatatatggt cccaatacca aaatggtgag gtttaagaag ggagacagcg tgggactccg    1920
attggctggt ggcaatgacg ttgggatatt tgtggctggt attcaagagg gtacctcggc    1980
agaacaagaa ggccttcaag agggggacca gattctgaag gtgaacacac aggatttcag    2040
agggctagtt cgggaagatg ccgttctcta cctgctagaa atccctaaag gtgaaatggt    2100
gaccatttta gctcagagcc gagctgatgt gtatagagac atcctggctt gtggcagagg    2160
ggactcattt tttataagaa gccactttga atgtgagaag gaaactccac agagcctggc    2220
cttcagcagg ggggaggtct tccgagttgt agatacactg tatgatggca agctgggcca    2280
ctggctggct gtgaggattg gaacgaatt ggagaagggc ttaatcccca acaaaagcag    2340
agctgaacaa atggccagtg ttcagaatgc ccagagagac aatgctgggg acagagcaga    2400
tttctggaga atgcgtggcc agagatctgg catgaagaag aacttaagga aaagtcggga    2460
agatctaaca gctgctgtgt cagttagcac caagttccca gcttacgaaa gggttttgct    2520
gcgagaagct ggtttcaaga gacctgtggt cttatttggc cctatagcag atatagcctt    2580
ggaaaagttg gcaaatgagt taccggacct gttccaaact gctaaaacgg aaccaaaaga    2640
tgcaggatcc gagaaatcta gtggggtggt ccggttaaat actgtgaggc aaattattga    2700
acaggataag catgcactat tggatgtgac tcctaaagct gtggacctgt tgaattatac    2760
tcagtggttc ccgattgtga ttttttttcaa cccagactct agacaaggtg tcaaaaccat    2820
gagacagagg ttgaatccaa catccaacaa aagttctcgg aagttgtatg atcaagccaa    2880
caagcttaag aaaacgtgtg cacatctttt tacagctact atcaacctaa attcagccaa    2940
tgatagctgg tttggcagct tgaaggacac aattcagcat cagcaaggag aagcagtttg    3000
ggtctctgaa ggaaagatgg aagggatgga tgatgaccct gaagaccgca tgtcctactt    3060
aactgccatg ggcgcagact atctgagttg cgacagccgc ctcatcagtg actttgaaga    3120
caccgacggt gaaggaggtg cctacactga caatgagctg gatgagccag ctgaggagcc    3180
actggtgtct tccatcaccc gctcctcgga gccggtgcag catgaggaga gcataaggaa    3240
gcccagccca gagccacgag ctcagatgag gagggctgct agcagagatc aacttaggga    3300
cagtagtcca ccccccgcat tcaagccaga gccgcccaag gccaaaactc agaacagaga    3360
agaatccttt gacatctcca gatcccatga ctataagtca aacccctcag ccgttgctgg    3420
taatgaagtt tctggggcat ctaccagaag ctgtcctcct cctattgcag caaaaccttc    3480
ctttggaagg tctatactga agccctccac tcctgtccct tccccagaga gtgaggaggt    3540
gggagagggc agtgaagagc aagaaggcgc tcccaagtct gtcctgggca agttaaaat    3600 atttgagaag atggatcaca aggcaagatt acagagaatg caggagcttc aagaagcaca    3660
```

| | |
|---|---|
| gaatgcaagg attgaaattg ctcagaagca tcctgacatc tatgcagttc caatcaaaac | 3720 |
| acacaagcca gaccctggcc tgtcccagca cacaagttcc aggccacccg agccccagaa | 3780 |
| aggcccttcc aggctctacc aggatcccag aggaagttat ggcagtgatg ctgaagagga | 3840 |
| agaataccgc cagcagctgt ccgaacactc gaagcgtggc tattacagcc agccttcccg | 3900 |
| gtaccgggac acggaattat agatgcctga tagtcggcgt gtccgtctcc ccactgccac | 3960 |
| cacctcggag cagcgctccc actgagcatg cgacggttct ttctagggaa agtgcactgc | 4020 |
| ggagatttgg gaccctgaac tcccatttcc tcaaggggag ccccgggggc agccaatgca | 4080 |
| aataaaaact gagggctctg tttgtggaac tgggtcttga gagttgatgg cttttttgctc | 4140 |
| agaatcaaga gaaacactac agtctgatac tgttacctgc ttcagtggac caaaatttgt | 4200 |
| attaattctg tttgcgtatt tttaacatgt atattaagaa gtgataacta ttttcccctca | 4260 |
| ttaatatctg cctttgagga ctgtttcaat gagagatgga atgtgaaaaa ggaattaaaa | 4320 |
| tgctgttgga ctcccaacta aattcaaaga aatattttat tacaactcta agtgcctttg | 4380 |
| atgagaagtg tcttaaatat tcttcctttg aagctttatg caaagccata atggactaag | 4440 |
| actattttga ctaaagtttt ataccagctt aataactatg gttttctctg cactgtgtca | 4500 |
| tcttttcaag gcatttgtct ttgtaatatt ttccataaac tctgtatata tagtagctac | 4560 |
| atgtggtagt tcagctacca gtgctaaata gcttgacgac caagaaattg gtatagaaat | 4620 |
| ttttgtttaa accatgtgct ccagaaaagc agatacttgg aaaaactgta tttccaaaag | 4680 |
| tgtgtgtatt gacaacagtt ttataattta ataaaaagga gattgaaatc | 4730 |

<210> SEQ ID NO 2
<211> LENGTH: 4637
<212> TYPE: DNA
<213> ORGANISM: Artificial Sequence
<220> FEATURE:
<223> OTHER INFORMATION: A synthetic tight Junction Protein 2 (ZO-2)
      isoform 1 of Mus musculus

<400> SEQUENCE: 2

| | |
|---|---|
| ggcgggccgg ctgcgccgcg ggaggaggga caaagggag gctccggtg gtggcgaacc | 60 |
| gggtcctcca ctgcagcttg tagttctgag ccgcggcgag gaggacgtgc gggaagcgcg | 120 |
| cgcgagatgc cggtgcgggg agaccgcggg ttcccaccgc ggcgggagct gtcgggctgg | 180 |
| cagcgcggtc caggcatgga ggaggtgata tgggagcagt acaccgtgac cctgcagaag | 240 |
| gattccaaaa gaggatttgg aattgccgtg tcgggaggca gagacaaccc ccactttgaa | 300 |
| aatggggaga cgtcaatcgt catctcagat gtgctcccag gtggacccgc tgatggcttg | 360 |
| cttcaagaaa atgacagggt ggtcatggtc aatggcaccc ccatggaaga tgtgctccat | 420 |
| tcgtttgccg ttcagcagct taggaaaagt gggaagatag cagccatcgt ggtcaagaga | 480 |
| ccccggaagg ttcaggtggc ccactgcaa ggcagccccc ctctcagtca tgacgaccga | 540 |
| ggttttgaag tgattgaaga atttgatggc agaagtttcc gcagcggcta cagtgagagg | 600 |
| agtcggcaca gcagccacga catgctcagc cacagctggg agggcaatag ggagagggg | 660 |
| cgacccccatc agcgcacaca gagccgggag cgggagcgca gccgtggcag gagcctggaa | 720 |
| cggggcctgg accaggaaga ctatgggcgc agccgtgagc gcagccgtgg ccggagcctg | 780 |
| gagcgcgggc tggaccgcga ctttgtgtcc agggaccaca gccgtggccg tagcatcgac | 840 |
| agggactacg accgagacta tgagcgctcc tatcacgaag cttatgaacc cgactacgga | 900 |
| ggcggctaca gcccatcata tgaccgtaga gcccatccag agaccgcta tgaacggagc | 960 |

```
cgcagccgag aacacctacg ttcccgaagc cccagccccg agtctaggtc acggcatgaa    1020
cacaagggcc aacatgatcc cgacaggccc atcggggtcc ttctaaccaa aagcaaagca    1080
aatgaagagt atgggctccg gctggggagt cagatcttca tcaaagaaat gaccagaaca    1140
ggactggcca ccaaagatgg caaccttcat gaggggaca taattctcaa gatcaacggc     1200
actgttactg agaacatgtc tctaacggat gctcggaagt aatagaaaa gtctcgagga     1260 aaactgcagt tgtggtgtt gagagacagc aagcagaccc tcatcaacat cccagcccta    1320
aacgacagcg actctgaagt ggaggatatc tcggaaatag agtccaaccg gtctttctct    1380
ccagaggaga gacgccagca gtattctgat caggattacc attcctccac tgagaagctg    1440
aaggagaggc cgagctcaag agaggagacc tcaggcagac tatccaggat gggtgccact    1500
cccacgccgt tcaagtccac gggggacatc acagctgcgg gggtcacaga ggccagcagg    1560
gagcccaggt accaggaaga aggcccagtt cctcaaccca gaacagctcc aagagttttt    1620
cttcgtccta gtcccgaaga tgaagcaata tatggcccta acaccaaaat ggtgaggttc    1680
aagaagggag acagcgtggg cctccggttg gctggtggaa acgacgttgg gatatttgtg    1740
gctggcattc aggagggcac ctccgcagag caggagggcc tgcaagaagg agaccagatt    1800
ctgaaggtga acacacagga tttcagaggg ctagtccggg aagatgcggt cctctacctg    1860
ctagaaatcc ccaaaggtga aactgtgacc attttggctc agagccgagc agacgtgtac    1920
agagatatcc tggcttgtgg caggggagat tcgttttca taagaagcca cttgaatgt     1980 gagaaggaaa ctccccagag cctggccttc accaggggag aggtcttccg agtggtagac    2040
acgctgtacg atggcaagct gggccactgg ctggccgtga ggatcgggaa tgagctggag    2100
aaaggcttga tccctaacaa aagcagagcc gagcaaatgg ccagtgtcca gaatgcccag    2160
cgagagaacg ccggggacag agcagacttc tggcggatgc gtggccagag atccagcggc    2220
ggcgtcaaga agaacctccg caagagccgg gaagacctgg cggctgctgt atcggttagc    2280
accaagttcc ctgcctacga gaaggttctg cttcgggaag ctggcttcaa gagacccgtg    2340
gttctgtttg gccccatagc agatatagca atggaaaggt tggcaactga gttaccagac    2400
ctgtttcaaa ctgcaaaaac agaacccaaa gatgccggat ctgagaaatc cagtggagtg    2460
gttcggttga ataccgtgag gcaaattatt gagcaggaca agcacgccct gctcgacgtt    2520 accccccaaag ctgtggacct gctcaactac actcagtggt tccctatcgt gattttcttc    2580
aacccggatt ccagacaagg tgttaaaacc ataaggcaga ggttgagtcc aacatccaat    2640
aaaagttctc gcaagttatt tgatcaagcc aacaagctca aaaagacctg ttctcatctt    2700
tttacagcca caatcaacgt gaattcagcc aacgatggct ggtttggcag cttgaaggac    2760
agcattcagc agcagcaaaa cgaagcagtc tgggtctctg aaggaaagat ggaagggatg    2820
gatgatgatg ctgaagaccg catgtcctac ttaaccgcca tgggcgcgga ctatctgagt    2880
tgtgacagcc gtctcatcag tgactttgaa gacaccgacg gcgagggagg cgcctacact    2940
gacaatgagc tagaggagcc ggcggaggag ccgctggtgt cttccatcac ccgctcctcg    3000
gagccggtgc agcacgagga gaacataagg aaatccagcc cagagccacg agctcagatg    3060
aggagggctg ctagcagaga ccaacttagg gatgctagcc cgccccagc cttcaagcca    3120 gagccgccca aggcaagaag ccagaacaga gaagactcct tcgactactc caagtcaaac    3180
ctcccgccca cagccggcag tgaaatcccg ggggatcca ccaaaggcta tcctcccccct    3240 attgcagcga agcctgcctt tgggcggccc atcctgaagc cttccactcc agtccctatg    3300
cctgagagcg aggaggttgg agagagcacc gaggagcagg aagatgctcc cagatcagtc    3360
```

```
ctgggcagag tgaaaatatt cgagaagatg gaccacaagg caaaattaca gaggatgcag    3420
gagctccagg aggcccagaa tgcgaggatc gaaatagctc agaagcaccc tgacatctat    3480
gcggttccaa tcaaggcccc caagccagat gctggcctcc cccgcacat  gagttctaga    3540 cccccagagc cccagaaagc tccttccaga ctttaccagg acaccagagg aagctacggc    3600
agtgaccccg aggaggagga gtaccgccag cagttggcag cacactcgaa gcgtggttac    3660
tacagccagc cctcccggta ccgagacacg gagttataga gcttgtatgc gtggactcct    3720
gcgaggccac ctggagatct tctccagtta aaacgcactg cagagatacg gtggggaccc    3780
aggcaacaga tggcatgagt tatcaactga aggctctgtt tgtgggactg gagtgaagtt    3840
gattctgact tcttgaatg  aagagaaaca gtctgataac tgttacttgc tttggtgtgg    3900
accaagatct gtattaacct ctctgtattt tttaatatgt atatcgagca ataactatct    3960
ttcctcactc gtggctgcct tcctgcacag cttcagtgtg aagcagatgt gaagagggag    4020
ttaaaaaaaa aaaaaaaaaa aggactccgt ctcagactaa gttcagaagt attttatcac    4080
gactctctaa gtgcctttga caaaatgtgt ctcacgtttg cctccctccc tgacgcttca    4140
tgcaaaccca taatggacta aactttatt  ttgactaaat ttttatacca gtttagcagc    4200
tgtgactgcc cctgcaccat gccacctttt cagggcattg tctgtagtat tttccacaaa    4260
ttctgactgt acataggaca gcgaccctcg ggagtgtgtc tgcctatcaa ttctgcgtag    4320
ctcggaggcc aagattttag agtgtttgtc cgttgtctgg aaccacatat tccacaaagg    4380
cagagacttg agaaaagggt attttgtttc ctctctatca gagtatgtac tgacatcggg    4440
tggttttgta atttaataaa aaggagtaca agaatgagtt tagtgctgag tctctacaca    4500
ccttccttct gggcagtgtg gggggaaccc aaggtcctca tgcattcaga gtgctgcttc    4560
accactgaac tacaccccac tcttcctgat ttatttttaat taaaaaaatt tttaaaagaa    4620
caaaaaaaaa aaaaaaa                                                  4637

<210> SEQ ID NO 3
<211> LENGTH: 4627
<212> TYPE: DNA
<213> ORGANISM: Artificial Sequence
<220> FEATURE:
<223> OTHER INFORMATION: A synthetic tight Junction Protein 2 (ZO-2)
      isoform 2 of Mus musculus

<400> SEQUENCE: 3
gagtcacaac aatacccagg aacggccggt ggcggaggtc actggctccc gcctgctgcg     60
gcagcccgcg gcactccgcc tccggacagg cgctgcccgc gctgcgccgc ccgacgcctg    120
ggaccgtcgc tttctgcgcg ctgactctgc tggctgccgc cgcccccctt ctccagggtc    180
caggcatgga ggaggtgata tgggagcagt acaccgtgac cctgcagaag gattccaaaa    240
gaggatttgg aattgccgtg tcgggaggca gagacaaccc ccactttgaa atggggagga    300
cgtcaatcgt catctcagat gtgctcccag gtggacccgc tgatggcttg cttcaagaaa    360
atgacagggt ggtcatggtc aatggcaccc ccatggaaga tgtgctccat tcgtttgccg    420
ttcagcagct taggaaaagt gggaagatag cagccatcgt ggtcaagaga ccccggaagg    480
ttcaggtggc cccactgcaa ggcagccccc ctctcagtca tgacgaccga ggttttgaag    540
tgattgaaga atttgatggc agaagtttcc gcagcggcta cagtgagagg agtcggcaca    600
gcagccacga catgctcagc cacagctggg agggcaatag ggagagggg  cgaccccatc    660 agcgcacaca gagccgggag cgggagcgca gccgtggcag gagcctggaa cggggcctgg    720
```

```
accaggaaga ctatgggcgc agccgtgagc gcagccgtgg ccggagcctg gagcgcgggc    780
tggaccgcga ctttgtgtcc agggaccaca gccgtggccg tagcatcgac agggactacg    840
accgagacta tgagcgctcc tatcacgaag cttatgaacc cgactacgga ggcggctaca    900
gcccatcata tgaccgtaga gcccatccag agacccgcta tgaacggagc cgcagccgag    960
aacacctacg ttcccgaagc cccagccccg agtctaggtc acggcatgaa cacaagggcc   1020
aacatgatcc cgacaggccc atcggggtcc ttctaaccaa aagcaaagca aatgaagagt   1080
atgggctccg gctggggagt cagatcttca tcaaagaaat gaccagaaca ggactggcca   1140
ccaaagatgg caaccttcat gaggggggaca taattctcaa gatcaacggc actgttactg   1200
agaacatgtc tctaacggat gctcggaagt aatagaaaaa gtctcgagga aaactgcagc   1260
ttgtggtgtt gagagacagc aagcagaccc tcatcaacat cccagcccta acgacagcg    1320
actctgaagt ggaggatatc tcggaaatag agtccaaccg gtctttctct ccagaggaga   1380
gacgccagca gtattctgat caggattacc attcctccac tgagaagctg aaggagaggc   1440
cgagctcaag agaggagacc tcaggcagac tatccaggat gggtgccact cccacgccgt   1500
tcaagtccac gggggacatc acagctgcgg gggtcacaga ggccagcagg agcccaggt    1560
accaggaaga aggcccagtt cctcaaccca gaacagctcc aagagttttt cttcgtccta   1620
gtcccgaaga tgaagcaata tatggcccta acaccaaaat ggtgaggttc aagaagggag   1680
acagcgtggg cctccggttg gctggtggaa cgacgttgg gatatttgtg ctggcattc    1740
aggagggcac ctccgcagag caggagggcc tgcaagaagg agaccagatt ctgaaggtga   1800
acacacagga tttcagaggg ctagtccggg aagatgcggt cctctacctg ctagaaatcc   1860
ccaaggtga aactgtgacc attttggctc agagccgagc agacgtgtac agagatatcc   1920
tggcttgtgg caggggagat tcgttttcca taagaagcca ctttgaatgt gagaaggaaa   1980
ctccccagag cctggccttc accagggag aggtcttccg agtggtagac acgctgtacg   2040
atggcaagct gggccactgg ctggccgtga ggatcgggaa tgagctggag aaaggcttga   2100
tccctaacaa aagcagagcc gagcaaatgg ccagtgtcca gaatgcccag cgagagaacg   2160
ccggggacag agcagacttc tggcggatgc gtggccagat atccagcggc ggcgtcaaga   2220
agaacctccg caagagccgg gaagacctgg cggctgctgt atcggttagc accaagttcc   2280
ctgcctacga gaaggttctg cttcgggaag ctggcttcaa gagacccgtg gttctgtttg   2340
gccccatagc agatatagca atggaaaggt tggcaactga gttaccagac ctgtttcaaa   2400
ctgcaaaaac agaacccaaa gatgccggat ctgagaaatc cagtggagtg gttcggttga   2460
ataccgtgag gcaaattatt gagcaggaca gcacgccct gctcgacgtt accccaaag    2520
ctgtggacct gctcaactac actcagtggt ccctatcgt gatttcttc aacccggatt    2580
ccagacaagg tgttaaaacc ataaggcaga ggttgagtcc aacatccaat aaaagttctc   2640
gcaagttatt tgatcaagcc aacaagctca aaaagacctg ttctcatctt tttacagcca   2700
caatcaacgt gaattcagcc aacgatggct ggtttggcag cttgaaggac agcattcagc   2760
agcagcaaaa cgaagcagtc tgggtctctg aaggaaagat ggaagggatg gatgatgatg   2820
ctgaagaccg catgtcctac ttaaccgcca tgggcgcgg ctatctgagt tgtgacagcc    2880
gtctcatcag tgactttgaa gacaccgacg gcgagggagg cgcctacact gacaatgagc   2940
tagaggagcc ggcggaggag ccgctggtgt cttccatcac ccgctcctcg gagccggtgc   3000
agcacgagga gaacataagg aaatccagcc cagagccacg agctcagatg aggagggctg   3060
```

```
ctagcagaga ccaacttagg gatgctagcc cgccccagc cttcaagcca gagccgccca    3120
aggcaagaag ccagaacaga gaagactcct tcgactactc caagtcaaac ctccccgcca    3180
cagccggcag tgaaatcccg gggggatcca ccaaaggcta tcctccccct attgcagcga    3240
agcctgcctt tgggcggccc atcctgaagc cttccactcc agtccctatg cctgagagcg    3300
aggaggttgg agagagcacc gaggagcagg aagatgctcc cagatcagtc ctgggcagag    3360
tgaaaatatt cgagaagatg gaccacaagg caaaattaca gaggatgcag gagctccagg    3420
aggcccagaa tgcgaggatc gaaatagctc agaagcaccc tgacatctat gcggttccaa    3480
tcaaggcccc caagccagat gctggcctcc ccccgcacat gagttctaga cccccagagc    3540
cccagaaagc tccttccaga ctttaccagg acaccagagg aagctacggc agtgaccccg    3600
aggaggagga gtaccgccag cagttggcag cacactcgaa gcgtggttac tacagccagc    3660
cctcccggta ccgagacacg gagttataga gcttgtatgc gtggactcct gcgaggccac    3720
ctggagatct tctccagtta aaacgcactg cagagatacg gtggggaccc aggcaacaga    3780
tggcatgagt tatcaactga aggctctgtt tgtgggactg gagtgaagtt gattctgact    3840
ttcttgaatg aagagaaaca gtctgataac tgttacttgc tttggtgtgg accaagatct    3900
gtattaacct ctctgtattt tttaatatgt atatcgagca ataactatct ttcctcactc    3960
gtggctgcct tcctgcacag cttcagtgtg aagcagatgt gaagagggag ttaaaaaaaa    4020
aaaaaaaaaa aggactccgt ctcagactaa gttcagaagt attttatcac gactctctaa    4080
gtgcctttga caaatgtgt ctcacgtttg cctccctccc tgacgcttca tgcaaaccca    4140
taatggacta aaactttatt ttgactaaat ttttatacca gtttagcagc tgtgactgcc    4200
cctgcaccat gccaccttt cagggcattg tctgtagtat tttccacaaa ttctgactgt    4260
acataggaca cgcaccctcg ggagtgtgtc tgcctatcaa ttctgcgtag ctcggaggcc    4320
aagattttag agtgtttgtc cgttgtctgg aaccacatat tccacaaagg cagagacttg    4380
agaaagggt attttgtttc ctctctatca gagtatgtac tgacatcggg tggttttgta    4440
atttaataaa aaggagtaca agaatgagtt tagtgctgag tctctacaca ccttccttct    4500
gggcagtgtg gggggaaccc aaggtcctca tgcattcaga gtgctgcttc accactgaac    4560
tacaccccac tcttcctgat ttattttaat taaaaaaatt tttaaaaga caaaaaaaaa    4620
aaaaaaa                                                              4627
```

<210> SEQ ID NO 4
<211> LENGTH: 4725
<212> TYPE: DNA
<213> ORGANISM: Artificial Sequence
<220> FEATURE:
<223> OTHER INFORMATION: A synthetic tight Junction Protein 2 (ZO-2)
      isoform 1 of Homo sapiens

<400> SEQUENCE: 4

```
gacgcggttc gccgcaggag cctcgaaggc gcggcgccgg cgagcccttc cccggcaggc     60
gcgtgggtgg tagcggccaa tttgacagtt tcccgggccg ggcggccagc gcggaggcgc    120
cacgctcggg tcggggggcgg gctgacgccg ccgccgccgc gggaggaggg acaaagggt    180
gggtccccgc gggtcggcac cccggcggtt gggctgcggt tcagagcact gtccggtggt    240
gcccaggagg agtaggagca ggagcagaag cagaagcggg gtccggagct gcgcgcctac    300
gcgggacctg tgtccgaaat gccggtgcga ggagaccgcg ggtttccacc ccggcgggag    360
ctgtcaggtt ggctccgcgc cccaggcatg gaagagctga tatgggaaca gtacactgtg    420
```

-continued

```
accctacaaa aggattccaa aagaggattt ggaattgcag tgtccggagg cagagacaac    480
ccccactttg aaaatggaga aacgtcaatt gtcatttctg atgtgctccc gggtgggcct    540
gctgatgggc tgctccaaga aaatgacaga gtggtcatgg tcaatggcac ccccatggag    600
gatgtgcttc attcgtttgc agttcagcag ctcagaaaaa gtgggaaggt cgctgctatt    660
gtggtcaaga ggccccggaa ggtccaggtg gccgcacttc aggccagccc tccctggat    720 caggatgacc gggcttttga ggtgatggac gagtttgatg cagaagtttc cggagtggc    780 tacagcgaga ggagccggct gaacagccat gggggcgca gccgcagctg gaggacagc    840 ccggaaaggg ggcgtcccca tgagcgggcc cggagccggg agcgggacct cagccgggac    900
cggagccgtg gccggagcct ggagcggggc ctggaccaag accatgcgcg cacccgagac    960
cgcagccgtg gccggagcct ggagcggggc ctggaccacg actttgggcc atcccgggac   1020
cgggaccgtg accgcagccg cggccggagc attgaccagg actacgagcg agcctatcac   1080
cgggcctacg acccagacta cgagcgggcc tacagcccgg agtacaggcg cggggccccgc  1140 cacgatgccc gctctcgggg accccgaagc cgcagccgcg agcacccgca ctcacggagc   1200
cccagccccg agcctagggg gcggccgggg cccatcgggg tcctcctgat gaaaagcaga   1260
gcgaacgaag agtatggtct ccggcttggg agtcagatct tcgtaaagga aatgacccga   1320
acgggtctgg caactaaaga tggcaacctt cacgaaggag ataattct caagatcaat    1380 gggactgtaa ctgagaacat gtctttaacg atgctcgaa aattgataga aaagtcaaga   1440
ggaaaactac agctagtggt gttgagagac agccagcaga ccctcatcaa catcccgtca   1500
ttaaatgaca gtgactcaga atagaagat atttcagaaa tagagtcaaa ccgatcattt    1560
tctccagagg agagacgtca tcagtattct gattatgatt atcattcctc aagtgagaag   1620
ctgaaggaaa ggccaagttc cagagaggac acgccgagca gattgtccag gatgggtgcg   1680
acacccactc cctttaagtc cacaggggat attgcaggca cagttgtccc agagaccaac   1740
aaggaaccca gataccaaga ggaccccccca gctcctcaac caaaagcagc cccgagaact   1800
tttcttcgtc ctagtcctga agatgaagca atatatggcc ctaataccaa aatggtaagg   1860
ttcaagaagg gagacagcgt gggcctccgg ttggctggtg gcaatgatgt cgggatattt   1920
gttgctggca ttcaagaagg gacctcggcg gagcaggagg gccttcaaga aggagaccag   1980
attctgaagg tgaacacaca ggatttcaga ggattagtgc gggaggatgc cgttctctac   2040
ctgttagaaa tccctaaagg tgaaatggtg accattttag ctcagagccg agccgatgtg   2100
tatagagaca tcctggcttg tgcagagggg gattcgtttt ttataagaag ccactttgaa   2160
tgtgagaagg aaactccaca gagcctggcc ttcaccagag gggaggtctt ccgagtggta   2220
gacacactgt atgacggcaa gctgggcaac tggctggctg tgaggattgg gaacgagttg   2280
gagaaaggct taatccccaa caagagcaga gctgaacaaa tggccagtgt tcaaaatgcc   2340
cagagagaca cgctgggga ccgggcagat ttctggagaa tgcgtggcca gaggtctggg   2400
gtgaagaaga acctgaggaa aagtcgggaa gacctcacag ctgttgtgtc tgtcagcacc   2460
aagttcccag cttatgagag ggttttgctg cgagaagctg gtttcaagag acctgtggtc   2520
ttattcggcc ccatagctga tatagcaatg gaaaaattgg ctaatgagtt acctgactgg   2580
tttcaaactg ctaaaacgga accaaaagat gcaggatctg agaaatccac tggagtggtc   2640
cggttaaata ccgtgaggca aattattgaa caggataagc atgcactact ggatgtgact   2700
ccgaaagctg tggacctgtt gaattacacc cagtggttcc caattgtgat ttttttcaac   2760
ccagactcca gacaaggtgt caaaaccatg agacaaaggt taaatccaac gtccaacaaa   2820
```

```
agttctcgaa agttatttga tcaagccaac aagcttaaaa aaacgtgtgc acacctttt      2880 acagctacaa tcaacctaaa ttcagccaat gatagctggt ttggcagctt aaaggacact    2940
attcagcatc agcaaggaga agcggtttgg gtctctgaag gaaagatgga agggatggat    3000
gatgaccccg aagaccgcat gtcctactta accgccatgg gcgcggacta tctgagttgc    3060
gacagccgcc tcatcagtga cttttgaagac acggacggtg aaggaggcgc ctacactgac   3120
aatgagctgg atgagccagc cgaggagccg ctggtgtcgt ccatcacccg ctcctcggag    3180
ccggtgcagc acgaggagag cataaggaaa cccagcccag agccacgagc tcagatgagg    3240
agggctgcta gcagcgatca acttaggggac aatagcccgc ccccagcatt caagccagag   3300
ccgcccaagg ccaaaaccca gaacaaagaa gaatcctatg acttctccaa atcctatgaa    3360
tataagtcaa accctctgc cgttgctggt aatgaaactc ctggggcatc taccaaaggt     3420
tatcctcctc ctgttgcagc aaaacctacc tttgggcggt ctatactgaa gccctccact    3480
cccatccctc ctcaagaggg tgaggaggtg ggagagagca gtgaggagca agataatgct    3540
cccaaatcag tcctgggcaa agtcaaaata tttgagaaga tggatcacaa ggccaggtta    3600
cagagaatgc aggagctcca ggaagcacag aatgcaagga tcgaaattgc ccagaagcat    3660
cctgatatct atgcagttcc aatcaaaacg cacaagccag accctggcac gccccagcac    3720
acgagttcca gaccccctga gccacagaaa gctccttcca gaccttatca ggataccaga    3780
ggaagttatg gcagtgatgc cgaggaggag gagtaccgcc agcagctgtc agaacactcc    3840
aagcgcggtt actatggcca gtctgcccga taccgggaca cagaattata gatgtctgag    3900
cacggactct cccaggcctg cctgcatggc atcagactag ccactcctgc caggccgccg    3960
ggatggttct tctccagtta gaatgcacca tggagacgtg gtgggactcc agctcgtgtg    4020
tcctcatgga gaacccaggg gacagctggt gcaaattcag aactgagggc tctgtttgtg   4080
ggactgggtt agaggagtct gtggcttttt gttcagaatt aagcagaaca ctgcagtcag   4140
atcctgttac ttgcttcagt ggaccgaaat ctgtattctg tttgcgtact tgtaatatgt   4200
atattaagaa gcaataacta ttttccctca ttaatagctg ccttcaagga ctgtttcagt   4260
gtgagtcaga atgtgaaaaa ggaataaaaa atactgttgg gctcaaacta aattcaaaga   4320
agtactttat tgcaactctt ttaagtgcct tggatgagaa gtgtcttaaa ttttcttcct   4380
ttgaagcttt aggcagagcc ataatggact aaaacatttt gactaagttt ttataccagc   4440
ttaatagctg tagttttccc tgcactgtgt catcttttca aggcatttgt ctttgtaata   4500
ttttccataa atttggactg tctatatcat aactatactt gatagtttgg ctataagtgc   4560
tcaatagctt gaagcccaag aagttggtat cgaaatttgt tgtttgttta aacccaagtg   4620
ctgcacaaaa gcagatactt gaggaaaaca ctatttccaa aagcacatgt attgacaaca   4680
gttttataat ttaataaaaa ggaatacatt gcaatccgta atttt                   4725
```

<210> SEQ ID NO 5
<211> LENGTH: 4284
<212> TYPE: DNA
<213> ORGANISM: Artificial Sequence
<220> FEATURE:
<223> OTHER INFORMATION: A synthetic tight Junction Protein 2 (ZO-2)
      isoform 2 of Homo sapiens

<400> SEQUENCE: 5

```
gacgcggttc gccgcaggag cctcgaaggc gcggcgccgg cgagcccttc cccggcaggc       60
gcgtgggtgg tagcggccaa tttgacagtt tcccgggccg ggcggccagc gcggaggcgc      120
```

| | |
|---|---:|
| cacgctcggg tcggggcgg gctgacgccg ccgccgccgc gggaggaggg acaaaggggt | 180 |
| gggtccccgc gggtcggcac cccggcggtt ggctgcggg tcagagcact gtccggtggt | 240 |
| gcccaggagg agtaggagca ggagcagaag cagaagcggg gtccggagct gcgcgcctac | 300 |
| gcgggacctg tgtccgaaat gccggtgcga ggagaccgcg ggtttccacc ccggcgggag | 360 |
| ctgtcaggtt ggctccgcgc cccaggcatg gaagagctga tatgggaaca gtacactgtg | 420 |
| accctacaaa aggattccaa aagaggattt ggaattgcag tgtccggagg cagagacaac | 480 |
| ccccactttg aaaatggaga aacgtcaatt gtcatttctg atgtgctccc gggtgggcct | 540 |
| gctgatgggc tgctccaaga aaatgacaga gtggtcatgg tcaatggcac ccccatggag | 600 |
| gatgtgcttc attcgtttgc agttcagcag ctcagaaaaa gtgggaaggt cgctgctatt | 660 |
| gtggtcaaga ggccccggaa ggtccaggtg gccgcacttc aggccagccc tcccctggat | 720 |
| caggatgacc gggcttttga ggtgatggac gagtttgatg cagaagtttt ccggagtggc | 780 |
| tacagcgaga ggagccggct gaacagccat ggggggcgca gccgcagctg gaggacagc | 840 |
| ccggaaaggg ggcgtcccca tgagcgggcc cggagccggg agcgggacct cagccgggac | 900 |
| cggagccgtg gccggagcct ggagcggggc ctggaccaag accatgcgcg cacccgagac | 960 |
| cgcagccgtg gccggagcct ggagcggggc ctggaccacg actttgggcc atcccgggac | 1020 |
| cgggaccgtg accgcagccg cggccggagc attgaccagg actacgagcg agcctatcac | 1080 |
| cgggcctacg acccagacta cgagcgggcc tacagcccgg agtacaggcg cggggcccgc | 1140 |
| cacgatgccc gctctcgggg accccgaagc cgcagccgcg agcacccgca ctcacggagc | 1200 |
| cccagccccg agcctagggg gcggccgggg cccatcgggg tcctcctgat gaaaagcaga | 1260 |
| gcgaacgaag agtatggtct ccggcttggg agtcagatct tcgtaaagga aatgaccccga | 1320 |
| acgggtctgg caactaaaga tggcaacctt cacgaaggag acataattct caagatcaat | 1380 |
| gggactgtaa ctgagaacat gtctttaacg gatgctcgaa aattgataga aaagtcaaga | 1440 |
| ggaaaactac agctagtggt gttgagagac agccagcaga ccctcatcaa catcccgtca | 1500 |
| ttaaatgaca gtgactcaga aatagaagat atttcagaaa tagagtcaaa ccgatcattt | 1560 |
| tctccagagg agagacgtca tcagtattct gattatgatt atcattcctc aagtgagaag | 1620 |
| ctgaaggaaa ggccaagttc cagagaggac acgccgagca gattgtccag gatgggtgcg | 1680 |
| acacccactc cctttaagtc cacagggga ttgcaggca cagttgtccc agagaccaac | 1740 |
| aaggaaccca gataccaaga ggacccccca gctcctcaac caaaagcagc cccgagaact | 1800 |
| tttcttcgtc ctagtcctga agatgaagca atatatggcc ctaataccaa aatggtaagg | 1860 |
| ttcaagaagg gagacagcgt gggcctccgg ttggctggtg gcaatgatgt cgggatattt | 1920 |
| gttgctggca ttcaagaagg gacctcgcg gagcaggagg ccttcaagaa aggagaccag | 1980 |
| attctgaagg tgaacacaca ggatttcaga ggattagtgc gggaggatgc cgttctctac | 2040 |
| ctgttagaaa tccctaaagg tgaaatggtg accattttag ctcagagccg agccgatgtg | 2100 |
| tatagagaca tcctggcttg tggcagaggg gattcgtttt ttataagaag ccactttgaa | 2160 |
| tgtgagaagg aaactccaca gagcctggcc ttcaccagag gggaggtctt ccgagtggta | 2220 |
| gacacactgt atgacggcaa gctgggcaac tggctggctg tgaggattgg gaacgagttg | 2280 |
| gagaaaggct taatccccaa caagagcaga gctgaacaaa tggccagtgt tcaaaatgcc | 2340 |
| cagagagaca cgctgggga ccgggcagat ttctggagaa tgcgtggcca gaggtctggg | 2400 |
| gtgaagaaga acctgaggaa aagtcgggaa gacctcacag ctgttgtgtc tgtcagcacc | 2460 |

| aagttcccag cttatgagag ggttttgctg cgagaagctg gtttcaagag acctgtggtc | 2520 |
| ttattcggcc ccatagctga tatagcaatg gaaaaattgg ctaatgagtt acctgactgg | 2580 |
| tttcaaactg ctaaaacgga accaaaagat gcaggatctg agaaatccac tggagtggtc | 2640 |
| cggttaaata ccgtgaggca aattattgaa caggataagc atgcactact ggatgtgact | 2700 |
| ccgaaagctg tggacctgtt gaattacacc cagtggttcc caattgtgat ttttttcaac | 2760 |
| ccagactcca gacaaggtgt caaaaccatg agacaaaggt taaatccaac gtccaacaaa | 2820 |
| agttctcgaa agttatttga tcaagccaac aagcttaaaa aaacgtgtgc acaccttttt | 2880 |
| acagctacaa tcaacctaaa ttcagccaat gatagctggt ttggcagctt aaaggacact | 2940 |
| attcagcatc agcaaggaga agcggtttgg gtctctgaag gaaagatgga agggatggat | 3000 |
| gatgaccccg aagaccgcat gtcctactta accgccatgg gcgcggacta tctgagttgc | 3060 |
| gacagccgcc tcatcagtga ctttgaagac acggacggtg aaggaggcgc ctacactgac | 3120 |
| aatgagctgg atgagccagc cgaggagccg ctggtgtcgt ccatcacccg ctcctcggag | 3180 |
| ccggtgcagc acgaggagat cgaaattgcc cagaagcatc ctgatatcta tgcagttcca | 3240 |
| atcaaaacgc acaagccaga ccctggcacg ccccagcaca cgagttccag accccctgag | 3300 |
| ccacagaaag ctccttccag accttatcag gataccagag gaagttatgg cagtgatgcc | 3360 |
| gaggaggagg agtaccgcca gcagctgtca gaacactcca agcgcggtta ctatggccag | 3420 |
| tctgcccgat accgggacac agaattatag atgtctgagc acggactctc ccaggcctgc | 3480 |
| ctgcatggca tcagactagc cactcctgcc aggccgccgg gatggttctt ctccagttag | 3540 |
| aatgcaccat ggagacgtgg tgggactcca gctcgtgtgt cctcatggag aacccagggg | 3600 |
| acagctggtg caaattcaga actgagggct ctgtttgtgg gactgggtta gaggagtctg | 3660 |
| tggcttttg ttcagaatta agcagaacac tgcagtcaga tcctgttact tgcttcagtg | 3720 |
| gaccgaaatc tgtattctgt ttgcgtactt gtaatatgta tattaagaag caataactat | 3780 |
| ttttcctcat taatagctgc cttcaaggac tgtttcagtg tgagtcagaa tgtgaaaaag | 3840 |
| gaataaaaaa tactgttggg ctcaaactaa attcaaagaa gtactttatt gcaactcttt | 3900 |
| taagtgcctt ggatgagaag tgtcttaaat tttcttcctt tgaagcttta ggcagagcca | 3960 |
| taatggacta aaacattttg actaagtttt tataccagct taatagctgt agttttccct | 4020 |
| gcactgtgtc atcttttcaa ggcatttgtc tttgtaatat tttccataaa tttggactgt | 4080 |
| ctatatcata actatacttg atagtttggc tataagtgct caatagcttg aagcccaaga | 4140 |
| agttggtatc gaaatttgtt gtttgtttaa acccaagtgc tgcacaaaag cagatacttg | 4200 |
| aggaaaacac tatttccaaa agcacatgta ttgacaacag ttttataatt taataaaaag | 4260 |
| gaatacattg caatccgtaa tttt | 4284 |

<210> SEQ ID NO 6
<211> LENGTH: 4500
<212> TYPE: DNA
<213> ORGANISM: Artificial Sequence
<220> FEATURE:
<223> OTHER INFORMATION: A synthetic tight Junction Protein 2 (ZO-2)
      isoform 3 of Homo sapiens

<400> SEQUENCE: 6

| atgaagactg ctcaagccct acataggatg tggatccagg ctgttaaaaa gttgaggaga | 60 |
| tggaaaggcc gtgtgagtcc ctctgcaagc tctccccttg ttttccccaa cctttcttca | 120 |
| tgggaagggg agggaagcaa aaccattctc acagccccag gcatggaaga gctgatatgg | 180 |

```
gaacagtaca ctgtgaccct acaaaaggat tccaaaagag gatttggaat tgcagtgtcc      240
ggaggcagag acaaccccca ctttgaaaat ggagaaacgt caattgtcat ttctgatgtg      300
ctcccgggtg ggcctgctga tgggctgctc caagaaaatg acagagtggt catggtcaat      360
ggcaccccca tggaggatgt gcttcattcg tttgcagttc agcagctcag aaaaagtggg      420
aaggtcgctg ctattgtggt caagaggccc cggaaggtcc aggtggccgc acttcaggcc      480
agccctcccc tggatcagga tgaccgggct tttgaggtga tggacgagtt tgatggcaga      540
agtttccgga gtggctacag cgagaggagc cggctgaaca gccatggggg gcgcagccgc      600
agctgggagg acagcccgga aagggggcgt ccccatgagc gggcccggag ccggagcgg      660 gacctcagcc gggaccggag ccgtggccgg agcctggagc ggggcctgga ccaagaccat      720
gcgcgcaccc gagaccgcag ccgtggccgg agcctggagc ggggcctgga ccacgacttt      780
gggccatccc gggaccggga ccgtgaccgc agccgcggcc ggagcattga ccaggactac      840
gagcgagcct atcaccgggc ctacgaccca gactacgagc gggcctacag cccggagtac      900
aggcgcgggg cccgccacga tgcccgctct cggggacccc gaagccgcag ccgcgagcac      960
ccgcactcac ggagcccag ccccgagcct aggggggcggc cggggcccat cggggtcctc      1020
ctgatgaaaa gcagagcgaa cgaagagtat ggtctccggc ttgggagtca gatcttcgta      1080
aaggaaatga cccgaacggg tctggcaact aaagatggca accttcacga aggagacata      1140
attctcaaga tcaatgggac tgtaactgag aacatgtctt taacggatgc tcgaaaattg      1200
atagaaaagt caagaggaaa actacagcta gtggtgttga gagacagcca gcagaccctc      1260
atcaacatcc cgtcattaaa tgacagtgac tcagaaatag aagatatttc agaaatagag      1320
tcaaaccgat cattttctcc agaggagaga cgtcatcagt attctgatta tgattatcat      1380
tcctcaagtg agaagctgaa ggaaaggcca agttccagag gagacacgcc gagcagattg      1440
tccaggatgg gtgcgacacc cactcccttt aagtccacag gggatattgc aggcacagtt      1500
gtcccagaga ccaacaagga acccagatac caagaggacc ccccagctcc tcaaccaaaa      1560
gcagccccga gaactttttct tcgtcctagt cctgaagatg aagcaatata tggccctaat      1620
accaaaatgg taaggttcaa gaagggagac agcgtgggcc tccggttggc tggtggcaat      1680
gatgtcggga tatttgttgc tggcattcaa gaagggacct cggcggagca ggagggcctt      1740
caagaaggag accagattct gaaggtgaac acacaggatt tcagaggatt agtgcgggag      1800
gatgccgttc tctacctgtt agaaatccct aaaggtgaaa tggtgaccat tttagctcag      1860
agccgagccg atgtgtatag agacatcctg cttgtggca gagggattc gttttttata      1920 agaagccact ttgaatgtga aaggaaaact ccacagagcc tggccttcac cagaggggag      1980
gtcttccgag tggtagacac actgtatgac ggcaagctgg gcaactggct ggctgtgagg      2040
attgggaacg agttggagaa aggcttaatc cccaacaaga gcagagctga acaaatggcc      2100
agtgttcaaa atgcccagag agacaacgct ggggaccggg cagatttctg gagaatgcgt      2160
ggccagaggt ctggggtgaa gaagaacctg aggaaaagtc gggaagacct cacagctgtt      2220
gtgtctgtca gcaccaagtt cccagcttat gagagggttt tgctgcgaga gctggtttc      2280 aagagacctg tggtcttatt cggccccata gctgatatag caatgaaaa attggctaat      2340 gagttacctg actggtttca aactgctaaa acggaaccaa aagatgcagg atctgagaaa      2400
tccactggag tggtccggtt aaataccgtg aggcaaatta ttgaacagga taagcatgca      2460
ctactggatg tgactccgaa agctgtggac ctgttgaatt acacccagtg gttcccaatt      2520
gtgatttttt tcaacccaga ctccagacaa ggtgtcaaaa ccatgagaca aaggttaaat      2580
```

```
ccaacgtcca acaaaagttc tcgaaagtta tttgatcaag ccaacaagct taaaaaaacg    2640
tgtgcacacc ttttacagc tacaatcaac ctaaattcag ccaatgatag ctggtttggc    2700
agcttaaagg acactattca gcatcagcaa ggagaagcgg tttgggtctc tgaaggaaag    2760
atggaaggga tggatgatga ccccgaagac cgcatgtcct acttaaccgc catgggcgcg    2820
gactatctga gttgcgacag ccgcctcatc agtgactttg aagacacgga cggtgaagga    2880
ggcgcctaca ctgacaatga gctggatgag ccagccgagg agccgctggt gtcgtccatc    2940
acccgctcct cggagccggt gcagcacgag gagagcataa ggaaacccag cccagagcca    3000
cgagctcaga tgaggagggc tgctagcagc gatcaactta gggacaatag cccgccccca    3060
gcattcaagc cagagccgcc caaggccaaa acccagaaca agaagaatc ctatgacttc    3120 tccaaatcct atgaatataa gtcaaacccc tctgccgttg ctggtaatga aactcctggg    3180
gcatctacca aaggttatcc tcctcctgtt gcagcaaaac ctacctttgg gcggtctata    3240
ctgaagccct ccactcccat ccctcctcaa gagggtgagg aggtgggaga gagcagtgag    3300
gagcaagata atgctcccaa atcagtcctg ggcaaagtca aatatttga agatggat    3360 cacaaggcca ggttacagag aatgcaggag ctccaggaag cacagaatgc aaggatcgaa    3420
attgcccaga agcatcctga tatctatgca gttccaatca aaacgcacaa gccagaccct    3480
ggcacgcccc agcacacgag ttccagaccc cctgagccac agaaagctcc ttccagacct    3540
tatcaggata ccagaggaag ttatggcagt gatgccgagg aggaggagta ccgccagcag    3600
ctgtcagaac actccaagcg cggttactat ggccagtctg cccgataccg ggacacagaa    3660
ttatagatgt ctgagcacgg actctcccag gcctgcctgc atggcatcag actagccact    3720
cctgccaggc cgccgggatg gttcttctcc agttagaatg caccatggag acgtggtggg    3780
actccagctc gtgtgtcctc atggagaacc caggggacag ctggtgcaaa ttcagaactg    3840
agggctctgt ttgtgggact gggttagagg agtctgtggc tttttgttca gaattaagca    3900
gaacactgca gtcagatcct gttacttgct tcagtggacc gaaatctgta ttctgtttgc    3960
gtacttgtaa tatgtatatt aagaagcaat aactatttt cctcattaat agctgccttc    4020
aaggactgtt tcagtgtgag tcagaatgtg aaaaaggaat aaaaaatact gttgggctca    4080
aactaaattc aaagaagtac tttattgcaa ctcttttaag tgccttggat gagaagtgtc    4140 ttaaatttc ttccttttgaa gctttaggca gagccataat ggactaaaac attttgacta    4200 agttttata ccagcttaat agctgtagtt ttccctgcac tgtgtcatct tttcaaggca    4260
tttgtctttg taatatttc cataaatttg gactgtctat atcataacta tacttgatag    4320
tttggctata agtgctcaat agcttgaagc ccaagaagtt ggtatcgaaa tttgttgttt    4380
gtttaaaccc aagtgctgca caaaagcaga tacttgagga aaacactatt tccaaaagca    4440
catgtattga caacagttt ataattaat aaaaaggaat acattgcaat ccgtaatttt    4500
```

<210> SEQ ID NO 7
<211> LENGTH: 4459
<212> TYPE: DNA
<213> ORGANISM: Artificial Sequence
<220> FEATURE:
<223> OTHER INFORMATION: A synthetic tight Junction Protein 2 (ZO-2)
      isoform 4 of Homo sapiens

<400> SEQUENCE: 7

```
atatggatgt gtcactgtgt gagatgacaa caggatttgc tggaaatgtg ggccactatt      60
gtatccgcct tacgtaacca catggagtga tggaaatggg tgagcagccc ggaatgtagg     120
```

```
cggtggcctg gcccatgcat ctccagagac catgaagact gctcaagccc tacataggat    180
gtggatccag gctgttaaaa agttgaggag atggaaaggc cgtgcccag gcatggaaga     240 gctgatatgg gaacagtaca ctgtgaccct acaaaaggat tccaaaagag gatttggaat   300
tgcagtgtcc ggaggcagag acaaccccca ctttgaaaat ggagaaacgt caattgtcat    360
ttctgatgtg ctcccgggtg ggcctgctga tgggctgctc caagaaaatg acagagtggt    420
catggtcaat ggcaccccca tggaggatgt gcttcattcg tttgcagttc agcagctcag    480
aaaaagtggg aaggtcgctg ctattgtggt caagaggccc cggaaggtcc aggtggccgc    540
acttcaggcc agccctcccc tggatcagga tgaccgggct tttgaggtga tggacgagtt    600
tgatggcaga agtttccgga gtggctacag cgagaggagc cggctgaaca gccatggggg    660
gcgcagccgc agctgggagg acagcccgga aaggggcgt ccccatgagc gggcccggag     720
ccgggagcgg gacctcagcc gggaccggag ccgtggccgg agcctggagc ggggcctgga    780
ccaagaccat gcgcgcaccc gagaccgcag ccgtggccgg agcctggagc ggggcctgga    840
ccacgacttt gggccatccc gggaccggga ccgtgaccgc agccgcggcc ggagcattga    900
ccaggactac gagcgagcct atcaccgggc ctacgaccca gactacgagc gggcctacag    960
cccggagtac aggcgcgggg cccgccacga tgcccgctct cggggacccc gaagccgcag   1020
ccgcgagcac ccgcactcac ggagcccag ccccgagcct aggggggcggc cggggcccat    1080 cggggtcctc ctgatgaaaa gcagagcgaa cgaagagtat ggtctccggc ttgggagtca   1140
gatcttcgta aaggaaatga cccgaacggg tctggcaact aaagatggca accttcacga   1200
aggagacata attctcaaga tcaatgggac tgtaactgag aacatgtctt taacggatgc   1260
tcgaaaattg atagaaaagt caagaggaaa actacagcta gtggtgttga gagacagcca   1320
gcagaccctc atcaacatcc cgtcattaaa tgacagtgac tcagaaatag aagatatttc   1380
agaaatagag tcaaaccgat cattttctcc agaggagaga cgtcatcagt attctgatta   1440
tgattatcat tcctcaagtg agaagctgaa ggaaaggcca agttccagag aggacacgcc   1500
gagcagattg tccaggatgg gtgcgacacc cactcccttt aagtccacag gggatattgc   1560
aggcacagtt gtcccagaga ccaacaagga acccagatac caagaggacc ccccagctcc   1620
tcaaccaaaa gcagccccga gaacttttct tcgtcctagt cctgaagatg aagcaatata   1680
tggccctaat accaaaatgg taaggttcaa gaagggagac agcgtgggcc tccggttggc   1740
tggtggcaat gatgtcggga tatttgttgc tggcattcaa gaagggacct cggcggagca   1800
ggagggcctt caagaaggag accagattct gaaggtgaac acacaggatt tcagaggatt   1860
agtgcgggag gatgccgttc tctacctgtt agaaatccct aaaggtgaaa tggtgaccat   1920
tttagctcag agccgagccg atgtgtatag agacatcctg gcttgtggca gaggggattc   1980
gttttttata agaagccact ttgaatgtga aaggaaaact ccacagagcc tggccttcac   2040
cagaggggag gtcttccgag tggtagacac actgtatgac ggcaagctgg gcaactggct   2100
ggctgtgagg attgggaacg agttggagaa aggcttaatc cccaacaaga gcagagctga   2160
acaaatggcc agtgttcaaa atgcccagag agacaacgct ggggaccggg cagatttctg   2220
gagaatgcgt ggccagaggt ctgggggtgaa aagaacctg aggaaaagtc gggaagacct    2280
cacagctgtt gtgtctgtca gcaccaagtt cccagcttat gagagggttt gctgcgaga    2340 agctggtttc aagagacctg tggtcttatt cggccccata gctgatatag caatggaaaa   2400
attggctaat gagttacctg actggtttca aactgctaaa acggaaccaa agatgcagg    2460
```

```
atctgagaaa tccactggag tggtccggtt aaataccgtg aggcaaatta ttgaacagga    2520
taagcatgca ctactggatg tgactccgaa agctgtggac ctgttgaatt acacccagtg    2580
gttcccaatt gtgattttt tcaacccaga ctccagacaa ggtgtcaaaa ccatgagaca    2640
aaggttaaat ccaacgtcca acaaaagttc tcgaaagtta tttgatcaag ccaacaagct    2700
taaaaaaacg tgtgcacacc tttttacagc tacaatcaac ctaaattcag ccaatgatag    2760
ctggtttggc agcttaaagg acactattca gcatcagcaa ggagaagcgg tttgggtctc    2820
tgaaggaaag atggaaggga tggatgatga ccccgaagac cgcatgtcct acttaaccgc    2880
catgggcgcg gactatctga gttgcgacag ccgcctcatc agtgactttg aagcacggga    2940
cggtgaagga ggcgcctaca ctgacaatga gctggatgag ccagccgagg agccgctggt    3000
gtcgtccatc acccgctcct cggagccggt gcagcacgag gaggccaaaa cccagaacaa    3060
agaagaatcc tatgacttct ccaaatccta tgaatataag tcaaaccccct ctgccgttgc    3120 tggtaatgaa actcctgggg catctaccaa aggttatcct cctcctgttg cagcaaaacc    3180
tacctttggg cggtctatac tgaagccctc cactcccatc cctcctcaag agggtgagga    3240
ggtgggagag agcagtgagg agcaagataa tgctcccaaa tcagtcctgg gcaaagtcaa    3300
aatatttgag aagatggatc acaaggccag gttacagaga atgcaggagc tccaggaagc    3360
acagaatgca aggatcgaaa ttgcccagaa gcatcctgat atctatgcag ttccaatcaa    3420
aacgcacaag ccagaccctg gcacgcccca gcacacgagt tccagacccc ctgagccaca    3480
gaaagctcct tccagacctt atcaggatac cagaggaagt tatggcagtg atgccgagga    3540
ggaggagtac cgccagcagc tgtcagaaca ctccaagcgc ggttactatg ccagtctgc    3600 ccgataccgg gacacagaat tatagatgtc tgagcacgga ctctcccagg cctgcctgca    3660
tggcatcaga ctagccactc ctgccaggcc gccgggatgg ttcttctcca gttagaatgc    3720
accatggaga cgtggtggga ctccagctcg tgtgtcctca tggagaaccc aggggacagc    3780
tggtgcaaat tcagaactga gggctctgtt tgtgggactg ggttagagga gtctgtggct    3840 tttttgttcag aattaagcag aacactgcag tcagatcctg ttacttgctt cagtggaccg    3900
aaatctgtat tctgtttgcg tacttgtaat atgtatatta agaagcaata actattttc    3960 ctcattaata gctgccttca aggactgttt cagtgtgagt cagaatgtga aaaaggaata    4020
aaaaatactg ttgggctcaa actaaattca agaagtact ttattgcaac tcttttaagt    4080
gccttggatg agaagtgtct taaattttct tccttgaag ctttaggcag agccataatg    4140
gactaaaaca ttttgactaa gtttttatac cagcttaata gctgtagttt tccctgcact    4200
gtgtcatctt ttcaaggcat ttgtctttgt aatattttcc ataaattggg actgtctata    4260
tcataactat acttgatagt ttggctataa gtgctcaata gcttgaagcc caagaagttg    4320
gtatcgaaat ttgttgtttg tttaaaccca agtgctgcac aaaagcagat acttgaggaa    4380
aacactattt ccaaaagcac atgtattgac aacagtttta taatttaata aaaaggaata    4440
cattgcaatc cgtaatttt                                                 4459
```

<210> SEQ ID NO 8
<211> LENGTH: 4129
<212> TYPE: DNA
<213> ORGANISM: Artificial Sequence
<220> FEATURE:
<223> OTHER INFORMATION: A synthetic tight Junction Protein 2 (ZO-2)
      isoform 5 of Homo sapiens

<400> SEQUENCE: 8

-continued

```
caccctctcc gcctttcccg acaccccaaa gtagcgctgc gagcagctgc gtctccctcc      60
cggggctcgc gcgcccagaa ccctccggtc tcaaggaagc agggtgcgaa gtaccacatt     120
actgtcatct ccctgtgagt gggattggca ccccggctgc agctccagga gcaagtactc     180
caggaagcac agagctgtac cagtacacgg cccacgttgc caggcccag gcatggaaga      240 gctgatatgg aacagtaca ctgtgaccct acaaaaggat tccaaaagag gatttggaat      300
tgcagtgtcc ggaggcagag acaaccccca ctttgaaaat ggagaaacgt caattgtcat     360
ttctgatgtg ctcccgggtg ggcctgctga tgggctgctc caagaaaatg acagagtggt     420
catggtcaat gcaccccca tggaggatgt gcttcattcg tttgcagttc agcagctcag      480
aaaaagtggg aaggtcgctg ctattgtggt caagaggccc cggaaggtcc aggtggccgc     540
acttcaggcc agccctcccc tggatcagga tgaccgggct tttgaggtga tggacgagtt     600
tgatggcaga agtttccgga gtggctacag cgagaggagc cggctgaaca gccatggggg     660
gcgcagccgc agctgggagg acagcccgga aggggcgt ccccatgagc gggcccggag       720
ccgggagcgg gacctcagcc gggaccggag ccgtggccgg agcctggagc gggccctgga    780
ccaagaccat gcgcgcaccc gagaccgcag ccgtggccgg agcctggagc gggccctgga    840
ccacgacttt gggccatccc gggaccggga ccgtgaccgc agccgcggcc ggagcattga     900
ccaggactac gagcgagcct atcaccgggc ctacgaccca gactacgagc gggcctacag     960 cccgagtac aggcgcgggg cccgccacga tgcccgctct cggggacccc gaagccgcag     1020
ccgcgagcac ccgcactcac ggagccccag ccccgagcct aggggggcggc cggggcccat    1080 cggggtcctc ctgatgaaaa gcagagcgaa cgaagagtat ggtctccggc ttgggagtca    1140
gatcttcgta aaggaaatga cccgaacggg tctggcaact aaagatggca accttcacga    1200
aggagacata attctcaaga tcaatgggac tgtaactgag aacatgtctt taacggatgc    1260
tcgaaaattg atagaaaagt caagaggaaa actacagcta gtggtgttga gagacagcca    1320
gcagaccctc atcaacatcc cgtcattaaa tgacagtgac tcagaaatag aagatatttc    1380
agaaatagag tcaaaccgat cattttctcc agaggagaga cgtcatcagt attctgatta    1440
tgattatcat tcctcaagtg agaagctgaa ggaaaggcca agttccagag aggacacgcc    1500
gagcagattg tccaggatgg gtgcgacacc cactcccttt aagtccacag gggatattgc    1560
aggcacagtt gtcccagaga ccaacaagga acccagatac caagaggacc ccccagctcc    1620
tcaaccaaaa gcagccccga aacttttct tcgtcctagt cctgaagatg aagcaatata    1680 tggcccctaat accaaaatgg taaggttcaa gaagggagac agcgtggggcc tccggttggc   1740 tggtggcaat gatgtcggga tatttgttgc tggcattcaa gaagggacct cggcggagca    1800
ggagggcctt caagaaggag accagattct gaaggtgaac acacaggatt tcagaggatt    1860
agtgcgggag gatgccgttc tctacctgtt agaaatccct aaaggtgaaa tggtgaccat    1920
tttagctcag agccgagccg atgtgtatag agacatcctg gcttgtggca gggggattc     1980 gttttttata agaagccact ttgaatgtga gaaggaaact ccacagagcc tggccttcac    2040
cagaggggag gtcttccgag tggtagacac actgtatgac ggcaagctgg gcaactggct   2100
ggctgtgagg attgggaacg agttggagaa aggcttaatc cccaacaaga gcagagctga    2160
acaaatggcc agtgttcaaa atgcccagag agacaacgct ggggaccggg cagatttctg    2220
gagaatgcgt ggccagaggt ctggggtgaa gaagaacctg aggaaaagtc gggaagacct    2280
cacagctgtt gtgtctgtca gcaccaagtt cccagcttat gagagggttt tgctgcgaga    2340
agctggtttc aagagacctg tggtcttatt cggcccata gctgatatag caatggaaaa     2400
```

```
attggctaat gagttacctg actggtttca aactgctaaa acggaaccaa aagatgcagg    2460
atctgagaaa tccactggag tggtccggtt aaataccgtg aggcaaatta ttgaacagga    2520
taagcatgca ctactggatg tgactccgaa agctgtggac ctgttgaatt acacccagtg    2580
gttcccaatt gtgatttttt tcaacccaga ctccagacaa ggtgtcaaaa ccatgagaca    2640
aaggttaaat ccaacgtcca acaaaagttc tcgaaagtta tttgatcaag ccaacaagct    2700
taaaaaaacg tgtgcacacc ttttacagc tacaatcaac ctaaattcag ccaatgatag     2760
ctggtttggc agcttaaagg acactattca gcatcagcaa ggagaagcgg tttgggtctc    2820
tgaaggaaag atggaaggga tggatgatga ccccgaagac cgcatgtcct acttaaccgc    2880
catgggcgcg gactatctga gttgcgacag ccgcctcatc agtgactttg aagacacgga    2940
cggtgaagga ggcgcctaca ctgacaatga gctggatgag ccagccgagg agccgctggt    3000
gtcgtccatc acccgctcct cggagccggt gcagcacgag gagatcgaaa ttgcccagaa    3060
gcatcctgat atctatgcag ttccaatcaa aacgcacaag ccagaccctg cacgccccca    3120
gcacacgagt tccagacccc ctgagccaca gaaagctcct tccagacctt atcaggatac    3180
cagaggaagt tatggcagtg atgccgagga ggaggagtac cgccagcagc tgtcagaaca    3240
ctccaagcgc ggttactatg ccagtctgc ccgataccgg gacacagaat tatagatgtc      3300
tgagcacgga ctctcccagg cctgcctgca tggcatcaga ctagccactc ctgccaggcc    3360
gccgggatgg ttcttctcca gttagaatgc accatggaga cgtggtggga ctccagctcg    3420
tgtgtcctca tggagaaccc aggggacagc tggtgcaaat tcagaactga gggctctgtt    3480
tgtgggactg ggttagagga gtctgtggct ttttgttcag aattaagcag aacactgcag    3540
tcagatcctg ttacttgctt cagtggaccg aaatctgtat tctgtttgcg tacttgtaat    3600
atgtatatta agaagcaata actattttc ctcattaata gctgccttca aggactgttt     3660
cagtgtgagt cagaatgtga aaaggaata aaaatactg ttgggctcaa actaaattca      3720
aagaagtact ttattgcaac tcttttaagt gccttggatg agaagtgtct taaattttct    3780
tcctttgaag ctttaggcag agccataatg gactaaaaca ttttgactaa gttttttatac   3840 cagcttaata gctgtagttt tccctgcact gtgtcatctt ttcaaggcat tgtctttgt     3900 aatattttcc ataaatttgg actgtctata tcataactat acttgatagt ttggctataa    3960
gtgctcaata gcttgaagcc caagaagttg gtatcgaaat ttgttgtttg tttaaaccca    4020
agtgctgcac aaaagcagat acttgaggaa aacactattt ccaaaagcac atgtattgac    4080 aacagttta taatttaata aaaggaata cattgcaatc cgtaattt                   4129
```

<210> SEQ ID NO 9
<211> LENGTH: 4720
<212> TYPE: DNA
<213> ORGANISM: Artificial Sequence
<220> FEATURE:
<223> OTHER INFORMATION: A synthetic tight Junction Protein 2 (ZO-2)
      isoform 6 of Homo sapiens

<400> SEQUENCE: 9

```
gacgcggttc gccgcaggag cctcgaaggc gcggcgccgg cgagcccttc cccggcaggc      60
gcgtgggtgg tagcggccaa tttgacagtt tcccggggccg ggcggccagc gcggaggcgc    120
cacgctcggg tcggggggcgg gctgacgccg ccgccgccgc gggaggaggg acaaagggt     180 gggtccccgc gggtcggcac cccggcggtt gggctgcggg tcagagcact gtccggtggt    240
gcccaggagg agtaggagca ggagcagaag cagaagcggg gtccggagct gcgcgcctac    300
```

```
gcgggacctg tgtccgaaat gccggtgcga ggagaccgcg ggtttccacc ccggcgggag    360
ctgtcaggtt ggctccgcgc cccaggcatg gaagagctga tatgggaaca gtacactgtg    420
accctacaaa aggattccaa aagaggattt ggaattgcag tgtccggagg cagagacaac    480
ccccactttg aaaatggaga acgtcaatt gtcatttctg atgtgctccc gggtgggcct     540
gctgatgggc tgctccaaga aaatgacaga gtggtcatgg tcaatggcac ccccatggag    600
gatgtgcttc attcgtttgc agttcagcag ctcagaaaaa gtgggaaggt cgctgctatt    660
gtggtcaaga ggccccggaa ggtccaggtg gccgcacttc aggccagccc tccctggat    720 caggatgacc gggcttttga ggtgatggac gagtttgatg cagaagttt ccggagtggc     780 tacagcgaga ggagccggct gaacagccat ggggggcgca gccgcagctg gaggacagc    840 ccggaaaggg ggcgtcccca tgagcgggcc ggagccggg agcgggacct cagccgggac    900
cggagccgtg gccggagcct ggagcggggc ctggaccaag accatgcgcg caccccgagac  960 cgcagccgtg gccggagcct ggagcggggc ctggaccacg actttgggcc atcccgggac   1020
cgggaccgtg accgcagccg cggccggagc attgaccagg actacgagcg agcctatcac   1080
cgggcctacg acccagacta cgagcgggcc tacagcccgg agtacaggcg cggggcccgc   1140
cacgatgccc gctctcgggg acccgaagc cgcagccgcg agcacccgca ctcacggagc    1200
cccagccccg agcctagggg gcggccgggg cccatcgggg tcctcctgat gaaaagcaga   1260
gcgaacgaag agtatggtct ccggcttggg agtcagatct tcgtaaagga aatgacccga    1320
acgggtctgg caactaaaga tggcaacctt cacgaaggag acataattct caagatcaat    1380
gggactgtaa ctgagaacat gtctttaacg gatgctcgaa aattgataga aaagtcaaga    1440
ggaaaactac agctagtggt gttgagagac agccagcaga ccctcatcaa catccccgtca  1500 ttaaatgaca gtgactcaga aatagaagat atttcagaaa tagagtcaaa ccgatcattt    1560
tctccagagg agagacgtca tcagtattct gattatgatt atcattcctc aagtgagaag    1620
ctgaaggaaa ggccaagttc cagagaggac acgccgagca gattgtccag gatgggtgcg    1680
acacccactc cctttaagtc cacagggat attgcaggca cagttgtccc agagaccaac    1740
aaggaaccca gataccaaga ggacccccca gctcctcaac caaaagcagc cccgagaact    1800
tttcttcgtc ctagtcctga agatgaagca atatatggcc ctaataccaa aatggtaagg    1860
ttcaagaagg gagacagcgt gggcctccgg ttggctggtg gcaatgatgt cgggatattt    1920
gttgctggca ttcaagaagg gacctcggcg gagcaggagg gccttcaaga aggagaccag    1980
attctgaagg tgaacacaca ggatttcaga ggattagtgc gggaggatgc cgttctctac    2040
ctgttagaaa tccctaaagg tgaaatggtg accattttag ctcagagccg agccgatgtg    2100
tatagagaca tcctggcttg tggcagaggg gattcgtttt ttataagaag ccactttgaa    2160
tgtgagaagg aaactccaca gagcctggcc ttcaccagag gggaggtctt ccgagtggta    2220
gacacactgt atgacggcaa gctgggcaac tggctggctg tgaggattgg gaacgagttg    2280
gagaaaggct taatccccaa caagagcaga gctgaacaaa tggccagtgt tcaaaatgcc    2340
cagagagaca cgctgggga ccgggcagat ttctggagaa tgcgtggcca gaggtctggg     2400
gtgaagaaga acctgaggaa aagtcgggaa gacctcacag ctgttgtgtc tgtcagcacc    2460
aagttcccag cttatgagag ggttttgctg cgagaagctg gtttcaagag acctgtggtc    2520
ttattcggcc ccatagctga tatagcaatg gaaaaattgg ctaatgagtt acctgactgg    2580
tttcaaactg ctaaaacgga accaaaagat gcaggatctg agaaatccac tggagtggtc    2640
```

| | | | | |
|---|---|---|---|---|
| cggttaaata | ccgtgaggca | aattattgaa | caggataagc | atgcactact ggatgtgact | 2700 |
| ccgaaagctg | tggacctgtt | gaattacacc | cagtggttcc | caattgtgat ttttttcaac | 2760 |
| ccagactcca | gacaaggtgt | caaaaccatg | agacaaaggt | taaatccaac gtccaacaaa | 2820 |
| agttctcgaa | agttatttga | tcaagccaac | aagcttaaaa | aaacgtgtgc acaccttttt | 2880 |
| acagctacaa | tcaacctaaa | ttcagccaat | gatagctggt | ttggcagctt aaaggacact | 2940 |
| attcagcatc | agcaaggaga | agcggtttgg | gtctctgaag | gaaagatgga agggatggat | 3000 |
| gatgaccccg | aagaccgcat | gtcctactta | accgccatgg | gcgcggacta tctgagttgc | 3060 |
| gacagccgcc | tcatcagtga | ctttgaagac | acggacggtg | aaggaggcgc ctacactgac | 3120 |
| aatgagctgg | atgagccagc | cgaggagccg | ctggtgtcgt | ccatcacccg ctcctcggag | 3180 |
| ccggtgcagc | acgaggaggt | gaggcgaggc | aggccacggg | caggaacagg agagcctggt | 3240 |
| gttttccttg | cactctcgtg | gacagctgtg | tgttcagggt | gctgtggaag gcattcctaa | 3300 |
| gggttggagc | agatgacttc | cagggagtct | ctcgctttga | gtccacgctg gcatggttgc | 3360 |
| agtctgtggg | aaagtggggc | aggcaggtgg | acttcagaag | agcttgaggg gtcagcactc | 3420 |
| cgcacaccca | tgccctcagg | tgcgatggat | aaacagaatg | gctttaggtg ccgtctgtcc | 3480 |
| aaattaccag | cggaaccttc | cttcccatgc | agtattgttg | tatgtacttg taacctttga | 3540 |
| ttaggtttct | ctctgtactc | ttagatgtcc | ttgcttttct | tccccatcct gcctttaacc | 3600 |
| tttctaatct | tgccaaagct | cttgagtgtt | tccccatcag | tttccttctc tcttatattt | 3660 |
| cagttttta | attgagttca | tgatcaaacc | ttcatctgat | cacatcacat gtactgtgca | 3720 |
| tccactgtga | ttagatagct | tatgggatcc | ttgaaatcac | attgacaggc actgtaaagt | 3780 |
| cacagccaag | ttagcaatta | ttagttgcac | ctcagagaat | gttggaataa tgatctttga | 3840 |
| agatgggatt | gttcatatat | ttggataatt | attgctgtgg | atttctctct agcattttag | 3900 |
| ctcattccag | taaatgattt | ttttcttat | gaaatagaac | taccaaaaaa aaaaaaaaa | 3960 |
| aaaagttcaa | caacaacaaa | ctgaaggggg | agaaaaatac | accattacca cagcaacaaa | 4020 |
| ttagtttatg | ctagacaact | tgtaaagaat | aaattaactt | ccaaatgcct atagacatgg | 4080 |
| atattagtga | cacaagagat | tttagacttt | tggagggttc | ttaaaaaatt gtgctttaaa | 4140 |
| ggaagagact | ctacattgga | tgcagccagt | ttttaaaaat | gtgtctgaag catttggtga | 4200 |
| tggtttctgc | ctgttcagta | aagaagcacc | ggctcagaac | ctcaacttct ggacttactc | 4260 |
| aagtttgcag | aactcctcca | aagcagtcga | gtgctctgtt | ctctctgctt ggatgttctt | 4320 |
| gttgtgaatg | aaccttatg | tcttgtagag | cataaggaaa | cccagcccag agccacgagc | 4380 |
| tcagatgagg | agggctgcta | gcagcgatca | acttagggac | aatagcccgc ccccagcatt | 4440 |
| caagccagag | ccgcccaagg | tacgtggctg | ggaagcccag | gatgggaagg aagaggaagc | 4500 |
| agatgcctct | gaagcctcct | ggacggccag | ggaggagcat | gcacactgag atggtgttta | 4560 |
| attacggttc | tgactcactg | tgttctctat | tagagcctat | cttttggcct gttgggtgaa | 4620 |
| ctcccaaatt | agggaagggc | aaaaaggaag | gaaaggcaat | attaggagag catatgattt | 4680 |
| taggactgtt | agtgtttatt | taatttactc | ttcttgttaa | | 4720 |

<210> SEQ ID NO 10
<211> LENGTH: 2084
<212> TYPE: DNA
<213> ORGANISM: Artificial Sequence
<220> FEATURE:
<223> OTHER INFORMATION: A synthetic zinc Finger Protein SNAI2 of Mus musculus

<400> SEQUENCE: 10

```
cagggagccg ggtgacttca gaggcgcctg cctgtccccc gccgcacctg agccaccgcg      60
atgctatagg accgccgcct ggaccgttat ccgcccgcgc ccgcccgcag ccaccatgcc     120
gcgctccttc ctggtcaaga aacatttcaa cgcctccaag aagcccaact acagcgaact     180
ggacacacac acagttatta tttccccata tctctatgaa agttacccta tacctgtcat     240
accaaaacca gagatcctca cctcgggagc atacagccct attactgtat ggacatcgtc     300
ggcagctcca ctccactctc ctttacccag tggcctttct cctcttactg gatactcctc     360
atccttgggg cgtgtaagtc ccccgccttc ctctgacact tcatccaagg atcacagtgg     420
ttcagaaagt cccattagtg acgaagagga gagactgcag cccaagcttt cagaccccca     480
tgccatcgaa gctgagaagt tcagtgcaa tttatgcaat aagacctatt ctacgttctc     540
tgggctggcc aaacacaagc agctgcactg tgatgcccag tctaggaaat cgttcagctg     600
caagtactgt gacaaggaat atgtgagcct gggtgccctg aagatgcaca ttcgaaccca     660
cacattgcct tgtgtctgca agatctgtgg caaggctttc tccagaccct ggctgcttca     720
aggacacatt agaactcaca ctggggaaaa gcctttctct tgccctcact gcaatagggc     780
ttttgcagac agatcaaacc tgagggcaca tctgcagacc cactctgatg taaagaaata     840
ccagtgcaaa aactgctcca aaaccttctc cagaatgtcg cttctgcata acatgagga     900
gtctggctgc tgtgtggcac actgagtggc gcaaccagtg tttactcaaa cagaatgcat     960
ttcttcactc caatgacaaa tgacaaatga agtccaaag acattttctc atgtgcttac    1020
caaccaaata gtatgtataa aaccacaaaa gagtcacaca cacacacaca cacacacaca    1080
cacacacaca cacagagaga gagagagaga gagagagaga gacagacaga cagacagaca    1140
gatacacaca cactacagaa cagaatctat gtacttaaag ttaattcgtt ctatgtgaag    1200
tttaaaatta tatttactga cagctagatt gaaaggataa aagataagaa tctttctctt    1260
taaagatgaa gtgaaaagca cattgcatct tttcttacta agaaagaata cagagattta    1320
cactgctgcc aaaccatttc aaccaaagga acagtatttc ttcttaatag aattgtaata    1380
gtgtttccaa gaggaagaga gtctgccaga cactatctca ggtgccttat aaagtactcc    1440
aagtttactt ccttaaatgt atgatgcctg gttgtcatca gtgaatgaca gccttttctg    1500
gattacctac aatgttttaa aactatattg ttaagaaaa aaaaaccaaa aacaagaaaa    1560
agaacagaac acaagagaat gtattaaagt attcttgttt tattttttgcc atgtgtgcct    1620
tggaagagga gggaaagaca aacttcaaac attcctggtg cgtgtcccat gtctttcttt    1680
ttaaaaaaga atcttaatgt tttataatac aaagtaatga aaatgtgcaa aagaatttct    1740
tagacattca gtaatgtact tagacttttg aaaattcatg tgatggatgc agtaatacaa    1800
tgcccctcca agtgcctgtc ttaatgactt gtgtagttga tgaactgatg taaatttgtg    1860
tttatttta tacaactgaa tgaactctgt atgaaagtga ggtacggtta atagccacgc    1920
ctatattcaa ccagaatact tgtgaaatca atgtcctttt ttaaaaagta actttcaagg    1980
tctctttttt acaataaaca ttttgagta aaaaaaaaa aaaaaaaaa aaaaaaaaa    2040
aaaaaaaaa aaaaaaaaa aaaaaaaaa aaaaaaaaa aaaa                        2084
```

<210> SEQ ID NO 11
<211> LENGTH: 2112
<212> TYPE: DNA
<213> ORGANISM: Artificial Sequence
<220> FEATURE:
<223> OTHER INFORMATION: A synthetic Zinc Finger Protein SNAI2 of Homo sapiens

<400> SEQUENCE: 11

```
aaaacgggct cagttcgtaa aggagccggg tgacttcaga ggcgccggcc cgtccgtctg      60
ccgcacctga gcacggcccc tgcccgagcc tggcccgccg cgatgctgta gggaccgccg     120
tgtcctcccg ccggaccgtt atccgcgccg ggcgcccgcc agacccgctg gcaagatgcc     180
gcgctccttc ctggtcaaga agcatttcaa cgcctccaaa aagccaaaact acagcgaact    240
ggacacacat acagtgatta tttccccgta tctctatgag agttactcca tgcctgtcat    300
accacaacca gagatcctca gctcaggagc atacagcccc atcactgtgt ggactaccgc    360
tgctccattc cacgcccagc tacccaatgg cctctctcct ctttccggat actcctcatc    420
tttggggcga gtgagtcccc ctcctccatc tgacacctcc tccaaggacc acagtggctc    480
agaaagcccc attagtgatg aagaggaaag actacagtcc aagctttcag accccccatgc   540
cattgaagct gaaaagtttc agtgcaattt atgcaataag acctattcaa cttttttctgg   600
gctggccaaa cataagcagc tgcactgcga tgcccagtct agaaaatctt tcagctgtaa    660
atactgtgac aaggaatatg tgagcctggg cgccctgaag atgcatattc ggacccacac    720
attaccttgt gtttgcaaga tctgcggcaa ggcgttttcc agaccctggt tgcttcaagg    780
acacattaga actcacacgg gggagaagcc ttttttcttgc cctcactgca acagagcatt    840
tgcagacagg tcaaatctga gggctcatct gcagacccat tctgatgtaa agaaatacca    900
gtgcaaaaac tgctccaaaa ccttctccag aatgtctctc ctgcacaaac atgaggaatc    960
tggctgctgt gtagcacact gagtgacgca atcaatgttt actcgaacag aatgcatttc   1020
ttcactccga agccaaatga caaataaagt ccaaaggcat tttctcctgt gctgaccaac   1080
caaataatat gtatagacac acacacatat gcacacacac acacacacac ccacagagag   1140
agagctgcaa gagcatggaa ttcatgtgtt taaagataat cctttccatg tgaagtttaa   1200
aattactata tatttgctga tggctagatt gagagaataa aagacagtaa cctttctctt   1260
caaagataaa atgaaaagca cattgcatct tttcttccta aaaaaatgca aagatttaca   1320
ttgctgccaa atcatttcaa ctgaaaagaa cagtattgct ttgtaataga gtctgtaata   1380
ggatttccca taggaagaga tctgccagac gcgaactcag gtgccttaaa aagtattcca   1440
agtttactcc attacatgtc ggttgtctgg ttgccattgt tgaactaaag cctttttttg   1500
attacctgta gtgctttaaa gtatattttt aaaagggagg aaaaaaataa caagaacaaa   1560
acacaggaga atgtattaaa agtattttg ttttgtttg ttttttgccaa ttaacagtat    1620
gtgccttggg ggaggaggga aagattagct ttgaacattc ctggcgcatg ctccattgtc   1680
ttactatttt aaaacatttt aataattttt gaaaattaat taaagatggg aataagtgca   1740
aaagaggatt cttacaaatt cattaatgta cttaaactat ttcaaatgca taccacaaat   1800
gcaataatac aataccccctt ccaagtgcct tttaaattg tatagttgat gagtcaatgt   1860
aaatttgtgt ttatttttat atgattgaat gagttctgta tgaaactgag atgttgtcta   1920
tagctatgtc tataaacaac ctgaagactt gtgaaatcaa tgtttctttt ttaaaaaaca   1980
attttcaagt ttttttaca ataaacagtt ttgatttaaa atctcgtttg tatactattt   2040
tcagagactt tacttgcttc atgattagta ccaaaccact gtacaagaa ttgtttgtta   2100
acaagaaaaa aa                                                       2112
```

<210> SEQ ID NO 12
<211> LENGTH: 1722

<212> TYPE: DNA
<213> ORGANISM: Artificial Sequence
<220> FEATURE:
<223> OTHER INFORMATION: A synthetic zinc Finger Protein SNAI1 of Homo
      sapiens

<400> SEQUENCE: 12

```
attcattgcg ccgcggcacg gcctagcgag tggttcttct gcgctactgc tgcgcgaatc      60
ggcgacccca gtgcctcgac cactatgccg cgctctttcc tcgtcaggaa gccctccgac     120
cccaatcgga agcctaacta cagcgagctg caggactcta atccagagtt taccttccag     180
cagccctacg accaggccca cctgctggca gccatcccac ctccggagat cctcaacccc     240
accgcctcgc tgccaatgct catctgggac tctgtcctgg cgcccaagc ccagccaatt      300
gcctgggcct cccttcggct ccaggagagt cccagggtgg cagagctgac ctccctgtca     360
gatgaggaca gtgggaaagg ctcccagccc ccagcccca cctcaccggc tccttcgtcc      420
ttctcctcta cttcagtctc ttccttggag gccgaggcct atgctgcctt cccaggcttg     480
ggccaagtgc ccaagcagct ggcccagctc tctgaggcca aggatctcca ggctcgaaag     540
gccttcaact gcaaatactg caacaaggaa tacctcagcc tgggtgccct caagatgcac     600
atccgaagcc acacgctgcc ctgcgtctgc ggaacctgcg ggaaggcctt ctctaggccc     660
tggctgctac aaggccatgt ccggacccac actggcgaga gcccttctc ctgtccccac      720
tgcagccgtg ccttcgctga ccgctccaac ctgcgggccc acctccagac ccactcagat     780
gtcaagaagt accagtgcca ggcgtgtgct cggaccttct cccgaatgtc cctgctccac     840
aagcaccaag agtccggctg ctcaggatgt ccccgctgac cctcgaggct ccctcttcct     900
ctccatacct gcccctgcct gacagccttc cccagctcca gcaggaagga ccccacatcc     960
ttctcactgc catggaattc cctcctgagt gccccacttc tggccacatc agccccacag    1020
gactttgatg aagaccattt tctggttctg tgtcctctgc ctgggctctg aagaggcct    1080
tcccatggcc atttctgtgg agggagggca gctggccccc agccctgggg gattcctgag    1140
ctggcctgtc tgcgtgggtt tttgtatcca gagctgtttg gatacagctg ctttgagcta    1200
caggacaaag gctgacagac tcactgggaa gctcccaccc cactcagggg accccactcc    1260
cctcacacac acccccccac aaggaaccct caggccaccc tccacgaggt gtgactaact    1320
atgcaataat ccaccccccag gtgcagcccc agggcctgcg gaggcggtgg cagactagag    1380
tctgagatgc cccgagccca ggcagctatt tcagcctcct gtttggtggg gtggcacctg    1440
tttcccgggc aatttaacaa tgtctgaaaa gggactgtga gtaatggctg tcacttgtcg    1500
ggggcccaag tggggtgctc tggtctgacc gatgtgtctc ccagaactat tctggggcc    1560
cgacaggtgg gcctgggagg aagatgttta catttttaaa ggtacactgg tatttatatt    1620
tcaaacattt tgtatcaagg aaacgttttg tatagttata tgtacagttt attgatattc    1680
aataaagcag ttaatttata tattaaaaaa aaaaaaaaa aa                        1722
```

<210> SEQ ID NO 13
<211> LENGTH: 1613
<212> TYPE: DNA
<213> ORGANISM: Artificial Sequence
<220> FEATURE:
<223> OTHER INFORMATION: A synthetic zinc Finger Protein SNAI1 of Mus
      musculus

<400> SEQUENCE: 13

```
cggagttgac taccgacctt gcgcgacccg gtgaccccga ctacctaggt cgctctggcc      60
```

```
aacatgccgc gctccttcct ggtcaggaag ccgtccgacc cccgccggaa gcccaactat    120
agcgagctgc aggacgcgtg tgtggagttc accttccagc agccctacga ccaggcccac    180
ctgctggccg ccatccctcc gcccgaggtc ctcaaccccg ccgcttcgct gcccacccct    240
atctgggact ctctcctggt accccaagtg cggccggttg cctgggccac cctcccgctg    300
cgggagagcc ccaaggccgt agagctgacc tcgctgtccg atgaggacag tggcaaaagc    360
tcccagccgc ccagcccgcc ctcgccggcg ccgtcgtcct tctcgtccac ctcggcctcg    420
tccctggagg ccgaggcctt catcgccttc cctggcttgg ccaacttcc caagcagctg     480
gccaggctct cggtggccaa ggaccccag tcgcggaaga tcttcaactg caaatattgt     540
aacaaggagt acctcagcct gggcgctctg aagatgcaca tccgaagcca cacgctgcct    600
tgtgtctgca cgacctgtgg aaaggccttc tctaggccct ggctgcttca gggccacgtc    660
cgcacccaca ctggtgagaa gccattctcc tgctcccact gcaaccgtgc ttttgctgac    720
cgctccaacc tgcgtgccca cctccaaacc cactcggatg tgaagagata ccagtgccag    780
gcctgtgccc gaaccttctc ccgcatgtcc ttgctccaca gcaccaaga gtctggctgc      840
tccggaggcc ctcgctgacc ctgctacctc cccatcctcg ctggcatctt cccggagctc    900
accctcctcc tcactgccag gactcctccc agccttggtc cgggacctg tggcgtccat      960
gtctggacct ggttcctgct tggctctctt ggtggccttt gccgcaggtg gctgatggag    1020
tgcctttgta cccgcccaga gcctcctacc cctcagtatt catgaggtgt agcctctgga    1080
cacagctgct tcgagccata gaactaaagc caacccactg gctgggaagc ttgaaccccg    1140
ctcaggggac cccacttccc tacctccctc aaggacccctt caggccacct tctttgaggt    1200
acaacagact atgcaatagt tccccctccc ccacccccgt ccagctgtaa ccatgcctca    1260
gcagggtggt tactggacac atgtccaggt gcccctgggc ctgggcaact gtttcagccc    1320
ccgcccccat ttgtcctggt gacacctgtt tcacagcagt ttaactgtct cagaagggac    1380
catgaataat ggccatcact tgttagggc caagtggggt gcttcagcct ggccaatgtg     1440
tctcccagaa ctattttggg gcccaacagg tggccccggg agaaagatgt ttacatttta    1500
aaggtattta tattgtaagc agcattttgt atagttaata tgtacagttt attgatattc    1560
aataaaatgg ttaatttata tactaaaaaa aaaaaaaaa aaaaaaaaa aaa             1613
```

<210> SEQ ID NO 14
<211> LENGTH: 3552
<212> TYPE: DNA
<213> ORGANISM: Artificial Sequence
<220> FEATURE:
<223> OTHER INFORMATION: A synthetic zinc Finger Protein Scratch 1 of
      Homo sapiens

<400> SEQUENCE: 14

```
gtggggaccc gcgctgcctc cgccgctcct cggatggtga cggggccctg ccgccgcagc     60
ccccccaagc cccggctccg caggcccaca gcgccggagc cccgcaggaa tcatgcccag    120
gtccttcctg gtcaagaagg tcaaacttga cgcgttctct tcggccgacc tggagagcgc    180
ctacggacgc gcccgcagcg acctcggcgc gccactgcac gataaagggt acctcagcga    240
ctacgtgggg ccctcgtccg tctacgatgg cgacgccgag gctgcgctgc tcaaagggcc    300
gtcgccggag cccatgtacg cagcagctgt gcgtggagag ctgggtccgg cggctgcagg    360
gtctgcgccg ccgcccaccc cgcgcccgga gctggccacc gctgcgggcg gctacatcaa    420
cggcgacgcg gccgtcagcg agggctacgc ggcggacgcc ttcttcatca ccgacggggcg    480
```

| | |
|---|---|
| ctcgcggcgt aaggcttcca atgccggctc tgccgccgct ccctccacag cctcggcggc | 540 |
| ggcccccgac ggcgacgccg gaggcggggg cggggcgggc gggcgcagct tgggatccgg | 600 |
| gccgggggc cggggcggca cgcgcgcggg ggcaggcacc gaggcgcgcg cggggccagg | 660 |
| ggccgcaggt gctggcggcc ggcacgcgtg cggcgagtgc ggcaaaacat acgccacgtc | 720 |
| gtcgaacctg agccgccaca agcagacgca ccgcagcctg gacagccagc tggcgcggcg | 780 |
| ctgcccgacg tgcggcaagg tgtacgtgtc catgccggcc atggccatgc acctgctcac | 840 |
| gcacgacctg cgccacaagt gcggcgtgtg cggcaaagcc ttctcgcggc cctggctgct | 900 |
| gcagggccac atgcgctcgc acaccggcga gaaacccttc ggctgcgcgc actgcggcaa | 960 |
| ggccttcgcc gaccgctcca acctgcgcgc gcacatgcag acgcattcgg ccttcaagca | 1020 |
| cttccagtgc aagcgctgca agaagagctt cgcgctcaag tcctatctca acaagcacta | 1080 |
| cgagtcggcc tgcttcaagg gcggcgccgg aggccccgcg gctcctgcgc cgccacagct | 1140 |
| cagccctgtg caggcctagg gcggcggggc ctcccccagc caggtcggct ctcagcaata | 1200 |
| cggccccca gggaagtctt cgctggcgtc cgggtggagg ggccggaggg cgggcccctc | 1260 |
| ctcacagcaa taggggagg ggggcccggt cccaccccgc cccgcccgcc aggggccttg | 1320 |
| ccggcccctt caagcaatag ggtcccgagg ggagacccac cccgagcccc ctcccctccc | 1380 |
| ctccagggtg cccccggctt tctcccagca atagggtcga cgagacctag aaccgaacct | 1440 |
| catctccgag ttgggtctct gaagacgggg gtgaggtgag gtaggagcg ccctccttct | 1500 |
| cccgcctctg cgcccctgga tcgcgtcgca gggactcagg tcttccccac cccttcccaa | 1560 |
| gccttctagc gcagggcctg cggcccagac gtccagggag ccggcccctc ccggcagca | 1620 |
| ggccggggcg gagcaggagc gggcgggcct gcagggacgc ccctgcctag cagccttcgc | 1680 |
| ggaactcccg gcagtgttag acgcgttgtg ggtcggggag aggggcggac ggcggcaccc | 1740 |
| cctccctcgg gttgcttctg gggcctcagt cggagccgcc ctcctaccct cgcctcgcat | 1800 |
| cctctgccaa atccgaattc ttccagccca gcttcccggg ctctgtcctc catatcgaat | 1860 |
| aataatgaca catatcgaat cgcatggact tatccgacct cctcagaccc cgcttccgcc | 1920 |
| ctgccccggg ccccaccccc cccccccgta ccccaggcat tcgtgttgga ggacggattc | 1980 |
| ccggggccgg caggcaggcc tgggcgctgc cctctacaca cctctgtctt cgctttgcgg | 2040 |
| gtaaagcccc ctgggggggt tgcggacgcg tcgggtttct tttctgtat ttgtacgttt | 2100 |
| tatttatgaa cggattgcac tcgggtcagg gagggggcgc tgaacccca tcttgcccgc | 2160 |
| cgacgccggg ggcctgggat gtccgggatt actttccacg ccccgaggcc cgcccctagc | 2220 |
| tgggagcctc tagggagcct caggccccgc ctctccgagg caggcccctc ccctgagacc | 2280 |
| caggcccgc ccctgagacc caggcccgc ccccactcgg ttgccaactt tcgcccgtct | 2340 |
| atgccaaagc ctcggcggcg accccgcccc aagggcccgc ccattggcc gccgcctttg | 2400 |
| tgacgtcact gcatgcagcc ccaccctcc tcccgatcct acccggggct gcccgctccc | 2460 |
| cctccctctt aggtagtccg aagccgacta tagagcaata atgcgcactg catgcgaagc | 2520 |
| tgccgccgcc tctagagtta ctgagaatca ggtatcccct cgccctaccc accccatagg | 2580 |
| cccctagatc agggacgctg cgcggggccg ccgcgcagaa cttctctccc acccctcccc | 2640 |
| gaccccacg gcagagcccg gcggctgtaa tggttccatg ggcgggggtg gggtggttgc | 2700 |
| ccccaagacc cctccttcag gcattaatca ttcactgacc gttcattgag cacctactat | 2760 |
| gtgccaggcc aattgctgag tccgccagga gcgcagccac ctgctgggag gtgtgtttgc | 2820 |
| aggacagggg tccaaccggc ttgggtgggc cagggaagaa cggcagatgc agagagacca | 2880 |

| | |
|---|---|
| ggtccctagg ttcacatgcc ccctacactc ctccccacct caaccagtcc ctgctgggca | 2940 |
| caactgggct ctacctttga gttaggcctt ttgactccag ctgaggggga cagatccagg | 3000 |
| gctcctgggc ccccacacag gtggccactt ctctgatcct ctggccaaca cacatctgcc | 3060 |
| atgtccagcc aggggcagag ccatggctgg agaagaaggt gccagctgta gcctatggtg | 3120 |
| tggccagcct cacccccagc agcaagcgtg gctgccccca caaggatgac ccaccgctct | 3180 |
| gcacagcagt gcccacatcc aaacacccta cacaaccagg tgtggtgcct gcacagctcc | 3240 |
| caagctgggg cctgcccacc tgtgccgcat gcacacgcac acacaggcgc cccaccctca | 3300 |
| ccccacccca tactcctgtc tacctaccta aggagaaagc tggagggctg tgggcccgtc | 3360 |
| agggtctcct gcttccccct acaccccgcc gccgtggaaa gccatgggcc cctcccgcc | 3420 |
| cccataacta agcagcacaa taaccgactt agcgaattca ggtagaagga acgtttaggt | 3480 |
| agcacctatt ttgtactgat tctacaagta gggcccgagg tgcgggggcc ctcgggtggg | 3540 |
| ggctgcggcc gc | 3552 |

<210> SEQ ID NO 15
<211> LENGTH: 3594
<212> TYPE: DNA
<213> ORGANISM: Artificial Sequence
<220> FEATURE:
<223> OTHER INFORMATION: A synthetic zinc Finger Protein Scratch 2 of
      Homo sapiens

<400> SEQUENCE: 15

| | |
|---|---|
| ctttcttctc tctctgtttc tctcttgtgt cttttttgtcc ttatcttggt ctctctgctt | 60 |
| ctatttctac ctctctcagc gtgtgcgtct ctctttccct gtatgtctct gtctttctcc | 120 |
| gagtctctct tcttctcccc gcccccctca ctcccctttc tccgtccctc tctgtctctg | 180 |
| cgcctttctc gccctcactt tctcccctcc tgcctgctcc gggcctgccc ccaccgccgc | 240 |
| cggttcaggg gaacgtgtgc ggagcgattg tcctggggga catttgatgg attagagcgc | 300 |
| cgagcggttc cattgctagg ggaccacctg atctccagcc tgcgtcccat ataaagccgg | 360 |
| cagccggagt gctgagcgca gctcccgcga tccctgtct gcgcgccgcc gccgccaagc | 420 |
| ccgagcccga gccggggccg ccgccaccgg tgccggctcc gagcggcctc ccgcgctcca | 480 |
| gcccgctggg agctgtccag tgctgaaaac ccgcgcggac acagccgatc gcgcccggcc | 540 |
| ggccgcctcc ccgcaccgag ccccgcgccg gccgcgccat gccgcgctcc ttcctggtaa | 600 |
| agaagatcaa aggggacggc ttccagtgca gcggggtgcc ggcccccacc taccacccct | 660 |
| tggagacagc ctacgtgctg cctggcgccc ggggcctcc cggggacaac gggtacgccc | 720 |
| cgcaccgcct gccccgagc agctacgatg cggaccagaa gccgggcctg gagctggccc | 780 |
| cggccgagcc cgcgtacccg ccggcggcgc cggaggagta cagcgacccc gaaagcccgc | 840 |
| agtcgagcct gtcggcgcgc tacttccgag gggaggcggc agtgaccgac agctactcca | 900 |
| tggacgcctt cttcatctcg gacgggcgct cgcggcggcg gcggggcggg ggcggcgggg | 960 |
| acgcgggggg ctcgggagac gcgggggggcg ccgggggggcg cgcggggcgc gcggggcgc | 1020 |
| aggcgggcgg cgggcaccgg cacgcgtgcg ccgagtgcgg caagacctac gccacgtcgt | 1080 |
| cgaacctgag ccgccacaag cagacgcacc gcagcctgga cagccagctg gcgcgcaaat | 1140 |
| gcccgacgtg cggcaaggcc tacgtgtcca tgcccgcgct cgccatgcac ctgctcacgc | 1200 |
| acaacctgcg ccacaagtgc ggcgtctgcg gcaaggcctt ctcgcggccc tggctgctgc | 1260 |
| agggtcacat cgcctcgcac accggcgaaa agccgttcgg ctgcgcgcac tgcggcaagg | 1320 |

```
ccttcgccga ccgctccaac ctgcgcgcgc acatgcagac gcactcggcc ttcaagcact      1380
accgctgccg ccagtgcgac aagagcttcg cgctcaagtc ctacctccac aagcactgcg      1440
aggcggcctg cgccaaggcg gccgagccac ccccgccgac ccccgccggc ccggccagct      1500
gagccttccg cctcgccctc gcgcccggaa ctcgctctcc acgcgccccg ggcccctac       1560 ctgcgcccgc agcgccctcg cccagccccg gctgcgtttc cctgcccatg accctctcgt     1620
ggggaccccc ggcccggccc ggaacttttc tccccaaccc ccaaaccac gactcacttc       1680 cacaccgtct tccccagcgt ccccgaccc acttcatcct ttccggccat ccctcggacc       1740 ttgaccccc tgtccgcgcc ttcaaggctc ccaactcagg caccaggtcc gcacctctcc       1800
cgcgccccag agccggaaat ttctccctcc cagacccgc gctgctcttc taacttctag       1860 atctttctc tcgcttctca gctgaatctc tctgaccatt cctctactgg agccccaat       1920 gaaagccgca aacctatacc cttgacgccc ataccgct cagtttcccc atccacacct        1980 ggacgcagg cctgccgccc tgagaccaca gtccaacccc agaccatccc tctggcctct      2040
gctgaatctc ccagagtgtg tccatctggg gatctaatct tcacccttct tgaagtctcc     2100
gatctgtccc tgatcccatc catgctcagg ccttaggtct ggccattcac acacacacac    2160 accccacac cccactccca cacacagttc ctactgtctt cagtccatgg ggatctcatc       2220
acccactccc agcccagct ccagctgccc tcacctctct agcagctctc accctctga       2280 gtctacctaa cctggagggg gcttgagggg cacttcaggg ccctgccccc taatgtaacc     2340
cctctctcac cccggcacaa cctgggcttc cacagtctgg agctgcccta ccccagatt      2400 ctctgagcac tttcccccat ccccagggcc acagatcccc ttccttactt gttgggggga    2460
ggtctggagc acctgccaa tgcccttccc ccatccggct gggtccttcc agttatttat     2520
ttgtgtattt atttatttat ctatttatta ttctatttaa tctcttggcc tcacccaggg    2580
accgtctggc ttccccagct ggactgggag gtcaggaagc caggcaagga gagggacagc    2640
acaggccaca gagggctgcc cccaccacac acacccccgc gtctcgggag aaacccaccc     2700
tcttcagagc ctgcactcgc taaggaaggg gactcgagaa tggggggca gcttgctgac     2760 cctcaactgg gggggtgagg gagcatcagg aggtccaggc gtggggcagg tccccaccttt  2820 cctgaacctt ccctgccac tccaggcggc ccggagagag gagcctcttc gatttgtttc     2880
ctgtttattc ttcttcccga gggacccag gttccaggga ccgactgagc cccggaccccg    2940 ctggggcctc tggcctgctc cccggagggg gcgctctctc ccggccatgt ctatgcaact    3000
ctcccggaca gaggggccgg gctgccagcc accgcccgt tggccgccac tacctcctcc     3060
gctgcgcttt tgcatgcccg ggcgaggacc gaagcacaca cctccacgcg cacgggccct    3120
ggccccctcc gctttaagca cacgcctctg cccattgct ctgcagccag cttgggggca    3180
ggagtcctgg actctcagat cctcctctcc cctcctctta gccacaaaag agggggggaga  3240 ctggaggcac ccctgcagca ggggcacttc cctaggggctc cagagggggtg aatgggcctt  3300 tgctcagctc caggcccagc gggaagggag gctgcaggga tggtgggagg gagaggggta   3360
gcagaagcaa ttatggaggc gttgaccctg taaatagcaa cttctgacag caataatttt    3420
ccatgcatgc taagcctttt ggccatattt tgtatgagcg cttggcgctc ctcctccgtc     3480
ctatcccaac tcaccccaa accccatcc cttccccacc tccagcagta ttacttgtaa      3540
cgcaattcag ggatattaaa gggactttgg ccactcaaaa aaaaaaaaaa aaaa           3594

<210> SEQ ID NO 16
```

<211> LENGTH: 4010
<212> TYPE: DNA
<213> ORGANISM: Artificial Sequence
<220> FEATURE:
<223> OTHER INFORMATION: A synthetic zinc Finger Protein Scratch 1 of
      Mus musculus

<400> SEQUENCE: 16

| | | | | | |
|---|---|---|---|---|---|
| ggggccgggc | cagccctgca | cccattcgca | gcctccgggc | ccgggacgga | gccgctcccc | 60 |
| ccctctccgc | cccccagcc | tcctccccg | cctgtccagg | ggcggcactg | cgggctggga | 120 |
| agccgggacc | agaggaggga | aggaaggaag | gaaggaaaga | agagaaaaga | agagaagagg | 180 |
| aggaaggaag | gaaagaagga | aggaaggaag | gagagagaaa | gagaggaggg | atccggagag | 240 |
| gaagaagaaa | agacgcaggg | cagaaagaag | agagaggacc | acactcgccc | agcagcatcc | 300 |
| acaggccaga | caggggacag | tgctgcttcc | accgctcctc | ggatggtgac | ggggcctcgc | 360 |
| cgcggacgca | gtcccctga | gccccggctc | tgcaggccct | cactgccgga | gccctgcagg | 420 |
| aatcatgccc | aggtccttcc | tggttaagaa | ggtcaaactt | gacacattct | cttcggcaga | 480 |
| cctcgacagc | tcctacgggc | gcgcccgcag | cgatctcgga | gtgcgactgc | aagataaagg | 540 |
| atacctcagt | gactacgtgg | ggcctgcgtc | ggtctacgat | ggcgacgctg | aggcggcgtt | 600 |
| gctcaaaggg | ccatccccgg | agcctatgta | tgctgcggct | gtgcggggag | agctgggtcc | 660 |
| cgcggcctct | ggctcagcac | cgccgcccac | ccctcgccca | gagctggcta | ctgctgctgg | 720 |
| cggctacatc | aacggcgacg | cggcggtcag | cgaaggctac | gcggccgacg | ccttcttcat | 780 |
| cactgacggg | cgctcacgcc | gtaaggctgc | taatgccaac | gctgccgcgg | ccccctcgac | 840 |
| agcctcggtg | gcagccccg | acagcgacgc | tggaggtggg | ggcgggccgg | gcacgcgagg | 900 |
| ctctggatca | gggtccgcta | gtcggggcgg | cacgcgcgtg | ggggcgggca | ccgaggcgcg | 960 |
| tgcggggtcg | ggagccacgg | gcgctggtgg | ccggcacgcg | tgcggagagt | gtggcaaaac | 1020 |
| ttacgccacg | tcgtcgaacc | tgagccgcca | caagcaaacg | caccgcagct | tggacagcca | 1080 |
| gctggcaagg | cgttgcccaa | cgtgtggcaa | ggtgtacgtg | tccatgccgg | ccatggctat | 1140 |
| gcacctgctc | acgcacgatc | tgcgccacaa | gtgcggcgtg | tgcggcaaag | ccttctcccg | 1200 |
| gccctggctg | ctgcagggcc | atatgcgctc | gcacacgggc | gagaaaccct | tcggctgtgc | 1260 |
| gcactgcggc | aaggcctttg | cagaccgctc | caacctgcgc | gcgcacatgc | agacgcactc | 1320 |
| cgccttcaag | cacttccagt | gcaagcgctg | caagaagagc | ttcgcgctca | gtcttatct | 1380 |
| caacaagcac | tacgagtcag | cctgcttcaa | gggcggcgct | agcggccccg | caaccctgc | 1440 |
| gccgccgcag | ctcagcccgg | ttcaagccta | gggcagcggg | gcctccgcca | gccaggtcgg | 1500 |
| ctctcagcaa | tacgggcccc | cagggaaatc | tccgctggcg | tccgggcgga | ggggctggag | 1560 |
| ggcgggcccc | tcctcacagc | aatagggca | gggagccggc | cccacccgc | ccgctcgcc | 1620 |
| aggagccttg | ccagccccctt | caagcaatag | ggtcctgagg | ggagacccac | cccgaaaacc | 1680 |
| ctccctctc | ctccagggtg | ccccaggctt | tctcccagca | atagggtcga | ccagaccag | 1740 |
| aaccgaacct | catctcttag | ttgggtctct | gaagacaggg | ggtgaggtga | ggtaaggagc | 1800 |
| gccctcctcc | ctcctctgcg | ccctggatc | gcgttgcaga | gactcaggtc | ttccccaccc | 1860 |
| cttcccaagc | cttccaggcc | aagccttcag | tccggcgtcc | agggagtcag | ctccactcgg | 1920 |
| gcagctggcc | ggaggaggag | caggatatca | ggcgggccac | agaggcgttc | tgttccgcag | 1980 |
| gctttgcaaa | cctcccggga | gtgctagacg | atttggggat | gggagggggc | gcggacggcg | 2040 |
| gcaaccctct | tcctcgggtt | ctttctaggg | cctcagtccg | agcctccctc | caacccacgc | 2100 |

| | |
|---|---|
| ctcgcatcct ctgccaaatc ctaattcttc cagcccggct tccggggctc tgtcctccat | 2160 |
| aacgaataat aatgacgcat atcggaatcg catgaactta tccgacctac tcagaccccg | 2220 |
| atcccgccct gccccgggcc ccctccctcg ctccccaggc ttcgggtgtt ggaggacgga | 2280 |
| tgcccgggcc ggcaggctgg cgtgccactg ccctctacac acctctgtat ttgctttgcg | 2340 |
| ggtaaagccc cctggggggg ggggttgcgg acgcgtcggg tttctttctt tctgtattta | 2400 |
| tacgttttat ttatgaacgg attgcactcg ggtcagggag ggggcgccga accctcatcc | 2460 |
| ttcccgccga cgcccggggc ttaggctgtc caggaccact tcctctgccc ccgaggccgg | 2520 |
| cccctttcctg gaggcccagg ccccactccc actcggttgc aactttcac ccgtctatgc | 2580 |
| caaagcctcg gcggtgaccc tatcccaagg gccccgctcc attggccgcc gcctttgtga | 2640 |
| catcactgca tgcagtccca cccttcttcc caacccttcc cggggctgcc cgctccccctt | 2700 |
| cctcttagtt agtccgatgc agactataga gcaataatgc gcactgcatg tgaagctgcc | 2760 |
| gcagcctcta gagttactga gaatcaggta tcccctgccc tacccatccc ataggcccct | 2820 |
| agatcaggga tgctgcgcgg ggccggccac gcagactttc tttccccata ccctacccca | 2880 |
| gggcagagcc cggcaggcgt catggttcca gaggctggga tggaatggta tcacccaagt | 2940 |
| cctctcttgt cagtccttca tcactcaccg acccatcatt gggtacctac gatatgccag | 3000 |
| gcccattcct gaatccgtca gagatgtggc aaccttctgg aggtgcccat cagtgacagg | 3060 |
| gcccaatacg cataggtagg ccagggtgga aggcagatgc agagggctga atccctgggc | 3120 |
| ccctatggcc tctcctaccc acctcagtcc tagaatacgc tgggtgtagt caggctctgc | 3180 |
| cttttgacttg ggccttatgt tcccagctca aattggacag gtcccagggt ctctggggcc | 3240 |
| cagcttcacc agggccaccc atacaggtac ccattttctg attccctgag atacgaggct | 3300 |
| ctgctgtctc tgtgccgcta aggtgcaaca tgctggagta tatgatatgg ccagtctcaa | 3360 |
| cccagcacca agcttggcta accctcctgg tgcggacccg caggcctagc ataacagtgc | 3420 |
| ccatatctaa cccccttact ccacctggca aaatgcccac agttcctagc ctgggcctgc | 3480 |
| cagcctgtgc cgcatgcaca cgcacacaga ggcgcccacc ccgccccact ctctactcct | 3540 |
| gtctacctac ctatggagaa ggctggaagg gctgtgggcc cgccaggatc tcccgcttcg | 3600 |
| cccacaccct gccgccgtgg aaagccatgg gcccctccc gcccccataa ctaagcagca | 3660 |
| caataaccga cttagcgaat tcaggtagaa ggaacgttta ggtagcacct attttgtact | 3720 |
| gattctacaa gtagggcccg aggtgcgggg ggccctcggg tgggggctgt ggctgccggc | 3780 |
| ccgcccccgcc cccaccccccg cctgcgcccc gccaccttgt acatactcct ggcccgcaac | 3840 |
| aggccgggat ttttactcgg gccgtgtccc tcttccgccc ccgtttgggg ccgggccggc | 3900 |
| cggacagacg gacggacgga cagacctcct tcctaagcac aatagcacca gctcctcgga | 3960 |
| gcgccgcacc tccacgagga gaataaatgc cactcttgat agaatttgga | 4010 |

<210> SEQ ID NO 17
<211> LENGTH: 3395
<212> TYPE: DNA
<213> ORGANISM: Artificial Sequence
<220> FEATURE:
<223> OTHER INFORMATION: A synthetic zinc Finger Protein Scratch 2 of
      Mus musculus

<400> SEQUENCE: 17

| | |
|---|---|
| tctctctctc tctctctctc tctctctctc tctctctctc tctctctctc tctctctctc | 60 |
| tctctctctg cgcctgtgtc cctctcactc tctcccctcc tgcttgctca ctgctcgttc | 120 |

```
ctctctgcgc ctggcctgcc cccaccgccg gttcagggga acgtgtgcgg agcgattgtc      180 ctggggaca tttgatggat tagagcgctg aacagttcca ttgctggggg accacctgat       240
ctcctccagc ctgcgtccca tataaagccg gcagccggag tgctgagcac agctacagcg      300
accgcctgtg tgcgcgccgc cgccgccgcc gtcgccgccg ccgccgcgcc cgagcggcac      360
ccgagcccga gccgcgaccg tcgccacccc gccggctccg cggacgcccg cccgctggga      420
gctgtccagt gctgaagccg cgccgacag ccaatcgcgc cggccggccg cctcccccac       480
cgggcctccc gtgccctgcg agcccccgc ccggctgcac catgccgcgt tccttcctgg       540
tgaagaagat caaagcggat ggcttccagt gcagcggggt gtcagccccc acctaccacc      600
ccctggagac tgcctacgtg ctgcctggca cccgcgggcc tccgggggac aacggttatg      660
tggcgcactg tctgcccccc agcggttacg atggcgagca gaagcctggg ctggagctgg      720
cgcccgccga gccgcctac ccggccgcgg cgtccgaaga gtacagcgac cccgagagcc       780
cacagtccag cctgtcggcg cgctacttcc gcggggaggc ggccgtgacc gacagctact      840
ccatggacgc cttcttcatc tctgacgggc gttcgcggcg gcgccgggcc ggggctggcg      900
gggacgcggc gggcgcaggg gacgcgggcg gcggcggcgg tggcggcggc ggcggggagc      960
gcgcggggcg ctcgggggcg acggcgggag gcgggcaccg gcacgcatgc gcagagtgcg      1020
gcaagacgta cgccacgtcg tcgaacctga ccgccacaa gcagacgcac cgcagcctgg      1080
acagccagct ggcgcgcaag tgcccgacgt gcggcaaggc ctacgtgtcc atgcccgcgc      1140
tcgccatgca cgtgctcacg cacaacctgc gccacaagtg cggcgtgtgc ggcaaggcct      1200
tctcccggcc ctggctgctc cagggccaca tgcgctcgca caccggcgag aagcccttcg      1260
gctgcgcgca ctgcggcaaa gccttcgccg accgctccaa cctgcgcgcg cacatgcaga      1320
cgcactcggc cttcaagcac taccgctgcc gccagtgcga caagagcttc gcgctcaagt      1380
cctacctcca caagcactgc gaggctgcgt gcgtcaaggc cgccgagccg ccgccttccg      1440
ccggcccggc cagttgagcc tctgccatgc gggatgcccg ccgaggcttc tctcccaccc      1500
ctcagtctgc gtctcccctg cctgcgccct cggtggggtg ggggtgaacc ccatcttggc      1560
ctagaacttt cttttcaacc cccgactgaa cccaccactc atttcctgca tcggatctcc      1620
cttcgcaccc acccactttg tccattctgg ccaccactcg gaccttgacc cccatgtctg      1680
gccttcaagg ctcccaactc aggcaccagg tccgtacctc ttccatgtcc cggcgctgga      1740
agtttctccg gccccgactc taggctgtgc tccttaacta gatctttctt ttcatttctc      1800
agcagagtca ttggccattc ctctattgga gccctcaatc caaacccaaa tgtacccttg      1860
atttcctatc tgcctcagtt tccctgtcca cacagtccaa tcccttgggt ctctgctgaa      1920
tttccgtgtg tgtgtgtgtg tatgtgtgtg tgtgtcccca taccgtaatc taatcttcac      1980
cactcttgga gtcctctgcc tgtccattcc tgagcccctc catgcttggg ccttaggtcc      2040
agcctcttac acacacgatt ccacctgaca ttatcagtcc tcccggatct catcagacat      2100
cctgctctct ccagctccat cttcccacta gtagctccca gtcctcagtt ttcctagctg      2160
ggaacagact tgggaggcag cccaaggctc tgccctctca ggtgacccct cttgccccag      2220
gaaagttcct gtctaggcct caggcctgga gctgcgattt cccagactat ctgagcactt      2280
tccctcgccc caggactaca ggttcgcctc tgcctttgct agagaacagc ctggagcacc      2340
tcacccatgg acacatcccc tcgtccggca gggcccttc cgctatttat ttgtgtattt       2400
atttatttat ctatttatta ttctatttaa tctcttggct tcacccaggg actgtctggc      2460
ttccccagct ggactgggaa gtcaaagggt agagtcagca aggccgtccg tcgctggctg      2520
```

```
ctcctcccct tatgggtctg gggagaagcc caccettate agagcctcaa ctccttagga    2580
agagaggcct ggagaaatgg ggggaggcgg agcctgctta gcctcagctg ggtggggagg    2640
ggccatcaga aggtcctatt tgggggcagg tccccggcct tctgcgcctt ccactcctgt    2700
cccaggaagc ccttctggag cctctccctt tgtttcgtat ttattcctct ttcagaggga    2760
ccccaggttc cagggaccga ctgagccccg acccgctggg gcctctggcc tgctcccgg    2820 gaggagtgct ctctcccggc cacgactatg caactctccc gggcagaggg gccgggactg    2880
ccagccaggc gcctattggc caccactacc tcctccaccg cgcttttgca tgcccgggcg    2940
aggaccgaag cacacacctc cgcgcccacc tgcccggccc cctctgcttt aagcacacgc    3000
ctctttccac gtccctctgc gttccctttg tgggcaaaag tcctggacac tcagacctcc    3060 ttccctccc cctagccaca aaagagggtg gagattgcag accgctccag gttgctctct    3120
agggtttcgg aggggtggag cttcgttagg ccccaggctc caggaggaag tctgcagaga    3180
tggtgggaga gagaggggtc accagaagca attttggagg gtgctgaccc tgtaaatagg    3240
aacttctgac agcaataatt tcccatgcat gctaaatctt ttggaccctc ccttgccgta    3300
cccccaactc acccccccac ccctattcct tccccacctt cagcagtatt acttgtaacg    3360
caattcaggg atattaaagg gactttggcc actca                               3395

<210> SEQ ID NO 18
<211> LENGTH: 1713
<212> TYPE: DNA
<213> ORGANISM: Artificial Sequence
<220> FEATURE:
<223> OTHER INFORMATION: A synthetic zinc Finger Protein SNAI3 (Smuc) of
      Homo sapiens

<400> SEQUENCE: 18
cagcagtccg gacccaggcg cgcccctccc gccccagccc accccggcct gccgcccggg      60
aggggaacat gccgcgctcc ttcctggtga aaacgcactc cagccacagg gtccccaact     120
accggcggct ggagacgcag agagaaatca atggtgcctg ctctgcctgt ggggggctgg     180 tggtgccoct cctcccccga gacaaggagg ccccttctgt gcccggtgac cttccccagc     240
cctgggaccg ctcctcggcc gtcgcctgca tctccctgcc cctcctgcca cggatcgagg     300
aagctctggg ggcctctggg ctggacgcct tggaagtcag cgaggtcgac cctcgggcca     360
gccgggccgc cattgtaccc ctcaaagaca gcctgaacca cctcaacctg cccccactgc     420
tggtgctgcc cacacggtgg tccccgacct tgggcccaga ccggcacggg gctccggaaa     480
aactgcttgg ggctgagcgg atgccccgag cccccggcgg ctttgagtgc ttccactgcc     540
acaaacccta ccacacgctg gccgggctgg ccaggcaccg gcagctgcac tgccacctgc     600
aggtggggcg tgtcttcacc tgcaagtact gcgacaagga gtacaccagc ctgggtgccc     660
tcaagatgca catccgcact cacacgctgc cctgcacctg caagatctgt ggcaaggcct     720
tctccaggcc ctggttactg cagggccatg tccgcaccca cagggggag aagccctatg     780 cctgctcgca ctgcagcagg gcctttgccg accgctccaa ccttcgggcc catctgcaaa     840
cgcactcaga cgccaagaag taccggtgcc ggcgctgcac caagaccttc tcccgcatgt     900
ccctcctggc gcggcatgag gagtctggct gctgcccggg ccctgagag gcacgtggtc     960 ggcgcaggta ggagggatgg tcctcaccgg gagagctggc gtccctcctg ccccagagg    1020 agccaggagt ctgggagggc ggggcctggc ctcacacttg gtgcgtcctc cacatctgcg    1080
tccaatcaga accaaagaag tccagcgggg gccactgggc cggaggacac tcccccaggc    1140
```

```
atcccaccgc gcggagccca ctcagaggag actcctctcc cggggaaggc tttcatcaga    1200
acaagagcca tggttccatt tcgacacggc caggtctccg gggctaccct tccaagagtc    1260
agagcctcgg ggaggtggcc gccagcatgg gccggcactg ccgccggatg gctggcaagg    1320
ctgcctagtt ccattgcagc agaaatgaac agttctgact tatagtgagc accgccctgt    1380
ggcccttcct cagtaggcac aactacctct cagccagccc cgccagcct  ttggtttggg    1440 gtctgggacg agctgcccca tgtcacacgt ctatgtgcat gtgcacacac actcaaacat    1500
gtacacacac gtgccctccc cacctcacta gactctccgg gagatggggc aggactggga    1560
gagcccacga ttggtgattt gggtgtgttg ggatgaggcg gagtgcctgt gggatttgtc    1620
ccggtcagag cctcaggggg ctggggtctc agggcactca gcttcccagg caataacagc    1680
cgtggggtaa taaatggtct ctgcacacct gca                                1713

<210> SEQ ID NO 19
<211> LENGTH: 1589
<212> TYPE: DNA
<213> ORGANISM: Artificial Sequence
<220> FEATURE:
<223> OTHER INFORMATION: A synthetic zinc Finger Protein SNAI3 (Smuc) of
      Mus musculus

<400> SEQUENCE: 19
gccggcgccg ccagactctg cagtcggtaa tcccgctgca ggctctggct agactctgcc      60
tgctctcggg aggggaccat gccgcgctcc ttcctggtga aaacgcactc cagtcacagg     120
gtccccaact acgggaaact ggagacactg agagaagcta atggctcctg ctctgcctgc     180
aaggagttgg caggatcccg ccacctgcca gatgaggagg ccccttgcaa tcccagtgac     240
cccctacagc cttgggacag tacctctgcc gttgcctgca tctccctgcc tcttctgccg     300
aatcacagag aaactctggg agtctctggc ccagaacctc aggaaaccag ctgggtgggc     360
cctcgggctg cccaggcccc cagtgtgact cttaaagaca gcttcactct accccgctg      420 ttggtgctgc ccacacgctg gcccccaatc ctgggcccag acggagctct aaatgaacat     480
ctcagggctg aggggacatc tcgagtccca ggtagctttg agtgcatcca ctgccacagg     540
ccgtatcata cgctggctgg cctggccagg caccagcagc tgcactgtca cctgccgact     600
gggcgcgcct tcacctgcag gtactgtgac aaggagtatg ccagcctggg tgccctcaag     660
atgcatatcc gcacccacac gctgccctgc atctgtaagg tgtgcggcaa ggccttctcc     720
agaccctggc tgctccaggg tcacatccgc acccatacag gtgagaagcc ctatacctgt     780
tctcactgca gcagggcctt cgctgaccgc tccaacctga gggctcacct gcagactcac     840
gttggtacca agaagtacag gtgcgccgtg tgccccaagg ccttctcccg catgtctctc     900
ttggcgcggc atgaggaagc cggctgctgt cctggcccct aggtgggcac agcagggtgg     960
aggggccaaa cccgacaatc ctctcagtgg ttctgtcatc caggacaggg cccagttcac    1020
tgttacctgt gtcctgccag aaccaagccc agtggagcct tcgggcatct tcccctaagg    1080
cctgtgttcc gaggagactt ataccagga ggctcaccaa aataagaacc aacagttccg     1140
ttttttcagt ttggcctgtc tgctggacct gttccaaaaa ggagcgccta ttgggaaata    1200
gctaacactg gacaaaatcc accatgacac ctgggtcccc ttgtgtgcag cttggaatga    1260
ccatttttac ttgagagcac agtgtgtgca caaccttggc aagcatagct acctcttagc    1320
gccaggctca gttgccttca cctcggggtc agagacacat tttctcctgc cccttatgta    1380
cacatgcgtg tatatacaca agcacaggta caccctggcc ccaccctgta agatgaggca    1440
```

```
gggccaggga ggagtgggct aaagccaggt cccacctcat ctgtcctcag cactgttgtc    1500
ctgcttgggg ctggcctcgg tggctggtta acgtctcagg agagcagcta tgtgtaataa    1560
agagcctcca cgctcaggtc tcctgtctt                                      1589
```

```
<210> SEQ ID NO 20
<211> LENGTH: 19
<212> TYPE: RNA
<213> ORGANISM: Artificial Sequence
<220> FEATURE:
<223> OTHER INFORMATION: A synthetic si-Control for Example 12 (1st
      strand)

<400> SEQUENCE: 20
gcaacaguca guccgucua                                                 19

<210> SEQ ID NO 21
<211> LENGTH: 19
<212> TYPE: RNA
<213> ORGANISM: Artificial Sequence
<220> FEATURE:
<223> OTHER INFORMATION: A synthetic si-Control for Example 12 (2nd
      strand)

<400> SEQUENCE: 21
uagacggacu gacuguugc                                                 19

<210> SEQ ID NO 22
<211> LENGTH: 25
<212> TYPE: RNA
<213> ORGANISM: Artificial Sequence
<220> FEATURE:
<223> OTHER INFORMATION: A synthetic si-ZO-2 #2 for Example 12 (1st
      strand)

<400> SEQUENCE: 22
ccuaaagcug uggaccuguu gaauu                                          25

<210> SEQ ID NO 23
<211> LENGTH: 25
<212> TYPE: RNA
<213> ORGANISM: Artificial Sequence
<220> FEATURE:
<223> OTHER INFORMATION: A synthetic si-ZO-2 #2 for Example 12 (2nd
      strand)

<400> SEQUENCE: 23
aauucaacag guccacagcu uuagg                                          25

<210> SEQ ID NO 24
<211> LENGTH: 32
<212> TYPE: RNA
<213> ORGANISM: Artificial Sequence
<220> FEATURE:
<223> OTHER INFORMATION: A synthetic si-ZO-2 #3 for Example 12 (1st
      strand)

<400> SEQUENCE: 24
gcucuggcaa cuaaagaugg caaccugcac ga                                  32

<210> SEQ ID NO 25
<211> LENGTH: 32
<212> TYPE: RNA
<213> ORGANISM: Artificial Sequence
<220> FEATURE:
<223> OTHER INFORMATION: A synthetic si-ZO-2 #3 for Example 12 (2nd
``` strand)

<400> SEQUENCE: 25
ucgugcaggu ugccaucuuu aguugccaga gc                                         32

<210> SEQ ID NO 26
<211> LENGTH: 507
<212> TYPE: DNA
<213> ORGANISM: Artificial Sequence
<220> FEATURE:
<223> OTHER INFORMATION: A synthetic guanylate kinase (GUK) domain of
      ZO-2/TJP2

<400> SEQUENCE: 26
aagagacctg tggtcttatt tggccctata gcagatatag ccttggaaaa gttggcaaat        60
gagttaccgg acctgttcca aactgctaaa acggaaccaa agatgcagg atccgagaaa       120 tctagtgggg tggtccggtt aaatactgtg aggcaaatta ttgaacagga taagcatgca       180
ctattggatg tgactcctaa agctgtggac ctgttgaatt atactcagtg gttcccgatt       240 gtgattttt tcaacccaga ctctagacaa ggtgtcaaaa ccatgagaca gaggttgaat       300
ccaacatcca acaaaagttc tcggaagttg tatgatcaag ccaacaagct taagaaaacg       360
tgtgcacatc tttttacagc tactatcaac ctaaattcag ccaatgatag ctggtttggc       420
agcttgaagg acacaattca gcatcagcaa ggagaagcag tttgggtctc tgaaggaaag       480
atggaaggga tggatgatga ccctgaa                                          507

<210> SEQ ID NO 27
<211> LENGTH: 30
<212> TYPE: PRT
<213> ORGANISM: Artificial Sequence
<220> FEATURE:
<223> OTHER INFORMATION: A synthetic guanylate kinase (GUK) domain of
      PSD-95 (A534 to V563)

<400> SEQUENCE: 27

Ala Arg Pro Ile Ile Ile Leu Gly Pro Thr Lys Asp Arg Ala Asn Asp
1               5                   10                  15

Asp Leu Leu Ser Glu Phe Pro Asp Lys Phe Gly Ser Cys Val
            20                  25                  30

<210> SEQ ID NO 28
<211> LENGTH: 112
<212> TYPE: PRT
<213> ORGANISM: Artificial Sequence
<220> FEATURE:
<223> OTHER INFORMATION: A synthetic guanylate kinase (GUK) domain of
      PSD-95 (V613 to L724)

<400> SEQUENCE: 28

Val Gln Ser Val Arg Glu Val Ala Glu Gln Gly Lys His Cys Ile Leu
1               5                   10                  15

Asp Val Ser Ala Asn Ala Val Arg Arg Leu Gln Ala Ala His Leu His
            20                  25                  30

Pro Ile Ala Ile Phe Ile Arg Pro Arg Ser Leu Glu Asn Val Leu Glu
        35                  40                  45

Ile Asn Lys Arg Ile Thr Glu Glu Gln Ala Arg Lys Ala Phe Asp Arg
    50                  55                  60

Ala Thr Lys Leu Glu Gln Glu Phe Thr Glu Cys Phe Ser Ala Ile Val
65                  70                  75                  80

Glu Gly Asp Ser Phe Glu Glu Ile Tyr His Lys Val Lys Arg Val Ile

```
                85                  90                  95
Glu Asp Leu Ser Gly Pro Tyr Ile Trp Val Pro Ala Arg Glu Arg Leu
            100                 105                 110

<210> SEQ ID NO 29
<211> LENGTH: 90
<212> TYPE: DNA
<213> ORGANISM: Artificial Sequence
<220> FEATURE:
<223> OTHER INFORMATION: A synthetic W199 zinc finger 3 domain (ZNF3) of
      Mus musculus Slug

<400> SEQUENCE: 29
acattgcctt gtgtctgcaa gatctgtggc aaggctttct ccagaccctg gctgcttcaa      60
ggacacatta gaactcacac tggggaaaag                                      90

<210> SEQ ID NO 30
<211> LENGTH: 80
<212> TYPE: PRT
<213> ORGANISM: Artificial Sequence
<220> FEATURE:
<223> OTHER INFORMATION: Synthetic Slug residues 186 to 265

<400> SEQUENCE: 30

Cys Val Cys Lys Ile Cys Gly Lys Ala Phe Ser Arg Pro Trp Leu Leu
1               5                  10                  15

Gln Gly His Ile Arg Thr His Thr Gly Glu Lys Pro Phe Ser Cys Pro
            20                  25                  30

His Cys Asn Arg Ala Phe Ala Asp Arg Ser Asn Leu Arg Ala His Leu
        35                  40                  45

Gln Thr His Ser Asp Val Lys Lys Tyr Gln Cys Lys Asn Cys Ser Lys
    50                  55                  60

Thr Phe Ser Arg Met Ser Leu Leu His Lys His Glu Glu Ser Gly Cys
65                  70                  75                  80

<210> SEQ ID NO 31
<211> LENGTH: 80
<212> TYPE: PRT
<213> ORGANISM: Artificial Sequence
<220> FEATURE:
<223> OTHER INFORMATION: Synthetic Zif268 residues 107 to 186

<400> SEQUENCE: 31

Cys Pro Val Glu Ser Cys Asp Arg Arg Phe Ser Gln Ser Gly Ser Leu
1               5                  10                  15

Thr Arg His Ile Arg Ile His Thr Gly Gln Lys Pro Phe Gln Cys Arg
            20                  25                  30

Ile Cys Met Arg Asn Phe Ser Arg Ser Asp His Leu Thr Thr His Ile
        35                  40                  45

Arg Thr His Thr Gly Glu Lys Pro Phe Ala Cys Asp Ile Cys Gly Arg
    50                  55                  60

Lys Phe Ala Arg Ser Asp Glu Arg Lys Arg His Thr Lys Ile His Leu
65                  70                  75                  80
```

MODULATING THE INTERACTION BETWEEN ZO-2/TJP2 AND A SNAIL ZINC FINGER TRANSCRIPTION FACTOR FAMILY MEMBER

CROSS-REFERENCE TO RELATED APPLICATIONS

This application is a U.S. national stage application filed under 35 U.S.C. § 371 from International Application Ser. No. PCT/SG2013/000080, which was filed Feb. 28, 2013, and published as WO 2013/130017 on Sep. 6, 2013, and which claims the benefit of priority of Singapore patent application no. 201201458-5, filed Feb. 29, 2012, which applications and publication are incorporated by reference as if reproduced herein and made a part hereof in their entirety, and the benefit of priority of each of which is claimed herein.

TECHNICAL FIELD

The present invention generally relates to the field of biotechnology. Specifically, it refers to the interaction between ZO-2/TJP2 and members of the Snail zinc finger transcription factor family.

BACKGROUND

Epithelia serve as the first line of defense of an organism that is constantly exposed to microbes, viruses and toxins. As a first line of defense, any open wound will need to be quickly repaired. Hence it will be advantageous for epithelial cells to be exposed to growth factors so that a quick encounter with these growth factors is possible when the integrity of the epithelial sheet is compromised. This will require such epithelial cells to position their growth factor receptors strategically on their surfaces.

The tight junction (TJ) is the topmost intercellular junction in epithelial cells that is linked to the regulation of paracellular permeability and signal transduction. The TJ is composed of membrane-associated guanylate kinase proteins (MAGUKs) that include Zonula Occluden proteins (ZO-1, ZO-2 and ZO-3). These proteins have been shown to contain nuclear sorting signals and are capable of shuttling between the membrane and nucleus depending on cell density.

In particular, ZO-2 has been shown to be capable of shuttling between the nucleus and cytoplasm. In sparse Madin-Darby Canine Kidney (MDCK) cell cultures, ZO-2 tends to accumulate in the nucleus. In addition, when pig kidney epithelial cells were subjected to environmental stress or growth at 42° C., an increased nuclear staining of ZO-2 was observed. Furthermore, in some tumor cells, TJ proteins were also found inside the nucleus. It has been found that ZO-2 may function as a tumor suppressor by blocking cell cycle progression at the transcription and protein level. Support for the role of ZO-2 as a tumor suppressor also comes from observations that its expression is either lost or decreased in a majority of breast cancer cell lines and adenocarcinomas.

Accordingly, it appears that ZO proteins have been found to translocate to the nucleus when epithelial cells are subjected to external stress such as mechanical injury, heat shock and chemical insults. However, the biological relevance of this accumulation of ZO-2 in the nucleus under such circumstances has however remained somewhat elusive.

Slug is a member of the Snail superfamily of zinc finger transcription factors. Snail and Slug were shown to elicit epithelial-to-mesenchymal transition (EMT) through the direct repression of E-cadherin expression. This process is critical in developmental processes such as gastrulation, neural crest cell migration, organogenesis, as well as in the metastasis of tumors derived from epithelial tissues. EMT is also linked to wound healing, fibroblastic remodeling in mature tissues after injury and tubulogenesis. Hence, studying the mechanisms that regulate the Snail superfamily of transcription factors is important.

There is therefore a need to establish a relationship between ZO-2 and the Snail superfamily of transcription factors and uses for such a relationship.

SUMMARY

In a first aspect, there is provided a method of identifying candidate agents capable of modulating interaction between a first polypeptide and a second polypeptide, wherein the first polypeptide is ZO-2/TJP2 or a functional variant thereof and the second polypeptide is a Snail zinc finger transcription factor family member or a functional variant thereof, the method comprising: a. contacting the first polypeptide with the second polypeptide and a candidate agent; and b. determining whether: i. the binding of the first polypeptide with the second polypeptide is decreased or increased in the presence of said candidate agent when compared with a control; or ii. whether the affinity, extent or amount of the binding between the first polypeptide and the second polypeptide is decreased or increased in the presence of said candidate agent when compared with a control.

In a second aspect, there is provided a method of predicting the likelihood of tumor metastasis development or the effectiveness of a cancer treatment, the method comprising determining a change in: a. the binding of a first polypeptide with a second polypeptide when compared with a control; or b. the affinity, extent or amount of the binding between a first polypeptide and a second polypeptide when compared with a control; wherein the first polypeptide is ZO-2/TJP2 or a functional variant thereof and the second polypeptide is a Snail zinc finger transcription factor family member or a functional variant thereof.

In a third aspect, there is provided a kit for identifying candidate agents capable of modulating the interaction between a first polypeptide and a second polypeptide, wherein the first polypeptide is ZO-2/TJP2 or a functional variant thereof and the second polypeptide is a Snail zinc finger transcription factor family member or a functional variant thereof, the kit comprising the first polypeptide, the second polypeptide and at least one candidate agent.

In a fourth aspect, there is provided a method of treating, inhibiting or suppressing tumor growth comprising: administering an agent which decreases the binding of a first polypeptide and a second polypeptide, wherein the first polypeptide is ZO-2/TJP2 or a functional variant thereof and the second polypeptide is a Snail zinc finger transcription factor family member or a functional variant thereof.

In a fifth aspect, there is provided a method of inhibiting tumor metastasis comprising: administering an agent which decreases the binding of a first polypeptide and a second polypeptide, wherein the first polypeptide is ZO-2/TJP2 or a functional variant thereof and the second polypeptide is a Snail zinc finger transcription factor family member or a functional variant thereof.

In a sixth aspect, there is provided a method of enhancing wound healing comprising: administering an agent which increases the binding of a first polypeptide and a second polypeptide, wherein the first polypeptide is ZO-2/TJP2 or a functional variant thereof and the second polypeptide is a Snail zinc finger transcription factor family member or a functional variant thereof.

In a seventh aspect, there is provided an isolated complex between ZO-2/TJP2 and a Snail zinc finger transcription factor family member.

In an eighth aspect, there is provided the use of the isolated complex as defined herein as a biomarker for detecting cancer.

In a ninth aspect, there is provided an antibody directed against the binding portion of ZO-2/TJP2 and SNAI2 (Slug) at the guanylate kinase (GUK) domain of ZO-2/TJP2.

DETAILED DESCRIPTION

It has now been discovered that nuclear ZO-2 directly interacts with the Snail superfamily of zinc finger transcription factors. In particular, the interaction of ZO-2 with a Snail zinc finger transcription factor enhances the nuclear retention of the ZO-2/Snail complex and hence protection from proteasomal degradation. It has been found that during early stages of epithelial-to-mesenchymal transition (EMT), nuclear translocation of ZO-2 may sequester Slug into the nucleus, which would then trigger a full or partial EMT to enhance migratory properties of cells by down-regulating epithelial markers. As it has been found that Slug and SNAI1 (Snail) were capable of down-regulating many epithelial markers, the entry of ZO-2 into the nucleus may serve to feed-forward a positive feedback loop that favored the initiation of a full or partial EMT.

This finding may allow for the synthesis of small drug targets that can be used to modulate this interaction between ZO-2 and Slug or any members of the Snail superfamily. With the discovery that the ZO-2/Snail complex possesses enhanced nuclear retention, it is now possible to tailor a method to modulate the interaction between ZO-2 and a Snail zinc finger transcription factor to exploit the effects of these proteins when bound.

Accordingly, there is provided a method of identifying candidate agents capable of modulating interaction between a first polypeptide and a second polypeptide, wherein the first polypeptide is ZO-2/TJP2 or a functional variant thereof and the second polypeptide is a Snail zinc finger transcription factor family member or a functional variant thereof. The method can comprise the step of a. contacting the first polypeptide with the second polypeptide and a candidate agent. The method can also comprise the step of b. determining whether: i. the binding of the first polypeptide with the second polypeptide is decreased or increased in the presence of said candidate agent when compared with a control; or ii. whether the affinity, extent or amount of the binding between the first polypeptide and the second polypeptide is decreased or increased in the presence of said candidate agent when compared with a control.

As used in the context of the specification, the term "ZO-2" refers to the protein Zonula Occludens-2, also known as tight junction protein 2 (TJP2). Hence, the terms "ZO-2" and "ZO-2/TJP2" as used in the specification are interchangeable, unless indicated otherwise.

In some instances, the first polypeptide comprises ZO-2/TJP2 including, but not limited to, SEQ ID NO: 1, SEQ ID NO: 2, SEQ ID NO: 3, SEQ ID NO: 4, SEQ ID NO 5, SEQ ID NO: 6, SEQ ID NO: 7, SEQ ID NO: 8 and SEQ ID NO: 9. The different sequences for ZO-2/TJP2 arise due to the different isoforms of the protein derived from different organisms.

The ZO-2/TJP2 may be derived from any organism as long as the ZO-2/TJP2 derived therefrom possesses the guanylate kinase (GUK) domain. The different organisms include, but are not limited to, humans, mouse and canines. In one example, the different organisms come from the genus including, but not limited to, *Canis, Mus* and *Homo*. In another example, the different organisms include, but are not limited to, *Canis lupus familiaris, Mus musculus* and *Homo sapiens*.

In some instances, the first polypeptide comprises ZO-2/TJP2 derived from *Homo Sapiens* including, but not limited to, SEQ ID NO: 4, SEQ ID NO: 5, SEQ ID NO: 6, SEQ ID NO: 7, SEQ ID NO: 8 and SEQ ID NO: 9. In other instances, the first polypeptide comprises ZO-2/TJP2 derived from *Mus musculus* including, but not limited to, SEQ ID NO: 2 and SEQ ID NO: 3. In yet another instance, the first polypeptide comprises ZO-2/TJP2 derived from *Canis lupus familiaris* including, but not limited to, SEQ ID NO: 1.

In some instances, the ZO-2/TJP2 may be artificially created as study models. In other instances, the ZO-2/TJP2 may be derived from *Homo sapiens* for clinical studies and therapeutic applications.

The Snail superfamily is divided into two families, namely Snail and Scratch. The Snail family is further branched into the Snail and Slug subfamilies. Smuc is a more recent isolate in the family tree of the Snail superfamily. As used in the context of the specification, the terms "Snail zinc finger transcription factors" and "Snail superfamily of zinc finger transcription factors", or variants thereof, are interchangeable, unless indicated otherwise. The term "Snail" as used in the context of the specification refers to any one of the members of the Snail superfamily of zinc finger transcription factors, unless otherwise indicated.

In instances, the second polypeptide comprises a Snail zinc finger transcription factor family member including, but not limited to, SNAI1 (Snail), SNAI2 (Slug), SNAI3 (Smuc), Scratch 1 and Scratch 2. The Snail zinc finger transcription factor family member may be derived from different organisms. The different organisms include, but are not limited to, humans, mouse and canines. In one example, the different organisms come from the genus including, but not limited to, *Canis, Mus* and *Homo*. In another example, the different organisms include, but are not limited to, *Mus musculus* and *Homo sapiens*. The Snail zinc finger transcription factor family member may be derived from any organism as long as the Snail zinc finger transcription factor family member derived therefrom possesses the binding domain exemplified by the tryptophan (W) amino acid in position 199 of the zinc finger 3 of *Mus musculus* Slug or the equivalent zinc finger domain of other Snail family members.

In instances, the second polypeptide comprises a Snail zinc finger transcription factor family member including, but not limited to, SNAI1 (Snail) and SNAI2 (Slug). In instances, the second polypeptide comprises a Snail zinc finger transcription factor family member including, but not limited to, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18 and SEQ ID NO: 19.

In an example, SNAI1 (Snail) includes, but is not limited to, SEQ ID NO: 12 and SEQ ID NO: 13. In another example, SNAI2 (Slug) includes, but is not limited to, SEQ ID NO: 10 and SEQ ID NO: 11. In yet another example, SNAI3 (Smuc)

includes, but is not limited to, SEQ ID NO: and SEQ ID NO: 19. In another example, Scratch 1 includes, but is not limited to, SEQ ID NO: 14 and SEQ ID NO: 16. In yet another example, Scratch 2 includes, but is not limited to, SEQ ID NO: 15 and SEQ ID NO: 17. In another example, the second polypeptide comprises a Snail zinc finger transcription factor family member derived from *Homo sapiens* including, but not limited to, SEQ ID NO: 11, SEQ ID NO: 12, SEQ ID NO: 14, SEQ ID NO: 15 and SEQ ID NO: 18. In yet another example, the second polypeptide comprises a Snail zinc finger transcription factor family member derived from *Mus musculus* including, but not limited to, SEQ ID NO: 10, SEQ ID NO: 13, SEQ ID NO: 14, SEQ ID NO: 15 and SEQ ID NO: 18.

In some instances, the Snail zinc finger transcription factor family member may be artificially created as study models. In other instances, the Snail zinc finger transcription factor family member may be derived from *Homo sapiens* for clinical studies and therapeutic applications.

A "functional variant" of a polypeptide describes a polypeptide which has at one or more positions an amino acid insertion, deletion, or substitution, either conservative or non-conservative, and wherein each of these types of changes may occur alone, or in combination with one or more of the others, one or more times in a given sequence. Preferably, a "functional variant" has at least 80%, 82%, 85%, 87%, 90%, 92%, 95%, 97%, 98%, 99% or 99.5% sequence identity (optionally determined using Clustal W algorithm with the alignment default parameters, and default parameters) with the reference polypeptide.

The term "conservative" when used to describe variants or substitutions denotes the replacement of an amino acid residue by another, biologically similar residue with respect to hydrophobicity, hydrophilicity, cationic charge, anionic charge, shape, polarity and the like. Examples of conservative substitutions include the substitution of one hydrophobic residue such as isoleucine, valine, leucine, alanine, cysteine, glycine, phenylalanine, proline, tryptophan, tyrosine, norleucine or methionine for another, or the substitution of one polar residue for another, such as the substitution of arginine for lysine, glutamic acid for aspartic acid, or glutamine for asparagine, and the like. Neutral hydrophilic amino acids, which can be substituted for one another, include asparagine, glutamine, serine and threonine. The term "conservative substitution" also includes the use of a substituted or modified amino acid in place of an unsubstituted parent amino acid provided that substituted peptide reacts with hK2. By "substituted" or "modified", the present invention includes those amino acids that have been altered or modified from naturally occurring amino acids. The term "non-conservative" will be construed accordingly.

In some instances, the first polypeptide is a functional variant of ZO-2/TJP2. The functional variant of the first polypeptide may have at least 80%, or at least 82%, or at least 85%, or at least 87%, or at least 90%, or at least 92%, or at least 95%, or at least 97%, or at least 98%, or at least 99%, or at least 99.5% sequence identity with ZO-2/TJP2. In one example, the functional variant of ZO-2/TJP2 has at least 80% sequence identity with said ZO-2/TJP2.

In some instances, the second polypeptide is a functional variant of the Snail zinc finger transcription factor family member. The functional variant of the second polypeptide may have at least 80%, or at least 82%, or at least 85%, or at least 87%, or at least 90%, or at least 92%, or at least 951, or at least 97%, or at least 98%, or at least 99%, or at least 99.5% sequence identity with the Snail zinc finger transcription factor family member. In one example, the functional variant of the Snail zinc finger transcription factor family member has at least 80% sequence identity with said Snail zinc finger transcription factor family member.

The term "interaction" as used herein is to be interpreted broadly to mean coupling of two molecules via non-covalent bonding, covalent bonding, electrostatic interactions due to hydrogen bonding or van der Waals forces, and non-electrostatic interactions due to hydrophobic effects. The term "interaction" also includes hybridization which is a complementary bonding between nucleic acids (nucleotide chains), for example.

It has been found that the interaction between the first polypeptide and the second polypeptide occurs in the guanylate kinase (GUK) domain of ZO-2/TJP2. In some instances, the binding occurs in the hydrophobic pocket formed by the region between helix 8 (N848 D849 F852) and helix 2 (I726 A727) of the GUK domain of *Canis lupus familiaris* ZO-2/TJP2. In other instances, the binding occurs in the equivalent hydrophobic pocket of the GUK domain of ZO-2/TJP2 from a species other than *Canis lupus familiaris*, such as in members of the genus *Homo* and *Mus*.

In one example, the interaction between the first polypeptide and the second polypeptide occurs in the guanylate kinase (GUK) domain of ZO-2/TJP2 comprising SEQ ID NO: 26.

In some instances, the GUK domain of postsynaptic density protein 95 (PSD-95) is A534 to V563 (SEQ ID NO: 27), and V613 to L724 (SEQ ID NO: 28). The classification of other domains of postsynaptic density protein 95 (PSD-95) include, but is not limited to, SH3 Domain (G430 to K503), HOOK Domain (W507 to Y533), GUK domain (A534 to V563, V613 to L724) and NMP Domain (part of GUK domain) (P564 to S612). In some instances, the GUK domain may comprise of the region between helix 8 (N848 D849 F852) and helix 2 (I726 A727).

In some instances, a portion of Snail interacts with ZO-2. In one example, the ring side chain of the tryptophan (W) amino acid in position 199 interacts with the GUK domain. In another example, the ring side chain of W199 of Snail interacts with the residues N848, D849, F852, I1726 and A727 of ZO-2.

In some instances, the interaction occurs at the tryptophan (W) amino acid in position 199 of the zinc finger 3 domain (ZNF3) (SEQ ID NO: 29) of *Mus musculus* Slug. In other instances, the interaction occurs at W198 in *Homo sapiens* Slug. In other instances, the binding occurs in the corresponding zinc finger domain of another Snail family member.

It has also been found that there is no association of members of the Snail zinc finger transcription factor family member, e.g. Slug, with either the protein Zonula Occludens-1 (ZO-1) or Zonula Occludens-3 (ZO-3).

The term "contacting" refers to the act of touching, making contact, or of bringing to immediate or close proximity, including at the cellular or molecular level, for example, to bring about a physiological reaction, a chemical reaction, or a physical change, e.g., in a solution or in any reaction mixture, including a 'neat' mixture of reactants. In instances where the first polypeptide, second polypeptide and candidate agent are in the form of a solution, the contacting step is performed by mixing the solutions comprising one or more of the first polypeptide, second polypeptide and candidate agent.

In instances, the first and second polypeptides and the candidate agent are contacted with each other under conditions wherein, in the absence of the candidate agent, the first and second polypeptide are able to bind with each other. In some instances, in vitro binding conditions include, but are not restricted to, about 4° C. to about 37° C. In an example, in vitro binding conditions include, but are not restricted to: 4° C., 3 h, PBS with 1% TX-100, 1 mM EDTA, complete EDTA free protease inhibitor cocktail, 1 mM DTT, 300 µg/ml Benzamidine. Binding is also known to occur in vivo in, for example, yeast and mammalian cells.

The first polypeptide, second polypeptide and the candidate agent may be contacted in any order, or simultaneously. In some instances, the first polypeptide, the second polypeptide and the candidate agent are contacted separately or simultaneously. In one example, the first and second polypeptides are contacted simultaneously, followed by the candidate agent. In another example, the first polypeptide and the candidate agent are contacted simultaneously, followed by the second polypeptide. In another example, the second polypeptide and the candidate agent are contacted simultaneously, followed by the first polypeptide.

The term "candidate agent" as used in the context of the specification refers to any molecule that is capable of modulating interaction between the first polypeptide and the second polypeptide. The terms "candidate agent", "test compound", "agent" and "drug target" are used interchangeably in the context of the specification. In some instances, the candidate agent includes, but is not limited to: small organic or inorganic molecules (e.g. having a molecular weight less than 1 kDa, or more preferably less than 500 Da), aptamers, polypeptides, nucleic acids, antibodies (including fragments thereof), phospholipids and other lipid derivatives.

As used in the context of the specification, the term "modulation", or grammatical variants thereof, refers to up-regulation (i.e., activation or stimulation), down-regulation (i.e., inhibition or suppression) of a biological activity, or the two in combination or apart. Modulation includes, for example, an effect due to competition or steric hindrance by binding of a compound to the interacting regions or vicinity, or by binding of the compound to other regions and affecting conformation or structure and thereby binding.

Accordingly, in some instances, the candidate agent may either up-regulate or down-regulate interaction between the first polypeptide and the second polypeptide when compared to a control. An up-regulation of the interaction promotes the interaction, while a down-regulation of the interaction inhibits the interaction. In some instances, the candidate agent is an agonist of the interaction between the first polypeptide and the second polypeptide, thereby up-regulating the interaction. In other instances, the candidate agent is an antagonist of the interaction between the first polypeptide and the second polypeptide, thereby down-regulating the interaction.

In instances where the binding of the first polypeptide and the second polypeptide is decreased in the presence of the candidate agent, the candidate agent down-regulates the interaction. In such instances, the candidate agent is considered an antagonist of the interaction. In instances where the binding of the first polypeptide and the second polypeptide is increased in the presence of the candidate agent, the candidate agent up-regulates the interaction. In such instances, the candidate agent is considered an agonist of the interaction. A decrease or increase in the binding between the first and second polypeptide may be determined in relation to a control in which the candidate agent is absent. Accordingly, a control assay may also be performed to provide a baseline for comparison.

In instances where the binding of the first polypeptide and the second polypeptide is decreased in the presence of the candidate agent, the affinity of the binding of the first and second polypeptides is decreased. In instances where the binding of the first polypeptide and the second polypeptide is increased in the presence of the candidate agent, the affinity of the binding of the first and second polypeptides is increased.

Similarly, in instances where the binding of the first polypeptide and the second polypeptide is decreased in the presence of the candidate agent, the amount of the binding of the first and second polypeptides is decreased. In instances where the binding of the first polypeptide and the second polypeptide is increased in the presence of the candidate agent, the amount of the binding of the first and second polypeptides is increased.

Further, in instances where the binding of the first polypeptide and the second polypeptide is decreased in the presence of the candidate agent, the extent of the binding of the first and second polypeptides is decreased. In instances where the binding of the first polypeptide and the second polypeptide is increased in the presence of the candidate agent, the extent of the binding of the first and second polypeptides is increased.

The affinity, extent or amount of the binding may be determined by the dissociation constant, $K_D$. The dissociation constant varies depending on the assay method used. An example of a method to measure the dissociation constant is Surface Plasmon Resonance (SPR, for example BiaCore). In the SPR technique, one binding partner is coupled to a sensor chip and then binding and dissociation of the second partner (either alone or in presence of an antagonist or agonist) is measured in real time. The complex can also be coupled and the dissociation determined in real time after addition of the antagonist or agonist. Other examples of assay methods to determine the dissociation constant include, but are not limited to, quantification by fluorimetry, flow cytometry, Fluorescence Resonance Energy Transfer (FRET), titration calorimetry or fluorescence polarization.

The dissociation constant of ZO-2/TJP2 and Snail, in the absence of the candidate agent, may be anywhere from about $10^{-9}$M to about $10^{-3}$M when compared to the dissociation constant of a control. The control may be, for example, a Slug mutant lacking a ZNF3 domain or a Slug mutant having a W199A mutation. The dissociation constant of ZO-2/TJP2 and Snail may increase in the presence of a candidate agent that is an agonist. Alternatively, the dissociation constant of ZO-2/TJP2 and Snail may decrease in the presence of a candidate agent that is an antagonist.

The change of affinity, extent or amount of the binding may be determined by a method including, but not limited to, a yeast two-hybrid system, a glutathione S-transferase (GST) binding assay, immunoprecipitation, immunofluorescence and combinations thereof. In other instances, a change in the binding is determined by a method including, but not limited to, a yeast two-hybrid system, a glutathione S-transferase (GST) binding assay, immunoprecipitation, immunofluorescence and combinations thereof.

In some instances, the candidate agent may have no effect on the interaction between the first polypeptide and the second polypeptide. That is, the binding between the first polypeptide and the second polypeptide are neither increased nor decreased in the presence of the candidate agent as compared to when the candidate agent is absent.

Since the interacting domains of Slug and ZO-2 have been identified, it is envisioned that test compounds modeled from these domains can be used as specific agonists or antagonists. In some instances, a test compound that inhibits the interaction between ZO-2 and Snail decreases their binding. In other instances, a test compound that promotes the interaction between ZO-2 and Snail increases their binding. In some instances, a test compound that decreases the binding of ZO-2 and Snail possesses an aromatic ring similar to that in tryptophan. A fragment or peptide of Snail containing tryptophan at amino acid position 199 and that binds to ZO-2 may be an example of a candidate agent. An example of a fragment of Snail is the ZNF 3 domain as it is the smallest domain capable of binding to ZO-2, thereby interfering the interaction between Snail and ZO-2.

As mentioned above, epithelial-to-mesenchymal transition (EMT) is linked to wound healing and an increase in the binding of ZO-2 with Snail triggers EMT. In particular, it has been found that wounding the cell monolayer concurrently raises the levels of nuclear ZO-2 and Slug, whilst closure of the wound leads to the diminishing of ZO-2 in the nucleus and the rapid degradation of Slug. Thus, the shuttling of ZO-2 into the nucleus at the wound edge could serve to stabilize Slug by nuclear sequestration, thereby making Slug less prone to proteasomal degradation.

In an example, an increase in the binding of the first polypeptide and the second polypeptide indicates that the candidate agent is useful for enhancing wound healing. The term "wound" as used herein is to be interpreted broadly to include, but is not limited to, a cut or tear in tissue (lacerations) such as a surgical incision, a catheter insertion sit or a medical implants site, scrapes (abrasions), punctures caused by bites or other injuries, trauma or burn. Hence, in some instances, the candidate agent is useful for promoting the healing of wounds.

Further, as mentioned above, the finding that the ZO-2/Snail complex possesses enhanced nuclear retention may allow for the synthesis of small drug targets that can be used to modulate this interaction between ZO-2 and Slug or any members of the Snail superfamily, thus leading to a more favorable prognosis for cancer patients.

Based on this discovery, in an example, a decrease in the binding of the first polypeptide and the second polypeptide indicates that the candidate agent is useful for treating cancer.

A cancer is a group of cells (usually derived from a single cell) that has lost its normal control mechanisms and thus has unregulated growth. Cancerous (malignant) cells can develop from any tissue within any organ. As cancerous cells grow and multiply, they form a mass of cancerous tissue, called a tumor, that invades and destroys normal adjacent tissues. The term "tumor" refers to an abnormal growth or mass; tumors can be cancerous or noncancerous. Cancerous cells from the primary (initial) site can spread (metastasize) throughout the body. In some instances, the cancer includes, but is not limited to, lung cancer, breast cancer, metastatic breast cancer, cervical cancer, colorectal carcinoma, liver cancer, head and neck cancer, pancreatic cancer, gastric cancer, prostate cancer, renal cancer, sarcoma, multiple myeloma, leukemia, lymphoma, esophageal cancer, brain tumor, glioma, bladder cancer, endometrial cancer, thyroid cancer, bile duct cancer, bone cancer, eye cancer (retinoblastoma), gallbladder cancer, pituitary cancer, rectal cancer, salivary gland cancer, and nasal pharyngeal cancer. In other instances, the cancer includes, but is not limited to, colon carcinoma, chondrosarcoma, breast cancer and adenocarcinoma.

In another example, a decrease in the binding of the first polypeptide and the second polypeptide indicates that the candidate agent is useful for inhibiting tumor metastasis.

In an embodiment, there is provided a method of predicting the likelihood of tumor metastasis development or the effectiveness of a cancer treatment. The method may comprise the step of determining a change in: a. the binding of first polypeptide with a second polypeptide when compared with a control; or b. the affinity, extent or amount of the binding between a first polypeptide and a second polypeptide when compared with a control; wherein the first polypeptide is ZO-2/TJP2 or a functional variant thereof and the second polypeptide is a Snail zinc finger transcription factor family member or a functional variant thereof.

As mentioned above, the binding of the first polypeptide and the second polypeptide enhances the nuclear retention of the ZO-2/Snail complex. Accordingly, a change in the binding of the first polypeptide and the second polypeptide when compared with a control indicates a change in the localization of the ZO-2/Snail complex.

The method may comprise the step of obtaining a biological sample. The biological sample may be tumor cells, such as from a tumor biopsy or circulating tumor cells from the patient. An assay may be performed to determine localization of ZO-2 or Snail or ZO-2/Snail complex in the sample. The localization may be, for example, nuclear, cytosolic or membrane localization.

In an example, the method includes, but is not limited to, a yeast two-hybrid system, a glutathione S-transferase (GST) binding assay, immunoprecipitation, immunofluorescence and combinations thereof.

A change in affinity, extent or amount of binding can be determined, for example, in vitro or in vivo. For example, a change in affinity, extent or amount may be determined by: (a) labeling one of the polypeptides, e.g. with fluorescence or antibodies etc; (b) contacting the labeled polypeptide with the other polypeptide which is immobilized, e.g. to a solid surface such as well plates. A change in affinity, extent or amount induced by a candidate agent will result in a decrease in fluorescence intensity if the agent disrupts binding.

The method may further comprise the step of comparing the localization of the ZO-2/Snail complex in the sample with an appropriate control, e.g. one or more samples from one or more individuals who do not have tumor cells or who do not have metastatic tumor cells.

Alternatively, most biopsies of patients will include tumor tissue as well as surrounding normal tissue, the latter providing an appropriate control.

In some instances, an increase in the binding of the first polypeptide and the second polypeptide indicates an increase in tumor metastasis development. That is, if the nuclear localization or cytosolic localization is determined to be greater than the level in the control sample due to the increase in binding, then the patient has an increased likelihood of developing a metastatic condition. Alternatively, if the membrane localization is determined to be less than the level in a control sample, then the patient has an increased likelihood of developing a metastatic condition. In other instances, an increase in the binding of the first polypeptide and the second polypeptide indicates a decrease in effectiveness in cancer treatment.

The cytosolic localization, or nuclear localization, or membrane localization, or combinations thereof, may be used as a biomarker or diagnostic tool to detect cancer or tumor metastasis.

Further, since metastasis is a late event in carcinogenesis, the cytosolic localization, or nuclear localization, or membrane localization, or combinations thereof may also be used as a biomarker to grade a tumor. Alternatively, the cytosolic localization, or nuclear localization, or membrane localization, or combinations thereof may also be used to predict the outcome of a treatment (e.g. tumor treatment). The use of biomarkers as disclosed herein may optionally comprise their use as biomarkers in combination with one or more other markers.

In some instances, a decrease in the binding of the first polypeptide and the second polypeptide indicates a decrease in tumor metastasis development. In other instances, a decrease in the binding of the first polypeptide and the second polypeptide indicates an increase in effectiveness in cancer treatment.

Determining the likelihood of tumor metastasis development or the effectiveness of a cancer treatment is of great value to the medical practitioner. For example, low effectiveness of a cancer treatment means that a longer or higher dose treatment should be given, and the patient should be more closely monitored for signs of recurrence of the cancer. An accurate prognosis is also of benefit to the patient. It allows the patient, along with their partners, family, and friends to also make decisions about treatment, as well as decisions about their future and lifestyle changes.

In one embodiment, there is provided a kit for identifying candidate agents capable of modulating the interaction between a first polypeptide and a second polypeptide, wherein the first polypeptide is ZO-2/TJP2 or a functional variant thereof and the second polypeptide is a Snail zinc finger transcription factor family member or a functional variant thereof. The kit may comprise the first polypeptide, the second polypeptide and at least one candidate agent.

In an example, the at least one candidate agent may be a library of candidate agents.

In one embodiment, there is provided a method of treating, inhibiting or suppressing tumor growth. The method may comprise the step of administering an agent which decreases the binding of a first polypeptide and a second polypeptide, wherein the first polypeptide is ZO-2/TJP2 or a functional variant thereof and the second polypeptide is a Snail zinc finger transcription factor family member or a functional variant thereof.

The term "inhibiting" refers to barring the organism from acquiring the abnormal condition, while the term "treating" refers to a method of alleviating or abrogating the abnormal condition in the organism. The term "suppressing" refers to reducing the possibility of the organism from acquiring the abnormal condition.

In one embodiment, there is provided a method of inhibiting tumor metastasis. The method may comprise the step of administering an agent which decreases the binding of a first polypeptide and a second polypeptide, wherein the first polypeptide is ZO-2/TJP2 or a functional variant thereof and the second polypeptide is a Snail zinc finger transcription factor family member or a functional variant thereof.

In one embodiment, there is provided a method of enhancing wound healing. The method may comprise the step of administering an agent which increases the binding of a first polypeptide and a second polypeptide, wherein the first polypeptide is ZO-2/TJP2 or a functional variant thereof and the second polypeptide is a Snail zinc finger transcription factor family member or a functional variant thereof.

The agent may be administered in combination with cancer therapies, either separately or simultaneously. In some instances, the agent can be used in combination with conventional cancer therapies or pharmaceutical formulations useful for treating cancer. These treatments can include surgical procedures, radiation therapy and/or ablation therapy (e.g., laser therapy, infrared therapy and the like). Cancer therapies including dendritic cell therapy, chemokines, cytokines, tumor necrosis factors (e.g., TNF-α), chemotherapeutic agents (e.g., adenosine analogs (e.g., cladribine, pentostatin), alkyl sulfanates (e.g., busulfan)), anti-tumoral antibiotics (e.g., bleomycin, dactinomycin, daunorubicin, doxorubicin, epirubicin, idarubicin, mitoxantrone, mitomycin), aziridines (e.g., thiotepa), camptothecin analogs (e.g., irinotecan, topotecan), cryptophycins (e.g., cryptophycin 52, cryptophicin 1), dolastatins (e.g., dolastatin 10, dolastatin 15), enedyine anticancer drugs (e.g., esperamicin, calicheamicin, dynemicin, neocarzinostatin, neocarzinostatin chromophore, kedarcidin, kedarcidin chromophore, C-1027 chromophore, and the like), epipodophyllotoxins (e.g., etoposide, teniposide), folate analogs (e.g., methotrexate), maytansinoids (e.g., maytansinol and maytansinol analogues), microtubule agents (e.g., docetaxel, paclitaxel, vinblastine, vincristine, vinorelbine), nitrogen mustards (e.g., chlorambucil, cyclophosphamide, estramustine, if osf amide, mechlorethamine, melphalan), nitrosoureas (e.g., carmustine, lamustine, streptoxacin), nonclassic alkylators (e.g., altretamine, dacarbazine, procarbazine, temozolamide), platinum complexes (e.g., carboplatin, cisplatin), purine analogs (e.g., fludarabine, mercaptopurine, thioguanine), pyrimidine analogs (e.g., capecitabine, cytarabine, depocyt, floxuridine, fluorouracil, gemcitabine), substituted ureas (e.g., hydroxyurea)]; anti-angiogenic agents (e.g., canstatin, troponin I,), biologic agents (e.g., ZD 1839, virulizin and interferon), antibodies and fragments thereof (e.g., anti EGFR, anti-HER-2/neu, anti-KDR, 1MC-C225), anti-emetics (e.g., lorazepam, metroclopramide, and domperidone), epithelial growth factor inhibitors (e.g., transforming growth factor beta 1), anti-mucositic agents (e.g., dyclonine, lignocaine, azelastine, glutamine, corticoid steroids and allopurinol), anti-osteoclastic agents (e.g., bisphosphonates {e.g., etidronate, pamidronate, ibandronate, and osteoprotegerin}), hormone regulating agents (e.g., anti-androgens, LHRH agonists, anastrozole, tamoxifen), hematopoietic growth factors, anti-toxicity agents (e.g., amifostine), kinase inhibitors (gefitinib, imatinib), and mixtures of two or more thereof.

In one embodiment, there is provided an isolated complex between ZO-2/TJP2 and a Snail zinc finger transcription factor family member. The Snail zinc finger transcription factor family member may be any member of the Snail zinc finger transcription factor family. In one example, the Snail zinc finger transcription factor family member is SNAI2 (Slug).

The binding portion is as disclosed herein. In some instances, the binding portion of ZO-2/TJP2 and SNAI2 (Slug) is at the guanylate kinase (GUK) domain of ZO-2/TJP2. In an example, the guanylate kinase (GUK) domain of ZO-2/TJP2 comprises SEQ ID NO: 26.

In an embodiment, there is provided the use of the isolated complex as defined herein as a biomarker. In an example, the biomarker may be used for detecting cancer. In another example, the biomarker may be used for grading tumors. In yet another example, the biomarker may be used for tumor metastasis. In another example, the biomarker may be used for predicting the outcome of a treatment (e.g. tumor treatment).

In an embodiment, there is provided an antibody directed against the binding portion of ZO-2/TJP2 and SNAI2 (Slug) at the guanylate kinase (GUK) domain of ZO-2/TJP2. In an example, the guanylate kinase (GUK) domain of ZO-2/TJP2 comprises SEQ ID NO: 26.

Unless specified otherwise, the terms "comprising" and "comprise", and grammatical variants thereof, are intended to represent "open" or "inclusive" language such that they include recited elements but also permit inclusion of additional, unrecited elements.

As used herein, the term "about", in the context of concentrations of components of the formulations, typically means +/−5% of the stated value, more typically +/−4% of the stated value, more typically +/−3% of the stated value, more typically, +/−2% of the stated value, even more typically +/−1% of the stated value, and even more typically +/−0.5% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

BRIEF DESCRIPTION OF DRAWINGS

The accompanying drawings illustrate a disclosed embodiment and serves to explain the principles of the disclosed embodiment. It is to be understood, however, that the drawings are designed for purposes of illustration only, and not as a definition of the limits of the invention.

EXAMPLES

Figures 1, 2:
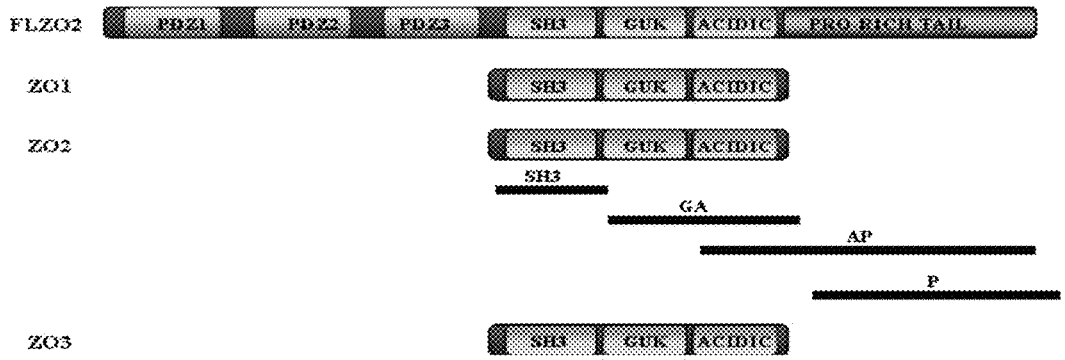
FIG. 1 shows the SH3-GUK-Acidic (SGA) domains of the bait used in Example 2, as well as of ZO-1, ZO-2 and ZO-3.
FIG. 2 shows the alignments of the zinc finger domains and the DNA base contact residues −1, 2, 3 and 6 for Slug and Zif268 in Example 8 (SEQ ID NOs:30-31).

Non-limiting examples of the invention and a comparative example will be further described in greater detail by reference to specific Examples, which should not be construed as in any way limiting the scope of the invention.

Example 1

ZO-1, 2 & 3 Constructs

The templates used to generate the various ZO-1, 2 and 3 domain constructions used in the following examples were from Reichert et al. These various domains of ZO-1, 2 and 3 namely: Human ZO-1 SGA (amino acids 491-883), Canine ZO-2SGA (amino acids 575-947), ZO-2SH3 (amino acids 575-713), ZO-2GA (amino acids 714-947) and Canine ZO-3 SGA (amino acids 451-898), were cloned into pGBKT7 (Clontech) with primers designed to introduce a 5' EcoRI and a 3' SalI restriction site.

For the cloning of the various domains of ZO-2 namely: Canine ZO-2SGA (amino acids 575-947), ZO-2GA (amino acids 714-947), ZO-2AP (amino acids 883-1174) and ZO-2P (amino acids 948-1174) into pGEX-6P-1 (Amersham Biosciences), primers were designed to introduce a 5' EcoRI and a 3' SalI restriction site.

For the cloning of the various point mutations of ZO-2 namely: Canine ZO-2SGA I726V, F852Y, N848S F852Y and N848S F852Y I726V in pGEX-6P-1 (Amersham Biosciences), suitable primers were designed based on manufacturer's instructions (Phusion® Site-Directed Mutagenesis Kit). Sequences of the primers used are available upon request.

For the cloning of the MYC tagged GA domain of ZO-1, ZO-2 and ZO-3 namely: Canine ZO-1GA (amino acids 631-883), ZO-2GA (amino acids 713-947), ZO-3GA (amino acids 606-899) into pGBKT7 for in vitro translation, primers were designed to introduce a 5' EcoRI and a 3' NotI restriction site. pcDNA3-Flag-ZO2 (amino acids 1-1175) was provided by Reichert et al and pcDNA3-Flag-ZO2ΔGA was obtained by deleting amino acids 713-947 using suitable overlapping primer pairs.

For the cloning of the nucleus targeting, membrane targeting and non-targeting truncated ZO-2 constructs namely: Canine ZO-2 3PSGA (amino acids 495-947) and ZO-2 3PSGAP (amino acids 495-1444) into pcDNA3 (Invitrogen), primers were designed to introduce a 5' EcoRI and a 3' XbaI restriction site. Nuclear and membrane targeting signals were introduced by PCR. The nucleus targeting signal was a three tandem repeat of the nuclear localization signal (NLS) of the simian virus 40 T-antigen. The sequence was obtained from the pDsRed2-Nuc vector (Clontech) (nucleotide position: 1298-1387), while the membrane targeting sequence was from the N-terminal amino acids of neuromodulin, also called GAP-43, it contained a signal for post-translational palmitoylation of cysteines 3 and 4 that targeted the fusion protein to the membranes. This sequence was obtained from the pEYFP-Mem vector (Clontech) (nucleotide position: 679-738). All constructs were verified by sequencing.

Slug Constructs

The full-length mouse Slug cDNA was obtained from the I.M.A.G.E Consortium cDNA clone 2225875 by using suitable primers covering the 5' and 3' coding region of the cDNA. The full length Slug cDNA, as well as the C'-terminus and N'-terminus truncation of Slug, to be named as EX (short for excluding the zinc finger domains) and ZNF (the 5 zinc finger domains of Slug) respectively, was cloned into pGEX4T-1 (Amersham Biosciences; 5'-BamHI/3'-SalI or EcoRI), pMAL (New England BioLabs; 5'-BamHI/3'-SalI), pEGFP, and pDHA (a modified pCI-neo vector (Promega) with two HA-Tags added to the 5' end of its MCS, 5'-EcoRI/3'-NotI) expression vectors. The GST-W199A construct was made by mutating trytophan at position 199 to an alanine using suitable primer pairs. Suitable overlapping primer pairs were used to generate substitutions in amino acids to disrupt the cysteine residues (C188A, C191A) involved in maintaining the zinc finger structures of zinc finger 3. Sequences of the primers used are available upon request.

Cell Lines and Transfection

The cell lines commonly used during the study were COS-1, 293T and MDCK. They were cultured in Dulbecco's Modified Essential Medium (DMEM-low glucose) with 10% FCS and supplemented with Penicillin/Streptomycin and L-Glutamine, at 37° C., 5% $CO_2$ and 95% humidity. MDCK cells were either seeded sparsely ($1\times10^5$ cells/per well) or densely ($4\times10^5$ cells/per well) on a 6 well plate with a coverslip in each well and grown overnight.

The plasmid DNA from midiprep was used for transfection of cells. A combination of lipofectamine plus and reagent or lipofectamine 2000 along with optimem I (Invitrogen) were used, following the manufacturer's protocol. Transfected cells were analyzed 24 or 48 hrs after transfection. For the generation of stable cell lines, cDNAs in mammalian expression vectors were transfected into MDCK cells using Lipofectamine 2000 (Invitrogen) and maintained for 24 hr prior to treatment with G418 (Calbiochem) and a selection period of 3-4 weeks until clones appear. Multiple clones were picked with cloning rings, combined and expanded until they reach a number suitable for further concentration by cell sorting. These combined positive clones were further screened with Western blot and immunofluorescence.

Antibodies

All antibodies used for Western blotting were diluted in 2% BSA in PBS 0.1% tween buffer with the indicated dilution factor. The following commercially available primary antibodies were used: rabbit anti-ZO-1 (Zymed Laboratories, South San Francisco, Calif., USA, Cat. #61-7300) 1:1000, rabbit anti-ZO-2 (Zymed Laboratories, South San Francisco, Calif., USA, Cat. #71-1400) 1:1000, rabbit anti-ZO-3 (Zymed Laboratories, South San Francisco, Calif., USA, Cat. #36-4000) 1:1000, rabbit anti-Slug Ctr antibody (Abgent, Cat. #AP2053a) 1:200, goat polyclonal anti-Slug antibody (Santa Cruz, Cat. #SC-10436) 1:200, rabbit anti-Slug C19G7 (Cell signaling, 9585S) 1:1000, mouse anti-laminB1 (Abcam, Cat. #3046-100) 1:3000, rabbit anti-alpha tubulin (Abcam, Cat. #ab15246-500) 1:3000, mouse anti-GAPDH (Chemicon, Cat. #MAB374) 1:20000, rat monoclonal anti-Hemagglutinin (HA) (Roche Diagnostics, Indianapolis, Ind., USA, Cat. #1867423) 1:1000, mouse anti-Flag (Sigma, Cat. #F3165) 2 μg/10 ml, mouse anti-Myc antibodies (Roche Diagnostics, Indianapolis, Ind., USA, Cat. #11667149001) 1:2000, rabbit anti-GST (Santa Cruz, Cat. #SC-459) 1:1000, mouse anti-MBP (abcam, Cat. #R29.6) 1:1000, rabbit anti-GFP (Biovision, Cat. #3999-100) 1:1000.

As for the secondary antibodies, the following commercially available secondary antibodies were used at 1:5000: bovine anti-goat horseradish peroxidase (HRP)-labeled secondary antibodies (Santa Cruz, Cat. #SC-2350), donkey anti-goat HRP (Santa Cruz, Cat. #SC-2020), goat anti-rat HRP (Santa Cruz, Cat. #SC-2006), goat anti-rabbit HRP (Bio-Rad, Cat. #170-6515) and goat anti-mouse HRP (Bio-Rad, Cat. #170-6516).

All antibodies used for immunofluorescence were diluted in 1% BSA PBS. The following commercially available primary antibodies were used: mouse anti-ZO-2 (Zymed Laboratories, South San Francisco, Calif., USA, Cat. #37-4700) 1:100, mouse anti-SC-35 (Sigma-Aldrich, Cat. #S4045) 1:300, rabbit anti-Slug Ctr antibody (Abgent, Cat. #AP2053a) 1:100, rabbit anti-Slug C19G7 (Cell signaling, 9585S) 1:100, rat monoclonal anti-Hemagglutinin (HA) (Roche Diagnostics, Indianapolis, Ind., USA, Cat. #1867423) 1:100, and mouse anti-Flag (Sigma-Aldrich, Cat. #F3165; 2 μg/10 ml).

Fluorescently labeled (Alexa 488 and 594) secondary antibodies were from Molecular Probes (Eugene, Oreg., USA) 1:1000, and 4-6-Diamidino-2-phenylindole (DAPI)

(Molecular Probes, Cat. #D1306) with a concentration of 300 nM in PBS was used to stain the nuclei of cultured cells.

Example 2

Yeast Two-hybrid System

A yeast two-hybrid screen was performed using the SH3-GUK-Acidic (SGA) domain of canine ZO-2 (amino acids 575-945) fused in-frame to the GAL4 DNA binding domain of the yeast expression vector pGBKT7 (Clontech) as a bait and a pre-transformed mouse 17 day embryo cDNA library fused to the GAL4 transactivator domain in the yeast expression vector pGADT7 (MATCHMAKER Two Hybrid System; Clontech). The SGA domains of the bait, as well as the SGA domains of ZO-1, ZO-2 and ZO-3 are shown in FIG. 1.

All experimental details were according to the manufacturer's protocols. Clones were screened at high stringency with a quadruple (-Trp, -Leu, -His, -Ade) dropout media and then tested for α- and β-galactosidase activity. Library plasmids with the cDNA inserts from positive clones were isolated and sequenced, resulting in the identification of the entire Slug cDNA. The interaction was retested by transforming this Slug cDNA plasmid with bait vectors carrying the human ZO-1 SGA domain (amino acids 490-883), the canine ZO-2 SGA (amino acids 575-945), SH3 (amino acids 575-713), as well as the GA domain (amino acids 714-945) or the canine ZO-3 SGC domain (amino acids 450-899). Empty pGBKT7 and a bait plasmid with laminin cDNA (Clontech) were used as negative controls.

The yeast two-hybrid screen resulted in the isolation of full-length Slug, which was further tested. by co-transformation with either pGBKT7 or pGBKT7-ZO-2SGA using QDO which lacked leucine, tryptophan, histidine and adenine as well as, α- and β-galactosidase assays. The presence of 'bait' and 'prey' plasmids in co-transformed cells was shown by growth on double drop-out (DDO) plates lacking leucine and tryptophan. pGADT7-Laminin C+pGBKT7-p53, pGBKT7+pGADT7, pGBKT7-ZO-2SGA+pGADT7, and pGBKT7+pGADT7-Slug, were all used as negative controls, while pGADT7-T-Ag+pGBKT7-p53 served as the positive control.

One particular clone named 30A was found to grow on quadruple dropout media (QDO) media and turned blue in both α-Gal Assay and β-Gal assays. This indicated the binding of the ZO-2-SGA bait to an unknown prey from the library leading to the activation of various promoters for survival in QDO media and expression of α-galactosidases and β-galactosidases that elicited the color change in X-gal media. The library plasmid of this positive clone 30A was isolated, sequenced and was found to harbor the entire Slug cDNA.

Accordingly, it was shown that Slug is a potential interacting partner of ZO-2SGA verified by QDO selection, α-gal assay and β-gal assay.

The interaction was retested by transforming this Slug cDNA plasmid with bait vectors carrying the human ZO-1SGA domain (amino acids 490-883), the canine ZO-2SGA (amino acids 575-945), SH3 (amino acids 575-713), GA domain (amino acids 714-945), as well as the canine ZO-3SGA domain (amino acids 450-899). Interactions were determined by monitoring the growth of the co-transformed yeasts in on selective media & β-galactosidase activity. It was observed that only yeast co-transformed with pGBKT7-ZO-2SGA and pGADT7-Slug or pGBKT7-ZO-2GA and pGADT7-Slug grew on QDO selective media and produced blue color colonies, an indication of β-galactosidase activity. Hence, Slug did discriminately interact with the SGA domain of ZO-2 and not with those of ZO-1 or ZO-3, thus showing the existence of non-redundant features within the ZO family members.

Empty pGEKT7 or a bait plasmid with laminin cDNA (Clontech) was used as negative controls. No interaction was detected between the Slug and laminin, nor was there any interaction of Slug with an empty library vector comprising of the Gal4 DNA binding domain alone. Hence auto-activation and non-specific activation were checked and found to be negative.

Example 3

In Vitro Binding Assay

Since the binding of ZO-2 was mapped to the GA domain, only this region would be used for this binding. An in vitro translation system was used to make the ZO-1, ZO-2 and ZO-3 GA domain separately so that their binding to Slug can be reconfirmed and verified individually in a system with minimum complexity.

GST, GST-Slug, GST-EX, GST-ZNF and various GST-tagged ZNF truncated Slug protein were produced, purified and bound to glutathione Sepharose-4B (Amersham Biosciences, Piscataway, N.J., USA) following standard protocols. Bound proteins were quantified by SDS-PAGE by comparing with known amounts of BSA as standards. A 15 cm dish of MDCK cells were grown to 80-90% confluence and lysed in cold buffer B (PBS with 1% TX-100 PBS, 1 mM EDTA, Complete EDTA free protease inhibitor cocktail (Roche Diagnostics, Indianapolis, Ind., USA), 1 mM dithiothreitol (DTT), 300 µg/ml Benzamidine, and put through a single freeze-thaw cycle. The lysate was centrifuged at 13000 rpm for 10 min at 4° C. to obtain a clear supernatant. 30 µl bed volume of glutathione Sepharose-4B carrying 20 µg of GST or GST fused Slug derived, full length or truncated proteins were incubated with 1.5 mg of the MDCK cell lysate, for 3 hrs at 4° C. The beads were washed with 500 µl of cold buffer B for 3 washes. This was followed by resuspension in 30 µl of SDS sample buffer and heating of the sample at 95° C. for 5 min. The analysis of the bound proteins were carried out by running 25 µl of the sample through a 10% SDS-PAGE gel followed by autoradiography using suitable antibodies.

It was found that MYC-ZO-2GA can be captured by GST-Slug and C-terminal portion GST-ZNF. Neither MYC-ZO-1GA nor MYC-ZO-3GA can be captured down by GST-Slug or GST-ZNF. Hence the findings confirmed the earlier observations that Slug binds mainly to ZO-2 but not ZO-1 or ZO-3.

Example 4

Immunoprecipitation

The interaction between ZO-2 and Slug in vivo was demonstrated by immunoprecipitating endogenous ZO-2 from the MDCK lysate.

pDHA-Slug and pcDNA-Flag-ZO2 or pcDNA-Flag-ZO2ΔGA were co-transfected into COS1 cells and then lysed after 24 hrs using lysis buffer (10 mM Tris HCl pH7.9, 150 mM NaCl, 0.02% sodium azide, 1% Trition X-100, 1% sodium deoxycholate, 1% BSA, protease inhibitor cocktail tablet). 2 mg of the lysates were then incubated with the 30 µl bed volume of the immobilized anti-HA resins for 3 hrs followed by 3 washes with lysis buffer. This was followed by resuspension in 30 µl of SDS sample buffer without any reducing agents and heating of the sample at 95° C. for 5 min. The analysis of the bound proteins were carried out by running all 25 µl of the sample through a 10% SDS-PAGE gel followed by detection with the appropriate antibodies.

MDCK cells (3×10⁶/150 mm petri dish) were lysed at 0° C. in 1 ml of lysis buffer (20 mM Tris HCl pH8.0, 137 mM NaCl, 10% glycerol, 1% Trition X-100, 0.5% Sodium deoxycholate, 15 U/ml DNase I, protease inhibitor cocktail tablet) and briefly sonicated. 2 mg of total protein were incubated with 10 µg of mouse anti-ZO2 or mouse. IgG control at 4° C. for 1 hr followed by another 2 hrs incubation with 80 µl of suspended (25% v/v) IP matrix (Santa Cruz, sc-45060). They were then washed with 1 ml PBS each time for 2 times, followed by a final wash with 1 ml PBS with 0.1% Tween. The precipitates were boiled in sample buffer for 5 min and subjected to electrophoresis and immunoblotting with the relevant antibodies.

As mentioned above, mouse preimmune serum was used as a negative control for immunoprecipitation. The samples were then electrophoresed, blotted and probed with anti-Slug and anti-ZO-2 antibodies. The result showed that Slug specifically interacted with ZO-2 and an absence of Slug in the negative control where pre-immune serum was used for immunoprecipitation.

Example 5

TNT In Vitro Translation Binding Assay

In an attempt to map the exact binding domain of ZO-2SGA for Slug, GST-ZO-2SGA, GST-ZO-2SH3, GST-ZO-2GA, GST-ZO-2AP (acidic and proline rich domain) and GST-ZO-2P (proline rich domain) were used for binding to HA-Slug, HA-EX (the N-terminus region of Slug excluding the zinc finger domain) and HA-ZNF (the C-terminus zinc finger domain).

In vitro translation was carried out using Quick Coupled T7 TNT System (Promega, Madson, Wis.) according to the manufacturers protocol. Slug, EX and ZNF cloned into the pDHA vector were in vitro translated and labeled with 35S Methionine. GST, GST-ZO-2 SGA, GST-ZO-2 SH3, GST-20-2 GA, GST-ZO-2 AP and GST-ZO-2 P were produced, purified as described above and were bound to glutathione Sepharose-4B (Amersham Biosciences, Piscataway, N.J., USA) following standard protocols.

Purified GST-fusion proteins were quantified by SDS-PAGE by comparing with known amounts of BSA as standards. 20 µl bed volume of beads carrying 20 µg of GST or the above GST fused ZO-2 truncated proteins were incubated with 10 µl of in vitro translated 35S Methionine labeled, HA tagged Slug, EX or ZNF and topped up with 200 µl of buffer B (PBS with 1% TX-100 PBS, 1 mM EDTA, Complete EDTA free protease inhibitor cocktail (Roche Diagnostics, Indianapolis, Ind.), 1 mM dithiothreitol (DTT), 300 µg/ml Benzamiidine) for 3 h at 4° C. The beads were washed three times with 500 µl of buffer B each time. This was followed by suspension in 30 µl of SDS sample buffer and the analysis of the bound proteins by running through a 15% SDS-PAGE gel and autoradiography, with a 2 to 3 day exposure period. To reciprocate the binding, GST, GST-Slug and GST-ZNF were used as baits. They were incubated with in vitro translated MYC-ZO-1GA, MYC-ZO-1GA or MYC-ZO-3GA and probed for the presence of the different MYC-ZOs GA domains using mouse anti-myc antibodies (Roche Diagnostics, Indianapolis, Ind., USA).

The results showed that the SH3 and the P do not bind to Slug or its ZNF domain. Instead it is the GA domain that exhibits the strongest binding effect comparable with signals obtained from binding of ZO-2SGA to GST-Slug and GST-ZNF. Binding of Slug and ZNF to GST-ZO-2AP can be detected but obviously weaker. GST-ZO-2P does not bind to Slug or ZNF.

Taken together, it goes to show that GUK is the more potent interacting domain, whilst the acidic domain only binds weakly to the ZNF domain of Slug.

Example 6

To verify the binding of full length ZO-2 to full length Slug in vivo, HA-Slug and Flag-ZO-2 or Flag-ZO-2ΔGA constructs were co-transfected into COS-1 cells.

This is followed by immunoprecipitating using the method in Example 4 with either anti-Flag and probing by anti-HA, or with anti-HA antibodies following which anti-Flag will be used for probing instead. Equal amounts of total protein were used to immunoprecipitate HA-Slug or Flag-ZO-2. Following SDS-PAGE, the co-precipitation of ZO-2 or Slug, respectively, was monitored by Western blot analysis using antibodies to the Flag or HA tags, respectively. When Flag-ZO-2 was immunoprecipitated, HA-Slug could be detected with anti-HA but not so when the GA truncated form of Flag-ZO-2 was used.

Taken together, it showed that HA-Slug could bind to Flag-ZO-2 but not to Flag-ZO-2ΔGA in an in vivo setting. When HA-Slug was immunoprecipitated instead, Flag-ZO-2 could be detected with anti-Flag but not for Flag-ZO-2ΔGA. Hence, it reconfirmed the binding of HA-Slug to Flag-ZO-2 but not to Flag-ZO-2ΔGA.

Example 7

The ZNF region of Slug is required for binding to ZO-2. However, there are 5 zinc finger domains (ZNF1-5) within the ZNF region of Slug. Hence, in order to narrow down the exact zinc finger domain(s) responsible for initiating the interaction with ZO-2, a GST binding assay was carried out in accordance with the procedure in Example 3 using various zinc finger truncated mutants of Slug.

The series of GST-Slug derived truncated protein ranging from 0 to 28 were incubated with MDCK cell lysate and probed for the presence of endogenous ZO-2 using specific antibodies against ZO-2, where L is 15% loading input.

It was observed that ZNF3 was critical and sufficient for binding to ZO-2 since all constructs that harbored ZNF3 can capture ZO-2. Even that of construct 15 that comprised of merely the N-terminus EX domain and ZNF3 is sufficient to capture down ZO-2.

Example 8

Fine Mapping of the Interaction Domain in ZO-2 and Slug

Mapping of the crucial amino acids involved in binding to ZO-2 GUK was aided by molecular dynamics simulations using the known crystal structures of closely related proteins such as the zinc finger protein Zif268 and the GUK containing PSD95 as templates for the zinc finger 3 of SNAI2 and the GUK of ZO-2.

To elaborate on this process, well-studied crystallized structure of PSD-95 (PDB file 1KJW) was used for modeling the docking site for Slug on ZO-2. Although there are several domains in PSD-95, only the well-conserved GUK domain (A534 to V563, and V613 to L724) was used in this case for modeling ZO-2 GUK. The classification of the various domains of PSD-95 is as follows: SH3 Domain (G430 to K503), HOOK Domain (W507 to Y533), GUK domain (A534 to V563, V613 to L724) and NMP Domain (part of GUK domain) (P564 to S612).

In the case of Slug, the $C_2H_2$ zinc finger Zif268 in complex with DNA from PDB 1A1H, was used as template for Slug ZNF3, 4 and 5 in modeling its binding to ZO-2 GUK. This was due to availability of its crystal structure and its exhibition of good homology with Slug. In the alignment, the Zif268 (1A1H) consists of 3 $C_2H_2$ zinc fingers. Full length Slug consists of 4 $C_2H_2$ zinc fingers while zinc finger 5 is a $C_2HC$ zinc finger. The alignments of their zinc finger domains and the DNA base contact residues −1, 2, 3 and 6 (these numbers denote the positions from the start of each alpha helix) are shown in FIG. 2.

Figure 3:
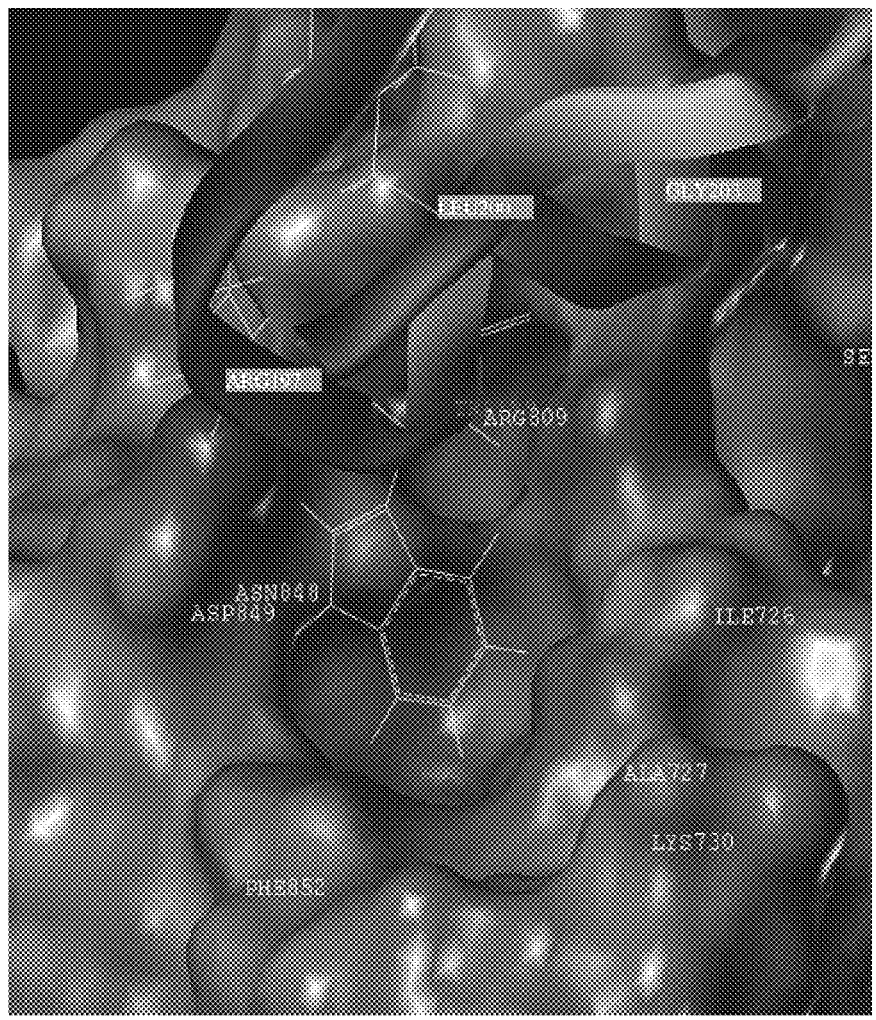
FIG. 3 shows the hydrophobic pocket within the GUK domain formed by the region between helix 8 (N848 D849 F852) and helix 2 (I726 A727) of ZO-2, where the ring side chain of W199 is shown buried inside the hydrophobic pocket of ZO-2 GUK formed mainly by residues N848, D849, F852, I726 and A727.

With the PSD-95 GUK serving as a template for ZO-2 GUK and the Zif268 ZNFs as the template for Slug ZNF3, 4, 5, the model reveals a hydrophobic pocket within the GUK domain formed by the region between helix 8 (N848 D849 F852) and helix 2 (I726 A727) of ZO-2 as shown in FIG. 3. In FIG. 3, the ring side chain of W199 is shown buried inside the hydrophobic pocket of ZO-2 GUK formed mainly by residues N848, D849, F852, I726 and A727.

There are reasons to suspect that the tryptophan (W) amino acid in position 199 of Slug ZNF3 can fit very well into this hydrophobic pocket of ZO-2, based on the assumption that when two proteins interact, there will be a pocket or complementary surface to make the interaction stronger. W199 is a good target as there are evolutionary evidences that support a ring structure amino acid like tryptophan wedging into such a pocket in GUK domain.

In order to verify if the tryptophan residue at position 199 plays a role here in the binding of Slug to ZO-2, a W199A point mutation was made prior to doing the GST-binding assay in accordance with the procedure in Example 3. In addition two cystenine to alanine point mutations were made on cystenine 188 and 191 (C188A and C191A) to check if the zinc finger structure plays a role in the binding of Slug to ZO-2.

As it turned out, W199 is critical for binding but not C188 and C191 that help maintain the zinc finger structure of Slug ZNF3.

Further support of the model comes from binding assays carried out using the following ZO-2 point mutants that affect the crucial amino acids surrounding the hydrophobic pocket within the GUK domain of ZO-2, namely GST-ZO2 SGA I726V, F852Y, N848S+F852Y and N848S+F852Y+I726V. The rationale behind the selection of these mutations is that since ZO-1 and ZO-3 do not bind Slug, unlike ZO-2, and that they differ in the above amino acids that projects into the hydrophobic pocket, mutating these amino acids in ZO-2 to those corresponding to either ZO-1 and/or ZO-3 should abolish the binding of Slug to these ZO-2 mutants. The point mutated GST-ZO2 proteins were incubated with GFP-Slug MDCK lysate and probed for the presence of both GFP-Slug and endogenous Slug using specific antibodies against Slug.

As expected, the single point ZO-2 mutants showed weakened binding to GST-Slug, while a combination of 2 or all 3 mutations virtually abolished the interaction with GST-Slug. No interaction was detected with the GFP negative control while strong interaction was readily seen with GST-ZO2 SGA WT positive control.

Interestingly, mutating the corresponding amino acids in ZO-1 to those of ZO-2 did not render an effective binding of this ZO-1 mutant to Slug. Hence it hints of amino acids within ZO-1 that may yet interfere with such an interaction.

Example 9

Localization of ZO2 & Slug in MDCK Culture

To determine if ZO-2 found in the nucleus of sparse MDCK cells is associated with Slug, MDCK cells were grown in both sparse and dense conditions as follows.

Further, a linear wound to the cell monolayer was inflicted in one of the dense cultures to visualize their localization in the region proximal to the wound in comparison to those at a distal area.

Proximity Ligation Assay (PLA)

This technology is based on two unique probes provided with the DUOLINK® kit (a kit that allows the detection, quantification and determination of cell localization of protein interactions and their modifications in a single experiment; the kit is based on in situ proximity ligation assay (PLA), which enables the analysis to be carried out while the cells are undergoing endogenous protein expression) that consist of a secondary antibody attached to a unique synthetic oligonucleotide serving as a reporter. The proximity of the probes allows for DNA hybridization and ligation at the exact site where these probes are in close proximity. The distance at which this can happen is merely 40nm or less. Hence only proteins that interact can hybridize, ligate, get amplified for detection by hybridizing to fluorescent probes. This method gives the specificity and sensitivity needed via DNA-DNA hybridization and DNA fold amplification of the initial ligation event respectively.

Since the limitation of this technique depends on the quality of the primary antibodies used for recognizing the interacting proteins, the quality and reliability of the antibodies were assessed by using the GFP-Slug MDCK as a positive control and GFP-W199A MDCK as a negative control.

MDCK cells ($4 \times 10^4$-$1 \times 10^5$ cells/per chamber) were grown on chamber slides (Lab-Tek 8 well glass slide system 177402) for at least 16 h, washed twice with PBS, and fixed in 3.7% formaldehyde in PBS for 30 min at room temperature. Subsequently, the slides were washed with PBS; incubated for 10 min in 50 mM NH4Cl, PBS; washed with PBS; permeabilized for 5 min in 0.2% Triton X-100 in PBS; and washed three times with PBS with 0.05% Tween 20. The slides were then blocked for 30 min with 2% BSA in PBS at room temperature.

After blocking, the appropriate combinations of antibodies in blocking buffer were added in a humidified chamber at 37° C. and incubated for 1 hr. After washing with DUOLINK® II wash buffer A (a kit that allows the detection, quantification and determination of cell localization of protein interactions and their modifications in a single experiment; the kit is based on in situ proximity ligation assay (PLA), which enables the analysis to be carried out while the cells are undergoing endogenous protein expression), proximity ligation was performed using the Rabbit MINUS and Mouse PLUS DUOLINK® (a kit that allows the detection, quantification and determination of cell localization of protein interactions and their modifications in a single experiment; the kit is based on in situ proximity ligation assay (PLA), which enables the analysis to be carried out while the cells are undergoing endogenous protein expression) in situ PLA kits (OLINK Bioscience) according to the manufacturer's protocol. Subsequently, slides were stained with DAPI before embedding in Crystal/Mount™(Biomeda). Fluorescence was detected using a Zeiss Axioplan microscope equipped with the Zeiss Axio-Vision Imaging System or Zeiss LSM 700 laser scanning microscope.

Antibodies used for PLA were Zymed mouse anti-ZO2 and cell signaling rabbit anti-Slug. Single antibody incubations were performed as negative controls. These negative controls did not give significant PLA signals.

The images (not shown) were acquired with a 40× objective, a 1.6× magnifier and a 10× eye-piece to obtain images that gave a wide range of cell number per captured field. The Spots per cell were counted by semiautomated image analysis using the single cell analysis function of BlobFinder software.

It was shown that the number of nuclear PLA spots pick up is much higher in the case of GFP-Slug MDCK than those seen in GFP-W199A MDCK.

Further, ZO-2 and Slug were seen clearly inside the nucleus where the cells were seeded sparsely. While the border staining of ZO-2 was also clearly visible in these cells, the border staining of Slug was only weakly visible. Accordingly, ZO2 and Slug co-localize to the nucleus in sparse MDCK cells. The nuclear stains of ZO2 and Slug decrease and disappear as the monolayer becomes confluence and subsequently adopt a more cytoplasmic localization.

In contrast, when the MDCK cells were seeded densely, the nuclear staining of Slug became perinuclear while border staining diminished further. Similarly, the staining of nuclear ZO-2 also turned perinuclear but a taint of it was still observable within the nucleus. The border staining of ZO-2 was still detectable.

To rule out the absence of signals due to substrate limitation at high cell number, the detection of ZO-1-ZO-2 complexes was included as a positive control. Strong PLA signals of ZO-1-ZO-2 complexes were shown to line the cell borders even at high cell densities, thereby ruling out substrate limitation as the reason for an absence of PLA signals for ZO-2-Slug complexes at high cell densities.

Accordingly, it was demonstrated that the PLA signals tended to decrease as the cell density increased.

The ZO-2-Slug PLA signals in MDCK cells of various densities were quantitated by counting the spots on the images taken with the BlobFinder software. The number of cells subjected to analysis per cell number group, ranged from around 200 to 350. The parameters were set so that only the cells that fell within the 25th to the 75th percentile of the cytoplasmic and nuclear area were automatically counted and scored. This would filter out cells that were not fully captured at the edge of the images as well as those that were abnormally large or small.

Figures 4, 5:
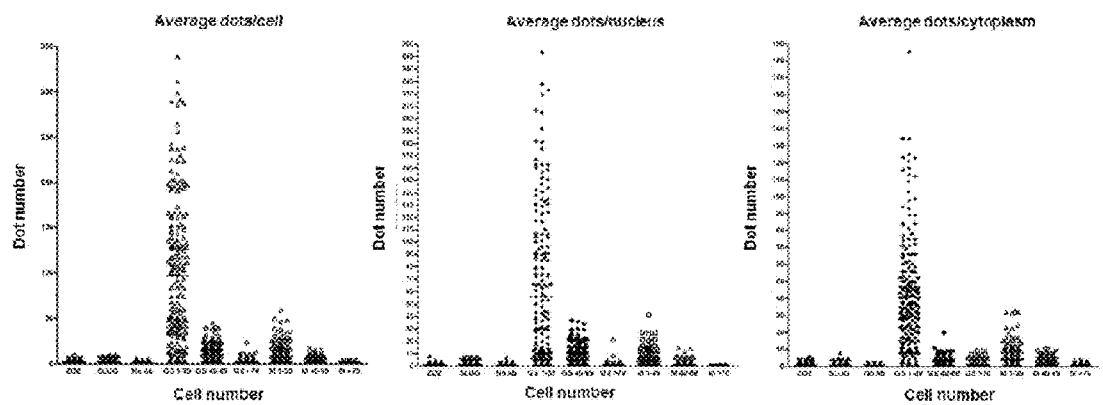
FIG. 4 shows the number of dots in the cell, nucleus and cytoplasm, respectively, in GFP-Slug MDCK cells seeded at a low cell density in Example 9. It can be seen that the count fell greatly when the cell number increased to 40-69 cells per image field and decreased down to a low background level once the cell number exceeded 70 cells per image field.
FIG. 5 shows the statistical analysis of the nuclear ZO-2 fragment and nuclear GFP-Slug staining in Example 11, evidencing that there is a positive relationship between the enhanced staining of GFP-Slug in the nucleus and the entry of Nu Flag ZO-2 3PSGAP into the nucleus. Null hypothesis is GFP-Slug enhanced staining in the nucleus is independent of Nu Flag ZO-2 3PSGAP entry into the nucleus.

The results shown in FIG. 4 indicate a high score of PLA signals in GFP-Slug MDCK cells seeded at a low cell density of 1-39 cells per image field. The PLA signals, were counted with BlobFinder software and the number of spots per cell, per nucleus and per cytoplasm were presented in the graph of FIG. 4. The data points were grouped by the cell number per field captured using a Zeiss Axioplan microscope with a 40× objective, a 1.6× magnifier and a 10× eye-piece. The use of primary antibodies against ZO-2 alone, Slug alone or the omission of the primary antibodies was used as controls.

As can be seen in FIG. 4, the PLA signal count fell greatly when the cell number increased to 40-69 cells per image field and decreased down to a low background level once the cell number exceeded 70 cells per image field. This pattern was mirrored in the case of MDCK cells, although the initial count in the sparsely seeded cell group was much lower than the GFP-Slug MDCK.

Wound Assay

MDCK cells were seeded onto 10 cm petri dish or coverslips in 24 wells-plate and grown until completely confluent. The cells were either left unwounded or wounded. Cells on the 10 cm plates were wounded by scrapping the monolayer with cress-crossing lines while those on coverslips were inflicted with a single scratch wound. In both instances a 1 ml pipette tip was used.

They were incubated overnight before being treated for immunofluorescence microscopy (as described in Example 10 below) or lysed with RIPA buffer (50 mM Tris HCl pH7.9, 150 Mm NaCl, 1 mM EDTA, 1% Trition X-100, 0.1% SDS, protease inhibitor cocktail tablet) for Western blot analysis.

In the cells proximal to the wound edge, both ZO-2 and Slug were clearly seen within the nucleus. However in cells that were a couple of layers distal from the wound edge, a reduced level of both nuclear ZO-2 and Slug was seen, evidenced by weakened nuclear stains of ZO-2 and Slug in cells distal from the wound.

To further demonstrate this temporal relationship of Slug and ZO-2 in cells that were wounded, two confluent plates of MDCK cells were grown with one subjected to numerous scratches while the other unscratched.

Nuclear and cytosolic fractions were prepared in equal amounts of proteins (40 µg) for each fraction analyzed by SDS-PAGE and Western blotting using an antibody to Slug. Lamin B1 and α-tubulin were used as markers and loading controls for the nuclear and cytosolic fraction, respectively.

It was shown that wounding of the monolayer caused an increase in the level of ZO-2 in the nuclear fraction while the amount in the cytosol remained comparable. A corresponding increase in nuclear Slug level was also discernable with wounding but not so in the cytosolic fraction.

Example 10

Immunofluorescence Microscopy

MDCK cells grown on coverslips or in chamber slides were washed three times with phosphate-buffered saline (PBS) followed by fixing for 30 min in 4% paraformaldehyde (PFA) pH7.4 on ice. Fixation step was stopped by quenching with 50 mM NH$_4$Cl-PBS for 10 min. This was followed by permeabilization with 0.2% Trition X-100 PBS for 5 min followed by 3 subsequent washes with PBS within 5 min. They were then blocked for 30 min in 1% BSA in PBS at room temperature. Following which, the fixed cells were incubated with the relevant antibodies at room temperature for 1 hr. After 3 washes, the cells were incubated with the Alexa FluorR secondary antibodies (1:1000) in blocking buffer for 1 hr at room temperature. After a final three washes with PBS, the coverslips were mounted with Crystal/Mount (Biomeda). The images were captured using a Zeiss Axioplan microscope equipped with the Zeiss Axio-Vision Imaging System.

Example 11

Presence of ZO-2 in the Nucleus Stabilizes Slug

As described, Slug and ZO-2 can interact. This association occurs between the ZNF domains of Slug and a C-terminal region comprising amino acids 495-1444 of ZO-2, and is abolished by substituting Trp199 in Slug to Ala (W199A). Since ZO-2 can localize either to the plasma membrane or the nucleus, the N-terminus of ZO-2 were coupled to known membrane or nuclear targeting signals to test if these constructs could influence the subcellular localization of Slug.

The ZO-2 constructs targeted to membranes were co-transfected with different Slug mutant into MDCK cells (results not shown). All Slug constructs harboring zinc finger domain 3, which carries W199 important for binding to ZO-2, accumulated together with the ZO-2 fragment in uncharacterized membranous structures in the cytoplasm. This co-localization with the ZO-2 fragment was abolished for constructs that either lack zinc finger 3 or carry the W199A mutation.

A ZO-2 truncation mutant containing the GUK domain important for the interaction with Slug was generated and fused to a nuclear localization signal (Nu-ZO2 3PSGAP). In contrast to wt ZO-2, which displays different subcellular localizations depending on experimental conditions, this nuclear targeting truncated ZO-2 is expected to simulate the enhanced nuclear accumulation of ZO-2 observed in sparse cultures and during wound healing. Cells stably expressing GFP, GFP-Slug or GFP-Slug W199A were transfected with this vector containing Nu-ZO2 SPSGAP.

It was shown that expression of Nu-ZO-2 3PSGAP resulted in an increase in the nuclear staining of GFP-Slug when visualized by immunofluorescence imaging in accordance with the procedure in Example 10. This reflected the enhanced retention of Slug in the nucleus through its binding to the ZO-2 construct. Consistent with this interpretation, a stronger nuclear GFP-Slug staining was not observed in cells that did not express the nuclear ZO-2 fragment or in cells expressing GFP-Slug W199A.

Statistical significance of the correlation between expression of nuclear ZO-2 fragment and enhanced nuclear GFP-Slug staining was confirmed by examining the images of cells taken following their fixation. While the images are not shown, the statistical analysis is shown in FIG. 5. FIG. 5 shows a positive relationship between the enhanced staining of GFP-Slug in the nucleus and the entry of Nu Flag ZO-2 3PSGAP into the nucleus. Null hypothesis is GFP-Slug enhanced staining in the nucleus is independent of Nu Flag ZO-2 3PSGAP entry into the nucleus.

$$X^2=(ad-bc)^2(a+b+c+d)/(a+b)(c+d)(b+d)(a+c)$$

Chi square statistical=125.4376
Degree of freedom=(no. of row−1) (no. of column−1)=1
Chi square critical=3.84 (with alpha of 0.05)

It is thus shown that Chi square statistical is much higher than Chi square critical. The data presents a statistically significant relationship between the variables in the table, hence null hypothesis is rejected.

An alternative hypothesis is that GFP-Slug enhanced staining in the nucleus is dependent on Nu Flag ZO-2 3PSGAP which binds to and retains GFP-Slug in the nucleus hence protecting it from proteasomal degradation.

There was a correlation between the nuclear expression of Nu-ZO2 3PSGAP and an enhanced nuclear GFP signal intensity for cells expressing GFP-Slug as seen in FIG. 5. These data suggest that binding of GFP-Slug to Nu-ZO2 SPSGAP results in its nuclear retention and hence protection from proteasomal degradation.

Cells stably expressing GFP-Slug, GFP Slug W199A or GFP were transfected or not with a vector carrying Flag tagged Nu-ZO-2 3PSGAP. Cells were then lysed and cytosol and nuclear fractions analyzed by Western blot using antibodies to GFP.

Figure 6:
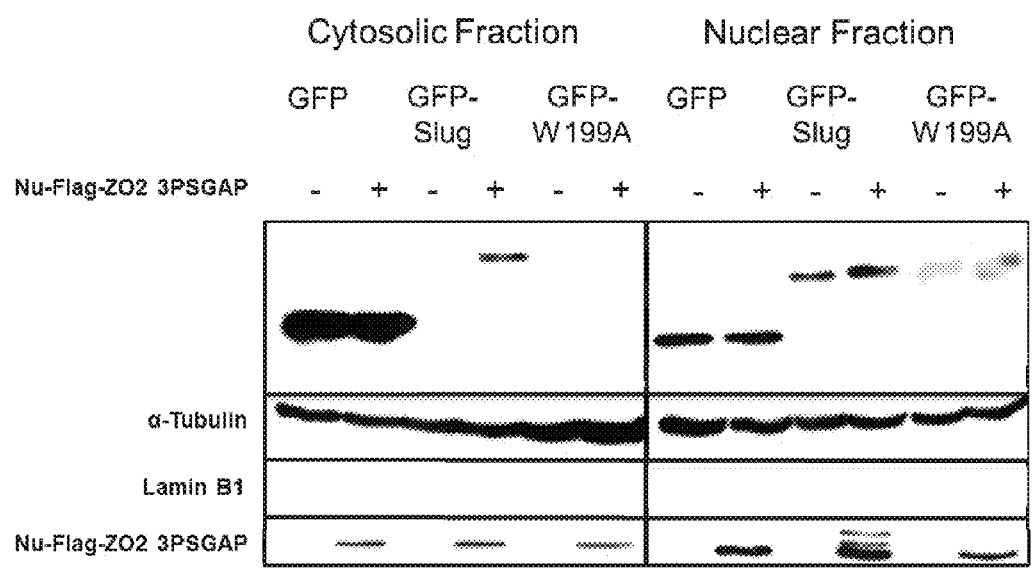
FIG. 6 shows the immunoblot referred to in Example 11, evidencing that expression of Nu Flag-ZO2 3PSGAP caused a dramatic increase in the nuclear and cytosolic protein levels for GFP-Slug, while no effect was observed on the levels of GFP-Slug W199A or the GFP control. Equal loading was monitored by probing for a-tubulin or lamin. B1 in the cytosolic or nuclear fractions, respectively. Anti-Flag antibodies were used to detect the presence of the transfected Nu Flag-ZO2 3PSGAP.

As shown in FIG. 6, expression of Nu Flag-ZO2 3PSGAP caused a dramatic increase in the nuclear and cytosolic protein levels for GFP-Slug. In contrast, no effect was observed on the levels of GFP-Slug W199A or, as a control, GFP. Equal loading was monitored by probing for α-tubulin or lamin B1 in the cytosolic or nuclear fractions, respectively. Anti-Flag antibodies were used to detect the presence of the transfected Nu Flag-ZO2 3PSGAP.

Figure 7:
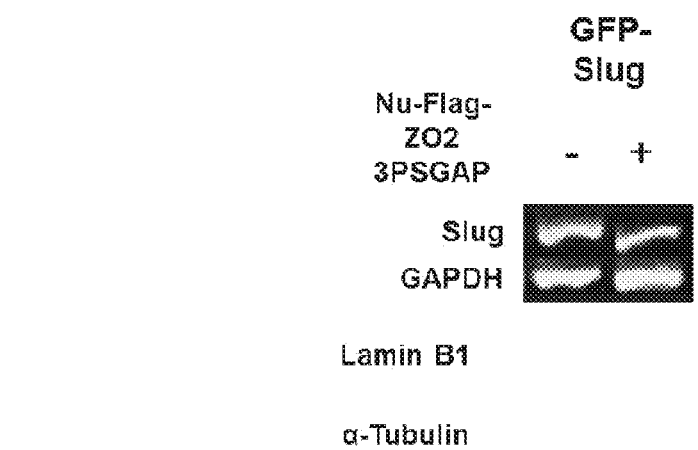
FIG. 7 shows a RT-PCR analysis referred to in Example 11, evidencing that Nu-ZO-2 3PSGAP expression did not affect GFP-Slug mRNA levels, thereby ruling out an effect on transcription.

The RT-PCR analysis is shown in FIG. 7. Total RNA extracted from Nu Flag-ZO2 3PSGAP transfected and non-transfected MDCK cells stably expressing GFP-Slug was amplified using specific primers for Slug and, as a control, GAPDH. Nu-ZO-2 3PSGAP expression did not affect GFP-Slug mRNA levels as assessed by RT-PCR shown in FIG. 7, ruling out an effect on transcription.

Taken together, these data are consistent with a stabilizing effect of Nu-ZO-2 3PSGAP on Slug.

Example 12

The stabilizing effect of Nu Flag ZO-2 3PSGAP on GFP-Slug has been demonstrated. It will therefore be interesting to examine whether the knock down of endogenous ZO-2 will have a destabilizing effect on GFP-Slug and/or endogenous Slug. Hence, the effectiveness of the siRNA against ZO-2 was tested here.

siRNA Knock Down $1 \times 10^5$ GFP-Slug MDCK cells were seeded in each of the wells in a 6 well plate and siRNA duplexes (60 pmol) were forward transfected and incubated for 48 h. siRNAs were synthesized by Invitrogen: (1) si-control (SEQ ID NOs: 20 and 21); (2) si-ZO-2 #2 (si GUK) (SEQ ID NOs: 22 and 23); and (3) si-ZO-2 #3 (si PDZ2) (SEQ ID NOs: 24 and 25).

A portion of the GFP-Slug MDCK cells were treated with MG132 (1:20000) for 16 h after the 48 h incubation. This was followed by a change to complete culture medium with cycloheximide (1:1000) and sampling at time zero and thereafter every 2 h. For ZO-2 rescue, $1.2 \times 10^6$ MDCK cells were seeded on 10 cm petri dishes and transfected with either si-ZO-2 #3 or si-control (370 pmol), along with either pcDNA3, pcDNA3-Nu Flag ZO-2 3PSGAP or pcDNA3-Nu Flag ZO-2 3PSGA constructs at 24 μg per plate. The cells were harvested after 48 h with RIPA buffer (50 mM Tris HCl pH7.9, 150 Mm NaCl, 1 mM EDTA, 1% Triton X-100, 0.1% SDS, protease inhibitor cocktail tablet) and analyzed by immunoblot.

Figure 8:
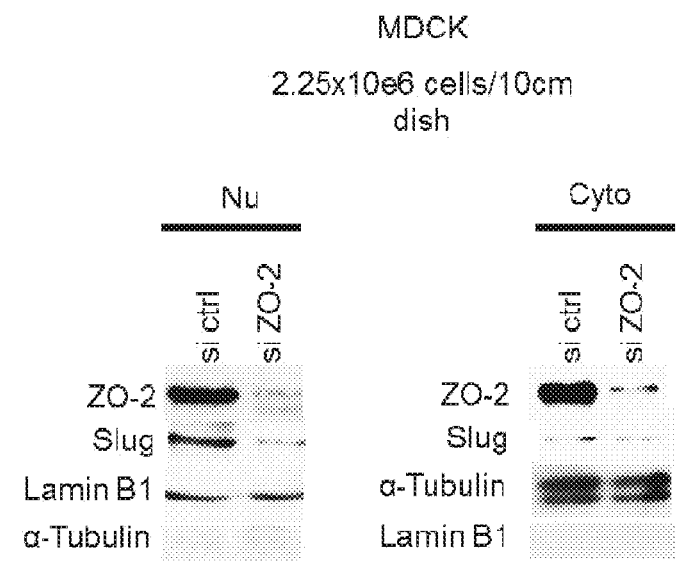
FIG. 8 shows the immunoblot referred to in Example 12, evidencing that knocking down ZO-2 caused an effective reduction of endogenous ZO-2 level both in MDCK cells and MDCK GFP-Slug. There was also a corresponding decrease in endogenous Slug and GFP-Slug level in the two respective experiments showing that a decrease in ZO-2 level did destabilize Slug and GFP-Slug in the two systems.

The immunoblot results shown in FIG. 8 evidence that knocking down ZO-2 caused an effective reduction of endogenous ZO-2 level both in MDCK cells and MDCK GFP-Slug. There was also a corresponding decrease in endogenous Slug and GFP-Slug level in the two respective experiments showing that a decrease in ZO-2 level did destabilize Slug and GFP-Slug in the two systems.

Once verified for its effectiveness of the siRNA against ZO-2, GFP-Slug MDCK cells was subjected to the same ZO-2 siRNA or a non-targeting siRNA control and tracked the degradation of both endogenous Slug and GFP-Slug in a time course assay lasting for 6 h and 2 h sampling intervals.

Analysis of cell lysate by immunoblotting following transfection of ZO-2 siRNA or a non-targeting control siRNA into GFP-Slug MDCK cells grown on 6 well plates. A portion of these cells were treated with MG132 (1:20000) after 48 h for a further 16 h. Degradation of GFP-Slug and Slug were tracked every 2 h for a total of 6 h, following a change to complete culture medium with cycloheximide. Cycloheximide was added to block further protein synthesis.

To demonstrate the absence of any off-targeting effect of ZO-2 siRNA on Slug or GFP-Slug, a parallel set of the same experiment was carried out but was subjected to the proteasome inhibitor MG132 treatment prior to a change of medium that contained cycloheximide.

Figure 9A:
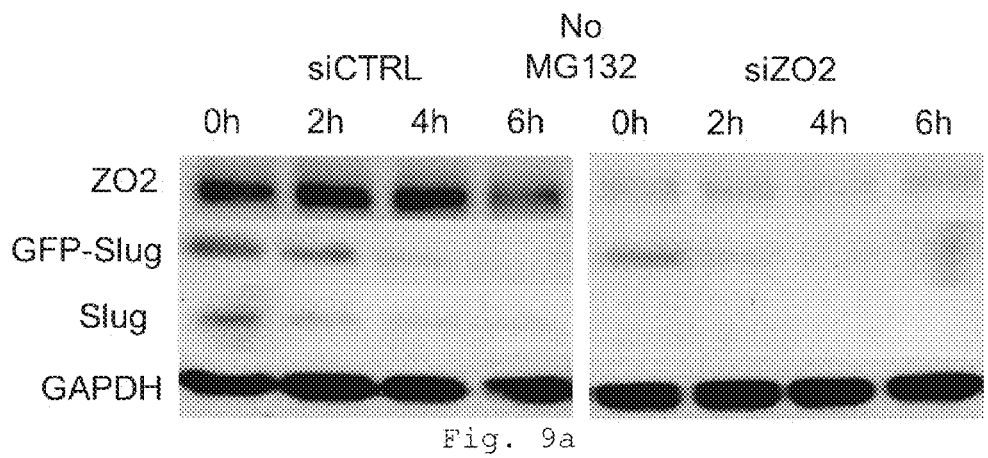
FIGS. 9a and 9b show that there was a more rapid turnover of both endogenous Slug and GFP-Slug when siRNA against ZO-2 was introduced in Example 12. The prior treatment with proteasome inhibitor MG132 delayed the turnover of both endogenous Slug and GFP-Slug by increasing their initial amount at time zero, thus evidencing the absence of off-targeting effect by showing the continued translation of Slug and GFP-Slug in the presence of ZO-2 siRNA. The stabilizing effect ZO-2 had on Slug and GFP-Slug was reaffirmed.
Figure 9B:
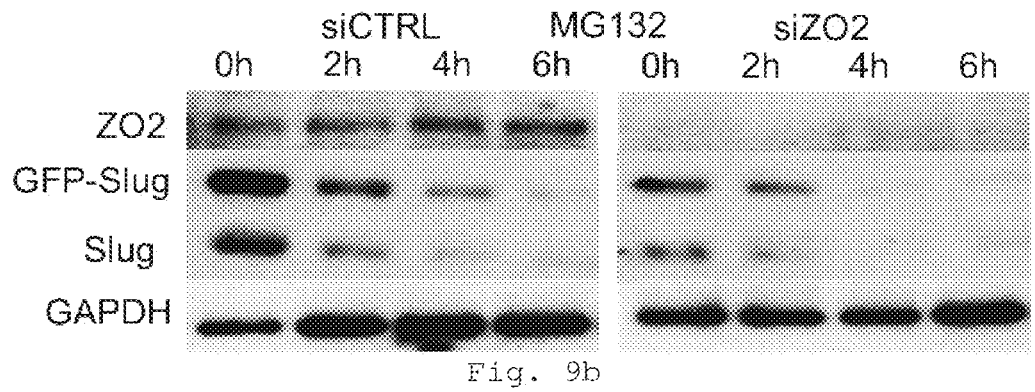

The results shown in FIGS. 9a and 9b revealed a more rapid turnover of both endogenous Slug and GFP-Slug when siRNA against ZO-2 was introduced. As shown in FIGS. 9a and 9b, this prior treatment with MG132 delayed the turned over of both endogenous Slug and GFP-Slug by increasing their initial amount at time zero.

Thus it demonstrated the absence of off-targeting effect by showing the continued translation of Slug and GFP-Slug in the presence of ZO-2 siRNA and reaffirmed the stabilizing effect ZO-2 had on Slug and GFP-Slug.

Figure 10:
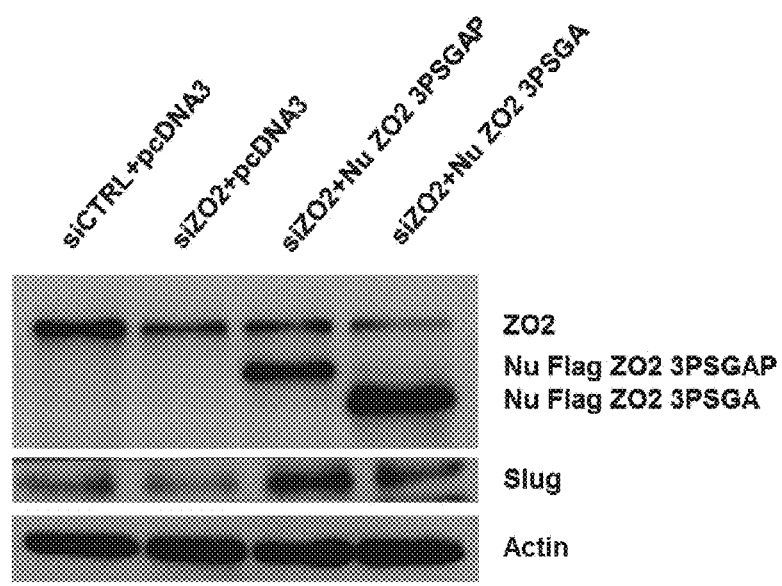
FIG. 10 shows the immunoblot referred to in Example 12, evidencing that constructs of si-ZO-2 MDCK transfected with either pcDNA3 Nu Flag ZO-2 3PSGAP or Nu Flag ZO-2 3PSGA retained the GUK domain to which Slug interacts.

When ZO-2 siRNA transfected MDCK was simultaneously transfected with either pcDNA3 Nu Flag ZO-2 3PSGAP or Nu Flag ZO-2 3PSGA, it was shown that the rescue was effective in increasing the amount of Slug. Both of these constructs retained the GUK domain to which Slug interacts. Analysis of cell lysate by immunoblotting following the transfection of ZO-2 siRNA or a non-targeting control siRNA along with pcDNA3, pcDNA Nu Flag ZO-2 3PSGAP or pcDNA Nu Flag ZO-2 3PSGA into MDCK cells grown on 10 cm plates is shown in FIG. 10. The levels of endogenous Slug in each case were analyzed by immunoblot after 48 h of incubation.

Knock Down of ZO-2 Stimulates the Proliferation Rate of MDCK GFP-Slug Cells

The effect of knocking down ZO-2 on the proliferation rate of MDCK GFP-Slug cells was assessed here.

MDCK cells were transfected with siRNA specific against ZO-2 or a non-targeting control siRNA. The transfected were grown for 3 days before they were processed for Western analysis and immunofluorescence microscopy. GFP and GFP-W199A were used as controls for the knock down experiment.

Cell lines stably expressing GFP, GFP-Slug and GFP-W199A were subjected to siRNA against ZO-2 or a non-targeting siRNA as a control. Their rate of proliferation was then assessed via the WST-1 based assay. The results are shown in FIG. 11.

Figure 11:
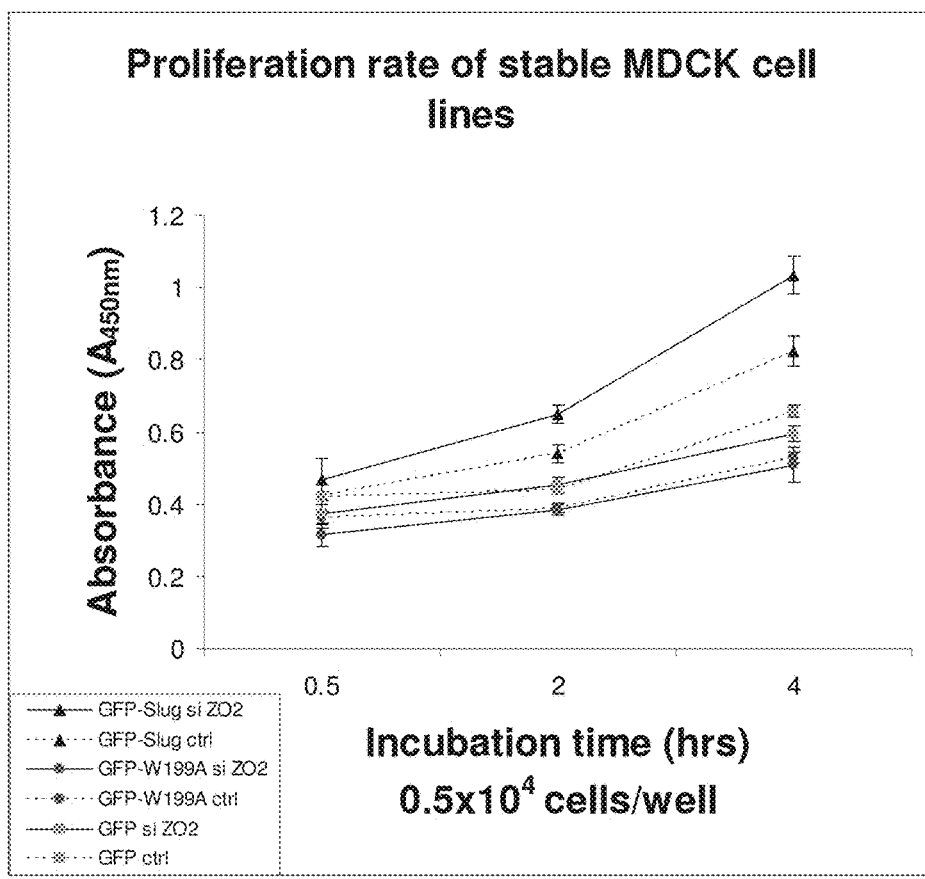
FIG. 11 shows that knocking down of ZO-2 led to a further increase in the proliferation rate for the GFP-Slug expressing cells demonstrated in Example 12. In contrast, proliferation of the GFP and GFP-W199A expressing cells was not significantly affected and remained below that of the GFP-Slug expressing cells treated with the control siRNA.

As shown in FIG. 11, knocking down of ZO-2 led to a further increase in the proliferation rate for the GFP-Slug expressing cells. In contrast, proliferation of the GFP and GFP-W199A expressing cells was not significantly affected and remained below that of the GFP-Slug expressing cells treated with the control siRNA.

Example 13

A rescue was also carried out using a full length mCherry tagged ZO-2 from mouse in this example. This construct is resistant to knock down by si-ZO-2 #3 which was designed specifically against canine ZO-2. Knock down of Slug was also carried out to confirm the target influenced by the knock down and replacement of ZO-2 was indeed Slug and GFP-Slug.

GFP-Slug MDCK cells were seeded at $1.5 \times 10^5$ cells in each well of a 6 well plate. siRNAs including si-control and si-ZO-2 #3 (30 pmol) were transfected following 3 h of incubation. This was followed by transfecting mCherry Mm Tjp2 constructs (4 μg) and a further 3 h incubation before a final change to complete media.

Figure 12:
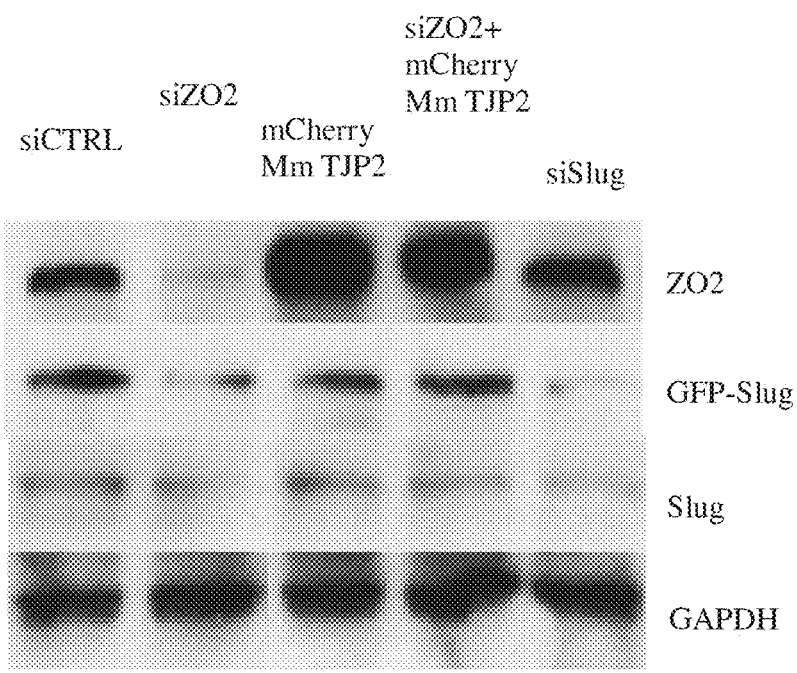
FIG. 12 shows the immunoblot referred to in Example 13, evidencing that the construct of mCherry tagged ZO-2 from mouse is resistant to knock down by si-ZO-2 #3 which was designed specifically against canine ZO-2.

Analysis of the cell lysate by immunoblotting followed the transfection of ZO-2 siRNA or a non-targeting control siRNA into GFP-Slug MDCK cells grown on 6 well plates. The levels of GFP-Slug and endogenous Slug in each case were analysed by immunoblot after 24 h of incubation and the results are shown in FIG. 12.

Example 14

In this example, presence of nuclear ZO2 and Slug was demonstrated in some clinical samples derived from the multiple cancer tissue array.

A multiple tissue array (Cybrdi™ Human Derived Biological Products CC00-10-001) slide was baked at 56° C. for 10 min, followed by treatment with xylene for 15 min. This was followed by rehydration using 95%, 90% and 70% ethanol for 2, 2 and 3 min respectively and finally distilled water for 2 times 5 min. The slide was then subjected to antigen retrieve using a 2100 retriever (ProteoGenix) in sodium citrate pH 6.0 for 12 min. After cooling, the slide was rinsed with PBS and subjected to PFA fixation (see immunofluorescence at Example 10 for details). The primary antibodies used were rabbit anti-Slug (Cell Signalling, 1:50) and mouse anti-ZO2 (Invitrogen, 1:50). The secondary antibodies used were Alexa FluorR 594 donkey anti-mouse IgG (1:250) and Alexa FluorR 488 donkey anti-rabbit IgG (1:250).

The most prominent demonstration was from the ovarian section of a 35 year old female with invasive colon carcinoma infiltrating her ovary. The invasive colon carcinoma in ovary section was stained with anti-ZO2 and anti-Slug antibodies. Comparing this section with normal ovary section stained with the above antibodies showed the presence of large number of carcinoma cells with large nuclei and elevated levels of nuclear ZO2 and Slug not observable in the normal ovary section.

It is thus evidenced that metastatic cancers derived from colon carcinoma in ovary section showed an elevated level of ZO2 and Slug in the nucleus.

Similar observation was seen in a chondrosarcoma sample derived from the bone of a 59 year old female but not in another from a 48 year old female. The results (not shown) evidence that only certain chondrosarcoma sections showed an elevated level of nuclear ZO2 and Slug but not in the other.

Example 15

Co-immunoprecipitation (IP) assays of Slug and ZO-2 were carried out, in accordance with the procedure in Example 4, using COS1 cells transfected with HA-Slug and Flag-ZO-2 or Flag-ZO-2ΔGA constructs.

Equal amounts of total protein were used to immunoprecipitate HA-Slug or Flag-ZO-2, Following SDS-PAGE, the co-precipitation of ZO-2 or Slug, respectively, was monitored by Western blot analysis using antibodies to the Flag or HA tags, respectively.

Figure 13:
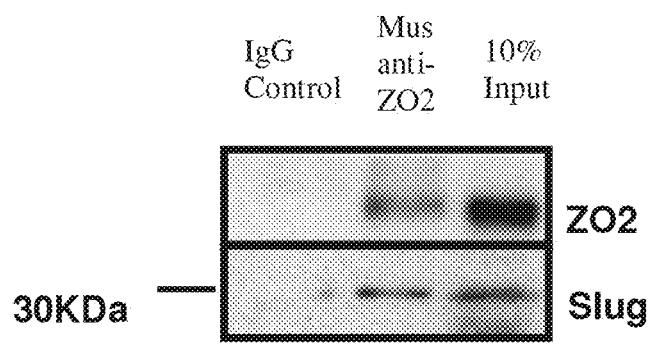
FIG. 13 shows the results of the co-immunoprecipitation (IP) assay of Example 15, evidencing that Flag ZO-2 and HA-Slug co-immunoprecipitate.

The results shown in FIG. 13 evidence that Flag ZO-2 and HA-Slug co-immunoprecipitate.

Example 16

A GST binding assay in accordance with the procedure in Example 3 was performed using a series of point mutated GST-ZO2 proteins. They were incubated with GFP-Slug MDCK lysate and probed for the presence of both GFP-Slug and endogenous Slug using specific antibodies against Slug.

The results (not shown) evidence that ZO2 mutants abolish binding to GFP-SLUG.

Example 17

In this example, a combination of GFP-Slug and mcherry ZO2 was shown to enhance the decrease in E-cadherin promoter activity.

GFP and GFP-Slug stably expressing MDCK cells were seeded at $8\times10^5$ cells per 10 cm tissue culture dish and knocked down with either 33 pmol/ml of si Ctrl or si ZO2 for 72 h using Lipofectamine™ RNAiMax according to the manufacturer instruction. They were reseeded into 24 welled plates at $1\times10^5$ cells per well and transfected with 1 µg of either empty vector or either DsRed or mCherry tagged ZO-2 constructs using Lipofectamine™ 2000 along with 0.2 µg of pGaussia-Luciferase hu E-cadherin promoter reporter and 0.02 µg of pCMV-Vargula-Luciferase. Readings were taken in quadruplets after 24 h using the DLAR4 kit (targetingsystems) according to the manufacturer instructions.

Figure 14:
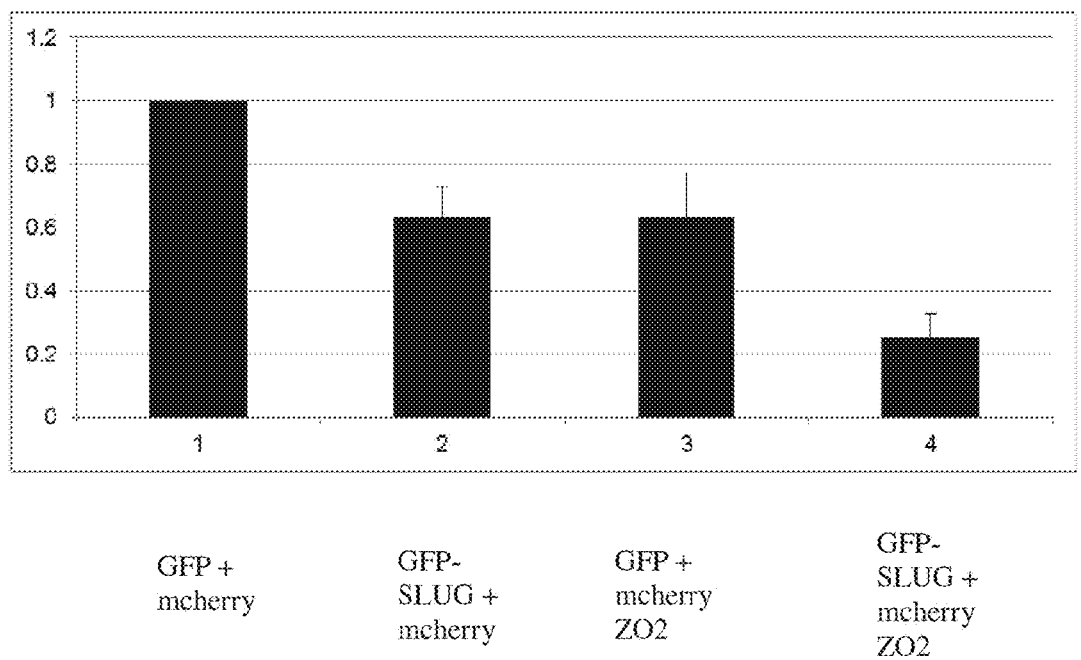
FIG. 14 shows that a combination of GFP-Slug and mcherry ZO2 enhances the decrease in E-cadherin promoter activity in Example 17.

It was shown that both GFP-Slug and mcherry ZO2 can repress the E-cadherin promoter individually. The former can act directly while the latter may act through endogenous Slug, but when both are present they can repress the promoter activity even further. The results are shown in FIG. 14.

The invention claimed is:

1. A method of identifying candidate agents capable of modulating interaction between a first polypeptide and a second polypeptide, wherein the first polypeptide is Zonula Occluden protein 2/tight junction protein 2 (ZO-2/TJP 2) or a functional valiant thereof and the second polypeptide is a Snail zinc finger transcription factor family member selected from the group consisting of a SNAI1 (Snail) polypeptide, a SNAI2 (Slug) polypeptide, or a SNAI3 (Smuc) polypeptide, or a functional variant thereof, the method comprising:

a) contacting the first polypeptide with the second polypeptide and a candidate agent; and b) determining whether the binding of the first polypeptide with the second polypeptide is decreased or increased in the presence of said candidate agent when compared with a control;

wherein the functional variant of ZO-2/TJP2 has at least 95% sequence identity with a ZO-2/TJP2 polypeptide encoded by any one of SEQ ID NOs: 1-9; and wherein the functional variant of the Snail zinc finger transcription factor family member has at least 95 % sequence identity with a SNAI1 (Snail) polypeptide encoded by SEQ ID NO: 12 or 13, a SNAI2 (Slug) polypeptide encoded by SEQ ID NO: 10 or 11, or a SNAI3 (Smuc) polypeptide encoded by SEQ ID NO: 18 or 19.

2. The method of claim 1, wherein the ZO-2/TJP2 polypeptide is encoded by a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8 and SEQ ID NO: 9.

3. The method of claim 1, wherein the Snail zinc finger transcription factor family member polypeptide is selected from the group consisting of SNAI1 (Snail) encoded by SEQ ID NO: 12 or 13, SNAI2 (Slug) encoded by SEQ ID NO: 10 or 11, and SNAI3 (Smuc) encoded by SEQ ID NO: 18 or 19.

4. The method of claim 1, wherein the first polypeptide, the second polypeptide and the candidate agent are contacted separately or simultaneously.

5. The method of claim 1, wherein a change in the binding is determined by a method selected from the group consisting of a yeast two-hybrid screen, a glutathione S-transferase (GST) binding assay, immunoprecipitation, immunofluorescence and combinations thereof.

6. The method of claim 1, wherein the functional variant of the Snail zinc finger transcription factor family member further comprises tryptophan that corresponds to the tryptophan at amino acid position 199 of said Snail zinc finger transcription factor family member polypeptide encoded by SEQ ID NO: 10, or tryptophan that corresponds to the tryptophan at amino acid position 198 of said Snail zinc finger transcription factor family member polypeptide encoded by SEQ ID NO: 11.

7. The method of claim 1, wherein the candidate agent is selected from the group consisting of small organic molecules, small inorganic molecules, aptamers, polypeptides, antibodies and fragments thereof, and nucleic acids.

8. The method of claim 1, wherein the candidate agent comprises an aromatic ring, or a fragment of the second polypeptide comprising a zinc finger 3 (ZNF3) domain.

* * * * *